United States Patent
Veiby et al.

(10) Patent No.: US 9,421,277 B2
(45) Date of Patent: Aug. 23, 2016

(54) ANTIBODIES THAT BIND OV064 AND METHODS OF USE THEREFOR

(71) Applicant: Millennium Pharmaceuticals, Inc., Cambridge, MA (US)

(72) Inventors: Ole Petter Veiby, Westborough, MA (US); John S. Babcook, Vancouver (CA)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 133 days.

(21) Appl. No.: 14/249,299

(22) Filed: Apr. 9, 2014

(65) Prior Publication Data

US 2014/0328751 A1    Nov. 6, 2014

Related U.S. Application Data

(60) Continuation of application No. 13/666,751, filed on Nov. 1, 2012, now Pat. No. 8,759,490, which is a division of application No. 11/886,434, filed as application No. PCT/US2006/008892 on Mar. 10, 2006, now Pat. No. 8,323,645.

(60) Provisional application No. 60/664,828, filed on Mar. 24, 2005.

(51) Int. Cl.
| | |
|---|---|
| *C07K 16/30* | (2006.01) |
| *A61K 47/48* | (2006.01) |
| *G01N 33/574* | (2006.01) |
| *A61K 51/10* | (2006.01) |
| *C07K 16/00* | (2006.01) |
| *A61K 39/00* | (2006.01) |

(52) U.S. Cl.
CPC ....... *A61K 47/48569* (2013.01); *A61K 51/1045* (2013.01); *A61K 51/1072* (2013.01); *A61K 51/1093* (2013.01); *C07K 16/00* (2013.01); *C07K 16/30* (2013.01); *C07K 16/3069* (2013.01); *G01N 33/57484* (2013.01); *G01N 33/57492* (2013.01); *A61K 2039/505* (2013.01); *C07K 2317/21* (2013.01); *C07K 2317/34* (2013.01); *C07K 2317/565* (2013.01); *C07K 2317/73* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 6,891,030 B2 | 5/2005 | Chen | |
| 6,962,980 B2 | 11/2005 | Mitcham et al. | |
| 7,189,563 B2 | 3/2007 | Eaton et al. | |
| 7,202,334 B1 | 4/2007 | Mitcham et al. | |
| 7,304,149 B2 | 12/2007 | Murphy et al. | |
| 7,498,298 B2 | 3/2009 | Doronina et al. | |
| 7,619,068 B2 | 11/2009 | Pilkington et al. | |
| 7,622,565 B2 | 11/2009 | Chen | |
| 7,737,255 B1 | 6/2010 | Salceda et al. | |
| 7,745,394 B2 | 6/2010 | Doronina et al. | |
| 7,847,081 B2 | 12/2010 | Chen | |
| 7,875,702 B2 | 1/2011 | Chen | |
| 7,888,477 B2 | 2/2011 | Bangur et al. | |
| 2001/0034052 A1 * | 10/2001 | Dillon et al. | C07K 14/47 435/200 |
| 2002/0051990 A1 | 5/2002 | Ople et al. | |
| 2002/0165347 A1 | 11/2002 | Fox et al. | |
| 2003/0181668 A1 | 9/2003 | Eaton et al. | |
| 2005/0031634 A1 | 2/2005 | Bangur et al. | |
| 2007/0099251 A1 | 5/2007 | Zhang et al. | |
| 2007/0160578 A1 | 7/2007 | Waldmann et al. | |
| 2008/0008706 A1 | 1/2008 | Dong et al. | |
| 2008/0025981 A1 | 1/2008 | Young et al. | |
| 2008/0299042 A1 | 12/2008 | Bechtel et al. | |
| 2009/0054624 A1 | 2/2009 | Baker et al. | |
| 2009/0136490 A1 | 5/2009 | Pilkington et al. | |
| 2011/0177082 A1 | 7/2011 | Bangur et al. | |

FOREIGN PATENT DOCUMENTS

| | | |
|---|---|---|
| EP | 1 141 290 B1 | 7/2010 |
| WO | WO 02/02587 A1 | 1/2002 |
| WO | WO 2004/003019 A2 | 1/2004 |
| WO | WO 2004/101756 A2 | 11/2004 |
| WO | WO 2006/053110 A2 | 5/2006 |

OTHER PUBLICATIONS

Brorson et al., "Mutational analysis of avidity and fine specificity of anti-levan antibodies" *J. Immunol.*, 163:6694-6701 (1999).

Brummell et al., "Probing the combining site of an anti-carbohydrate antibody by saturation-mutagenesis: role of the heavy-chain CDR3 residues" *Biochemistry*, 32:1180-1187 (1993).

Burks et al., "In vitro scanning saturation mutagenesis of an antibody binding pocket" *PNAS*, 94:412-417 (1997).

Casset et al., "A peptide mimetic of an anti-CD4 monoclonal antibody by rational design" *Biochem. Biophys. Res. Comm.*, 307:198-205 (2003).

(Continued)

*Primary Examiner* — Brad Duffy
*Assistant Examiner* — Nelson B Moseley, II
(74) *Attorney, Agent, or Firm* — Finnegan, Henderson, Farabow, Garrett & Dunner

(57) ABSTRACT

Antibodies and antigen-binding fragments of antibodies that bind OV064 are disclosed. The antibodies bind an extracellular domain of OV064. Some of the antibodies and antigen-binding fragments bind an epitope on OV064 sufficient to induce internalization. In some embodiments, the antibodies are humanized, chimeric or human. Nucleic acids and vectors encoding the antibodies or portions thereof, recombinant cells that contain the nucleic acids, and compositions comprising the antibodies or antigen-binding fragments are also disclosed. The invention also provides therapeutic and diagnostic methods utilizing the antibodies and antigen-binding fragments provided herein.

12 Claims, 1 Drawing Sheet

(56) References Cited

OTHER PUBLICATIONS

Chen et al. (1999) "Selection and analysis of an optimized anti-VEGF antibody: crystal structure of an affinity-matured Fab in complex with antigen" *J. Mol. Biol.*, 293:865-881.

Coleman, "Effects of amino acid sequence changes on antibody-antigen interactions" *Res. Immunol.*, 145:33-36 (1994).

De Pascalis et al. (2002) "Grafting of "abbreviated" complementarity-determining regions containing specificity-determining residues essential for ligand contact to engineer a less immunogenic humanized monoclonal antibody" *J. Immunol.*, 169:3076-3084.

European patent application 11169780.1, by Millennium Pharmaceuticals, Inc.: Extended European Search Report, including Opinion, dated Oct. 10, 2011.

Holm et al. (2007) "Functional mapping and single chain construction of the anti-cytokeratin 8 monoclonal antibody TS1" *Mol. Immunol.*, 44:1075-1084.

Jang et al., "The structural basis for DNA binding by an anti-DNA autoantibody" *Mol. Immunol.*, 35:1207-1217 (1998).

Kobayashi et al., "Tryptophan H33 plays an important role in pyrimidine (6-4) pyrimidone photoproduct binding by a high-affinity antibody" *Protein Eng.*, 12:879-844 (1999).

Kumar et al., "Molecular cloning and expression of the Fabs of human autoantibodies in *Escherichia coli*. Determination of the heavy or light chain contribution to the anti-DNA/-cardiolipin activity of the Fab" *J. Biol. Chem.*, 275:35129-35136 (2000).

MacCallum et al., "Antibody-antigen interactions: contact analysis and binding site topography" *J. Mol. Biol.*, 262:732-745 (1996).

Rudikoff et al., "Single amino acid substitution altering antigen-binding specificity" *Proc Natl Acad Sci USA*, 79:1979-1983 (1982).

Smith-Gill et al., "Contributions of immunoglobulin heavy and light chains to antibody specificity for lysozyme and two haptens" *J. Immunol.*, 139:4135-4144 (1987).

Song et al., "Light chain of natural antibody plays a dominant role in protein antigen binding" *Biochem. Biophys. Res. Comm.*, 268:390-394 (2000).

Vajdos et al., "Comprehensive functional maps of the antigen-binding site of an anti-ErbB2 antibody obtained with shotgun scanning mutagenesis" *J. Mol. Biol.*, 320:415-428 (2002).

Ward et al., "Binding activities of a repertoire of single immunoglobulin variable domains secreted from *Escherichia coli*" Nature, 341:544-546 (1989).

Wu et al., "Humanization of a murine monoclonal antibody by simultaneous optimization of framework and CDR residues" *J. Mol. Biol.*, 294:151-162 (1999).

* cited by examiner

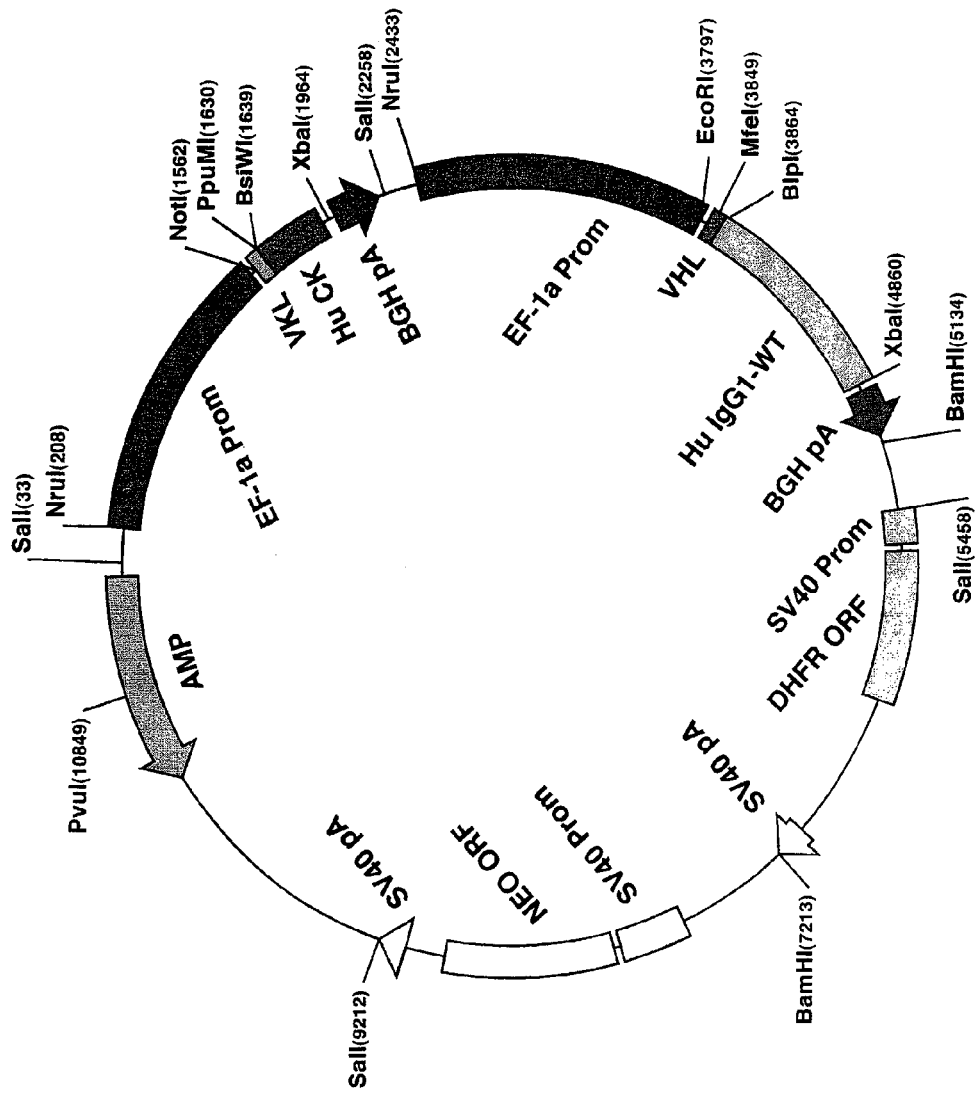

SEQUENCE LISTING

<160> NUMBER OF SEQ ID NOS: 46

<210> SEQ ID NO 1
<211> LENGTH: 1422
<212> TYPE: DNA
<213> ORGANISM: Homo Sapiens
<220> FEATURE:
<221> NAME/KEY: CDS
<222> LOCATION: (13)...(1416)

<400> SEQUENCE: 1

```
gaattcctca cc atg gag ttg gga ctg tgc tgg gtt ttt ctc gtt gct ctt        51
             Met Glu Leu Gly Leu Cys Trp Val Phe Leu Val Ala Leu
              1               5                   10 tta aga ggt gtc cag tgt cag gtg cag ctg gtg gag tct ggg gga ggc           99
Leu Arg Gly Val Gln Cys Gln Val Gln Leu Val Glu Ser Gly Gly Gly
         15                  20                  25 gtg gtc cag cct ggg agg tcc ctg aga ctc tcc tgt gca gcg tct gga          147
Val Val Gln Pro Gly Arg Ser Leu Arg Leu Ser Cys Ala Ala Ser Gly
 30                  35                  40                  45 ttc acc ttc agt agc tat ggc atg cac tgg gtc cgc cag gct cca ggc          195
Phe Thr Phe Ser Ser Tyr Gly Met His Trp Val Arg Gln Ala Pro Gly
                 50                  55                  60
```

```
aag ggg ctg gag tgg gtg gca gtt ata tgg tat gat ggc aat aat aaa       243
Lys Gly Leu Glu Trp Val Ala Val Ile Trp Tyr Asp Gly Asn Asn Lys
             65                  70                  75 tac tat gca gac tcc gtg aag ggc cga ttc acc atc tcc aga gac aat       291
Tyr Tyr Ala Asp Ser Val Lys Gly Arg Phe Thr Ile Ser Arg Asp Asn
             80                  85                  90 tcc aag aac aca ctg tat ctg caa atg aac agc ctg aga gcc gag gac       339
Ser Lys Asn Thr Leu Tyr Leu Gln Met Asn Ser Leu Arg Ala Glu Asp
 95                 100                 105 acg gct gtg tat tac tgt gcg aga acg tcg ggt ata gca gcc ttt gac       387
Thr Ala Val Tyr Tyr Cys Ala Arg Thr Ser Gly Ile Ala Ala Phe Asp
110                 115                 120                 125 tac tgg ggc cag gga acc ctg gtc acc gtc agc tca gcc tcc acc aag       435
Tyr Trp Gly Gln Gly Thr Leu Val Thr Val Ser Ser Ala Ser Thr Lys
                130                 135                 140 ggc cca tcg gtc ttc ccc ctg gca ccc tcc tcc aag agc acc tct ggg       483
Gly Pro Ser Val Phe Pro Leu Ala Pro Ser Ser Lys Ser Thr Ser Gly
            145                 150                 155 ggc aca gcg gcc ctg ggc tgc ctg gtc aag gac tac ttc ccc gaa ccg       531
Gly Thr Ala Ala Leu Gly Cys Leu Val Lys Asp Tyr Phe Pro Glu Pro
        160                 165                 170 gtg acg gtg tcg tgg aac tca ggc gcc ctg acc agc ggc gtg cac acc       579
Val Thr Val Ser Trp Asn Ser Gly Ala Leu Thr Ser Gly Val His Thr
    175                 180                 185 ttc ccg gct gtc cta cag tcc tca gga ctc tac tcc ctc agc agc gtg       627
Phe Pro Ala Val Leu Gln Ser Ser Gly Leu Tyr Ser Leu Ser Ser Val
190                 195                 200                 205 gtg acc gtg ccc tcc agc agc ttg ggc acc cag acc tac atc tgc aac       675
Val Thr Val Pro Ser Ser Ser Leu Gly Thr Gln Thr Tyr Ile Cys Asn
                210                 215                 220 gtg aat cac aag ccc agc aac acc aag gtg gac aag aaa gtt gag ccc       723
Val Asn His Lys Pro Ser Asn Thr Lys Val Asp Lys Lys Val Glu Pro
            225                 230                 235 aaa tct tgt gac aaa act cac aca tgc cca ccg tgc cca gca cct gaa       771
Lys Ser Cys Asp Lys Thr His Thr Cys Pro Pro Cys Pro Ala Pro Glu
        240                 245                 250 ctc ctg ggg gga ccg tca gtc ttc ctc ttc ccc cca aaa ccc aag gac       819
Leu Leu Gly Gly Pro Ser Val Phe Leu Phe Pro Pro Lys Pro Lys Asp
    255                 260                 265 acc ctc atg atc tcc cgg acc cct gag gtc aca tgc gtg gtg gtg gac       867
Thr Leu Met Ile Ser Arg Thr Pro Glu Val Thr Cys Val Val Val Asp
270                 275                 280                 285 gtg agc cac gaa gac cct gag gtc aag ttc aac tgg tac gtg gac ggc       915
Val Ser His Glu Asp Pro Glu Val Lys Phe Asn Trp Tyr Val Asp Gly
                290                 295                 300 gtg gag gtg cat aat gcc aag aca aag ccg cgg gag gag cag tac aac       963
Val Glu Val His Asn Ala Lys Thr Lys Pro Arg Glu Glu Gln Tyr Asn
            305                 310                 315 agc acg tac cgt gtg gtc agc gtc ctc acc gtc ctg cac cag gac tgg      1011
Ser Thr Tyr Arg Val Val Ser Val Leu Thr Val Leu His Gln Asp Trp
        320                 325                 330 ctg aat ggc aag gag tac aag tgc aag gtc tcc aac aaa gcc ctc cca      1059
Leu Asn Gly Lys Glu Tyr Lys Cys Lys Val Ser Asn Lys Ala Leu Pro
    335                 340                 345 gcc ccc atc gag aaa acc atc tcc aaa gcc aaa ggg cag ccc cga gaa      1107
Ala Pro Ile Glu Lys Thr Ile Ser Lys Ala Lys Gly Gln Pro Arg Glu
350                 355                 360                 365 cca cag gtg tac acc ctg ccc cca tcc cgg gat gag ctg acc aag aac      1155
Pro Gln Val Tyr Thr Leu Pro Pro Ser Arg Asp Glu Leu Thr Lys Asn
```

```
                    370             375             380
cag gtc agc ctg acc tgc ctg gtc aaa ggc ttc tat ccc agc gac atc    1203
Gln Val Ser Leu Thr Cys Leu Val Lys Gly Phe Tyr Pro Ser Asp Ile
        385             390             395 gcc gtg gag tgg gag agc aat ggg cag ccg gag aac aac tac aag acc    1251
Ala Val Glu Trp Glu Ser Asn Gly Gln Pro Glu Asn Asn Tyr Lys Thr
400             405             410 acg cct ccc gtg ctg gac tcc gac ggc tcc ttc ttc ctc tac agc aag    1299
Thr Pro Pro Val Leu Asp Ser Asp Gly Ser Phe Phe Leu Tyr Ser Lys
    415             420             425 ctc acc gtg gac aag agc agg tgg cag cag ggg aac gtc ttc tca tgc    1347
Leu Thr Val Asp Lys Ser Arg Trp Gln Gln Gly Asn Val Phe Ser Cys
430             435             440             445 tcc gtg atg cat gag gct ctg cac aac cac tac acg cag aag agc ctc    1395
Ser Val Met His Glu Ala Leu His Asn His Tyr Thr Gln Lys Ser Leu
            450             455             460 tcc ctg tct ccg ggt aaa taa tctaga                                 1422
Ser Leu Ser Pro Gly Lys  *
        465

<210> SEQ ID NO 2
<211> LENGTH: 467
<212> TYPE: PRT
<213> ORGANISM: Homo Sapiens

<400> SEQUENCE: 2

Met Glu Leu Gly Leu Cys Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Gly Asn Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Thr Ser Gly Ile Ala Ala Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240
```

```
Asp Lys Thr His Thr Cys Pro Pro Cys Pro Ala Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 3
<211> LENGTH: 743
<212> TYPE: DNA
<213> ORGANISM: Homo Sapiens
<220> FEATURE:
<221> NAME/KEY: CDS
<222> LOCATION: (15)...(737)

<400> SEQUENCE: 3
gcggccgcct cacc atg gtg ttg cag acc cag gtc ttc att tct ctg ttg       50
                Met Val Leu Gln Thr Gln Val Phe Ile Ser Leu Leu
                1               5                   10 ctc tgg atc tct ggt gcc tac ggg gac aac gtg atg acc cag tct cca       98
Leu Trp Ile Ser Gly Ala Tyr Gly Asp Asn Val Met Thr Gln Ser Pro
        15                  20                  25 gac tcc ctg gct gtc ttt ctg ggc gag agg gcc acc atc aac tgc aag      146
Asp Ser Leu Ala Val Phe Leu Gly Glu Arg Ala Thr Ile Asn Cys Lys
    30                  35                  40 tcc agc cag agt gtt tta tac aac tcc aac tat aag aac tac tta gct      194
Ser Ser Gln Ser Val Leu Tyr Asn Ser Asn Tyr Lys Asn Tyr Leu Ala
45                  50                  55                  60 tgg tac caa cag aaa cca gga cag cct cct aag ctg ctc ttt tac tgg      242
Trp Tyr Gln Gln Lys Pro Gly Gln Pro Pro Lys Leu Leu Phe Tyr Trp
                65                  70                  75 gca tct acc cgg gaa tcc ggg gtc cct gac cga ttc agt ggc agc ggg      290
Ala Ser Thr Arg Glu Ser Gly Val Pro Asp Arg Phe Ser Gly Ser Gly
            80                  85                  90
```

-continued

```
tct ggg aca gat ttc act ctc acc atc agc agc ctg cag gct gaa gat    338
Ser Gly Thr Asp Phe Thr Leu Thr Ile Ser Ser Leu Gln Ala Glu Asp
         95                  100                 105 gtg gca gtt tat tac tgt cag caa tat tat aat act ccg ctc act ttc    386
Val Ala Val Tyr Tyr Cys Gln Gln Tyr Tyr Asn Thr Pro Leu Thr Phe
110                 115                 120 ggc gga ggg acc aaa gtg gag atc aaa cgt acg gtg gct gca cca tct    434
Gly Gly Gly Thr Lys Val Glu Ile Lys Arg Thr Val Ala Ala Pro Ser
125                 130                 135                 140 gtc ttc atc ttc ccg cca tct gat gag cag ttg aaa tct gga act gcc    482
Val Phe Ile Phe Pro Pro Ser Asp Glu Gln Leu Lys Ser Gly Thr Ala
                145                 150                 155 tct gtt gtg tgc ctg ctg aat aac ttc tat ccc aga gag gcc aaa gta    530
Ser Val Val Cys Leu Leu Asn Asn Phe Tyr Pro Arg Glu Ala Lys Val
            160                 165                 170 cag tgg aag gtg gat aac gcc ctc caa tcg ggt aac tcc cag gag agt    578
Gln Trp Lys Val Asp Asn Ala Leu Gln Ser Gly Asn Ser Gln Glu Ser
        175                 180                 185 gtc aca gag cag gac agc aag gac agc acc tac agc ctc agc agc acc    626
Val Thr Glu Gln Asp Ser Lys Asp Ser Thr Tyr Ser Leu Ser Ser Thr
    190                 195                 200 ctg acc ctg agc aaa gca gac tac gag aaa cac aaa gtc tac gcc tgc    674
Leu Thr Leu Ser Lys Ala Asp Tyr Glu Lys His Lys Val Tyr Ala Cys
205                 210                 215                 220 gaa gtc acc cat cag ggc ctg agc tcg ccc gtc aca aag agc ttc aac    722
Glu Val Thr His Gln Gly Leu Ser Ser Pro Val Thr Lys Ser Phe Asn
                225                 230                 235 agg gga gag tgt tag tctaga                                          743
Arg Gly Glu Cys *
            240

<210> SEQ ID NO 4
<211> LENGTH: 240
<212> TYPE: PRT
<213> ORGANISM: Homo Sapiens

<400> SEQUENCE: 4

Met Val Leu Gln Thr Gln Val Phe Ile Ser Leu Leu Trp Ile Ser
 1               5                  10                  15

Gly Ala Tyr Gly Asp Asn Val Met Thr Gln Ser Pro Asp Ser Leu Ala
                20                  25                  30

Val Phe Leu Gly Glu Arg Ala Thr Ile Asn Cys Lys Ser Ser Gln Ser
            35                  40                  45

Val Leu Tyr Asn Ser Asn Tyr Lys Asn Tyr Leu Ala Trp Tyr Gln Gln
     50                  55                  60

Lys Pro Gly Gln Pro Pro Lys Leu Leu Phe Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Asn Thr Pro Leu Thr Phe Gly Gly Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160
```

```
Leu Leu Asn Asn Phe Tyr Pro Arg Glu Ala Lys Val Gln Trp Lys Val
            165                 170                 175
Asp Asn Ala Leu Gln Ser Gly Asn Ser Gln Glu Ser Val Thr Glu Gln
        180                 185                 190
Asp Ser Lys Asp Ser Thr Tyr Ser Leu Ser Ser Thr Leu Thr Leu Ser
    195                 200                 205
Lys Ala Asp Tyr Glu Lys His Lys Val Tyr Ala Cys Glu Val Thr His
210                 215                 220
Gln Gly Leu Ser Ser Pro Val Thr Lys Ser Phe Asn Arg Gly Glu Cys
225                 230                 235                 240

<210> SEQ ID NO 5
<211> LENGTH: 1419
<212> TYPE: DNA
<213> ORGANISM: Homo Sapiens
<220> FEATURE:
<221> NAME/KEY: CDS
<222> LOCATION: (13)...(1413)

<400> SEQUENCE: 5
```

| | | |
|---|---|---|
| gaattcctca cc atg gaa ttt gga ctt cgc tgg gtt ttc ctt gtt gct ata | | 51 |
| Met Glu Phe Gly Leu Arg Trp Val Phe Leu Val Ala Ile | | |
| 1               5                  10 | | |
| tta gaa ggt gtc cag tgt gag gtg cag ctg gtg gag tct ggg gga ggc | | 99 |
| Leu Glu Gly Val Gln Cys Glu Val Gln Leu Val Glu Ser Gly Gly Gly | | |
| 15                  20                  25 | | |
| ttg gta cag cct ggg ggg tcc ctg aga ctc tcc tgt gca gcc tct gga | | 147 |
| Leu Val Gln Pro Gly Gly Ser Leu Arg Leu Ser Cys Ala Ala Ser Gly | | |
| 30                  35                  40                  45 | | |
| ttc tcc ttc agt agc tac gac atg cac tgg gtc cgc caa gct aca gga | | 195 |
| Phe Ser Phe Ser Ser Tyr Asp Met His Trp Val Arg Gln Ala Thr Gly | | |
| 50                  55                  60 | | |
| aaa ggt ctg gag tgg gtc tca ggt att gat att gct ggt gac aca tac | | 243 |
| Lys Gly Leu Glu Trp Val Ser Gly Ile Asp Ile Ala Gly Asp Thr Tyr | | |
| 65                  70                  75 | | |
| tat cca ggc tcc gtg aag ggc cga ttc acc atc tcc aga gaa aat gcc | | 291 |
| Tyr Pro Gly Ser Val Lys Gly Arg Phe Thr Ile Ser Arg Glu Asn Ala | | |
| 80                  85                  90 | | |
| aag aac tcc ttg tat ctt caa atg aac agc ctg aga gcc ggg gac acg | | 339 |
| Lys Asn Ser Leu Tyr Leu Gln Met Asn Ser Leu Arg Ala Gly Asp Thr | | |
| 95                  100                 105 | | |
| gct gtg tat tac tgt gca aga ggt gac tac gat ggt act ttt gac tac | | 387 |
| Ala Val Tyr Tyr Cys Ala Arg Gly Asp Tyr Asp Gly Thr Phe Asp Tyr | | |
| 110                 115                 120                 125 | | |
| tgg ggc cag gga acc ctg gtc acc gtc agc tca gcc tcc acc aag ggc | | 435 |
| Trp Gly Gln Gly Thr Leu Val Thr Val Ser Ser Ala Ser Thr Lys Gly | | |
| 130                 135                 140 | | |
| cca tcg gtc ttc ccc ctg gca ccc tcc tcc aag agc acc tct ggg ggc | | 483 |
| Pro Ser Val Phe Pro Leu Ala Pro Ser Ser Lys Ser Thr Ser Gly Gly | | |
| 145                 150                 155 | | |
| aca gcg gcc ctg ggc tgc ctg gtc aag gac tac ttc ccc gaa ccg gtg | | 531 |
| Thr Ala Ala Leu Gly Cys Leu Val Lys Asp Tyr Phe Pro Glu Pro Val | | |
| 160                 165                 170 | | |
| acg gtg tcg tgg aac tca ggc gcc ctg acc agc ggc gtg cac acc ttc | | 579 |
| Thr Val Ser Trp Asn Ser Gly Ala Leu Thr Ser Gly Val His Thr Phe | | |
| 175                 180                 185 | | |
| ccg gct gtc cta cag tcc tca gga ctc tac tcc ctc agc agc gtg gtg | | 627 |
| Pro Ala Val Leu Gln Ser Ser Gly Leu Tyr Ser Leu Ser Ser Val Val | | |
| 190                 195                 200                 205 | | |
| acc gtg ccc tcc agc agc ttg ggc acc cag acc tac atc tgc aac gtg | | 675 |

```
                                                                                723
aat cac aag ccc agc aac acc aag gtg gac aag aaa gtt gag ccc aaa
Asn His Lys Pro Ser Asn Thr Lys Val Asp Lys Lys Val Glu Pro Lys
            225                 230                 235

771
tct tgt gac aaa act cac aca tgc cca ccg tgc cca gca cct gaa ctc
Ser Cys Asp Lys Thr His Thr Cys Pro Pro Cys Pro Ala Pro Glu Leu
        240                 245                 250

819
ctg ggg gga ccg tca gtc ttc ctc ttc ccc cca aaa ccc aag gac acc
Leu Gly Gly Pro Ser Val Phe Leu Phe Pro Pro Lys Pro Lys Asp Thr
    255                 260                 265

867
ctc atg atc tcc cgg acc cct gag gtc aca tgc gtg gtg gtg gac gtg
Leu Met Ile Ser Arg Thr Pro Glu Val Thr Cys Val Val Val Asp Val
270                 275                 280                 285

915
agc cac gaa gac cct gag gtc aag ttc aac tgg tac gtg gac ggc gtg
Ser His Glu Asp Pro Glu Val Lys Phe Asn Trp Tyr Val Asp Gly Val
                290                 295                 300

963
gag gtg cat aat gcc aag aca aag ccg cgg gag gag cag tac aac agc
Glu Val His Asn Ala Lys Thr Lys Pro Arg Glu Glu Gln Tyr Asn Ser
            305                 310                 315

1011
acg tac cgt gtg gtc agc gtc ctc acc gtc ctg cac cag gac tgg ctg
Thr Tyr Arg Val Val Ser Val Leu Thr Val Leu His Gln Asp Trp Leu
        320                 325                 330

1059
aat ggc aag gag tac aag tgc aag gtc tcc aac aaa gcc ctc cca gcc
Asn Gly Lys Glu Tyr Lys Cys Lys Val Ser Asn Lys Ala Leu Pro Ala
    335                 340                 345

1107
ccc atc gag aaa acc atc tcc aaa gcc aaa ggg cag ccc cga gaa cca
Pro Ile Glu Lys Thr Ile Ser Lys Ala Lys Gly Gln Pro Arg Glu Pro
350                 355                 360                 365

1155
cag gtg tac acc ctg ccc cca tcc cgg gat gag ctg acc aag aac cag
Gln Val Tyr Thr Leu Pro Pro Ser Arg Asp Glu Leu Thr Lys Asn Gln
                370                 375                 380

1203
gtc agc ctg acc tgc ctg gtc aaa ggc ttc tat ccc agc gac atc gcc
Val Ser Leu Thr Cys Leu Val Lys Gly Phe Tyr Pro Ser Asp Ile Ala
            385                 390                 395

1251
gtg gag tgg gag agc aat ggg cag ccg gag aac aac tac aag acc acg
Val Glu Trp Glu Ser Asn Gly Gln Pro Glu Asn Asn Tyr Lys Thr Thr
        400                 405                 410

1299
cct ccc gtg ctg gac tcc gac ggc tcc ttc ttc ctc tac agc aag ctc
Pro Pro Val Leu Asp Ser Asp Gly Ser Phe Phe Leu Tyr Ser Lys Leu
    415                 420                 425

1347
acc gtg gac aag agc agg tgg cag cag ggg aac gtc ttc tca tgc tcc
Thr Val Asp Lys Ser Arg Trp Gln Gln Gly Asn Val Phe Ser Cys Ser
430                 435                 440                 445

1395
gtg atg cat gag gct ctg cac aac cac tac acg cag aag agc ctc tcc
Val Met His Glu Ala Leu His Asn His Tyr Thr Gln Lys Ser Leu Ser
                450                 455                 460

1419
ctg tct ccg ggt aaa taa tctaga
Leu Ser Pro Gly Lys *
            465

<210> SEQ ID NO 6
<211> LENGTH: 466
<212> TYPE: PRT
<213> ORGANISM: Homo Sapiens

<400> SEQUENCE: 6

Met Glu Phe Gly Leu Arg Trp Val Phe Leu Val Ala Ile Leu Glu Gly
 1               5                  10                  15

Val Gln Cys Glu Val Gln Leu Val Glu Ser Gly Gly Gly Leu Val Gln
```

```
                    20                  25                  30
Pro Gly Gly Ser Leu Arg Leu Ser Cys Ala Ala Ser Gly Phe Ser Phe
            35                  40                  45
Ser Ser Tyr Asp Met His Trp Val Arg Gln Ala Thr Gly Lys Gly Leu
    50                  55                  60
Glu Trp Val Ser Gly Ile Asp Ile Ala Gly Asp Thr Tyr Tyr Pro Gly
65                  70                  75                  80
Ser Val Lys Gly Arg Phe Thr Ile Ser Arg Glu Asn Ala Lys Asn Ser
                85                  90                  95
Leu Tyr Leu Gln Met Asn Ser Leu Arg Ala Gly Asp Thr Ala Val Tyr
            100                 105                 110
Tyr Cys Ala Arg Gly Asp Tyr Asp Gly Thr Phe Asp Tyr Trp Gly Gln
        115                 120                 125
Gly Thr Leu Val Thr Val Ser Ser Ala Ser Thr Lys Gly Pro Ser Val
    130                 135                 140
Phe Pro Leu Ala Pro Ser Ser Lys Ser Thr Ser Gly Gly Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
            180                 185                 190
Leu Gln Ser Ser Gly Leu Tyr Ser Leu Ser Ser Val Val Thr Val Pro
        195                 200                 205
Ser Ser Ser Leu Gly Thr Gln Thr Tyr Ile Cys Asn Val Asn His Lys
    210                 215                 220
Pro Ser Asn Thr Lys Val Asp Lys Lys Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
        275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Asp Glu Leu Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
```

Glu Ala Leu His Asn His Tyr Thr Gln Lys Ser Leu Ser Leu Ser Pro
    450                 455                 460

Gly Lys
465

<210> SEQ ID NO 7
<211> LENGTH: 740
<212> TYPE: DNA
<213> ORGANISM: Homo Sapiens
<220> FEATURE:
<221> NAME/KEY: CDS
<222> LOCATION: (15)...(734)

<400> SEQUENCE: 7

```
gcggccgcct cacc atg agg gtc cct gct cag ctt ctg ggg ctg cta atg         50
                Met Arg Val Pro Ala Gln Leu Leu Gly Leu Leu Met
                 1               5                  10 ctc tgg gtc cct gga tcc agt ggg gat att gtg atg acc cag act cca         98
Leu Trp Val Pro Gly Ser Ser Gly Asp Ile Val Met Thr Gln Thr Pro
         15                  20                  25 ctc tcc tca cct gtc acc ctt gga cag ccg gcc tcc atc tcc tgc agg        146
Leu Ser Ser Pro Val Thr Leu Gly Gln Pro Ala Ser Ile Ser Cys Arg
     30                  35                  40 tct agt caa agc ctc gta cac agt gat gga aac acc tac ttg agt tgg        194
Ser Ser Gln Ser Leu Val His Ser Asp Gly Asn Thr Tyr Leu Ser Trp
 45                  50                  55                  60 ctt cag cag agg cca ggc cag cct cta aga ctc cta ttt tat aag att        242
Leu Gln Gln Arg Pro Gly Gln Pro Leu Arg Leu Leu Phe Tyr Lys Ile
                 65                  70                  75 tct aac cgg ttc tct ggg gtc cca gac aga ttc agt ggc agt ggg gca        290
Ser Asn Arg Phe Ser Gly Val Pro Asp Arg Phe Ser Gly Ser Gly Ala
             80                  85                  90 ggg aca gat ttc aca ctg ata atc aac agg gtg gaa gct gag gat gtc        338
Gly Thr Asp Phe Thr Leu Ile Ile Asn Arg Val Glu Ala Glu Asp Val
         95                 100                 105 ggg gtt tat tac tgc atg cac gct aca caa ttt ccg atc acc ttc ggc        386
Gly Val Tyr Tyr Cys Met His Ala Thr Gln Phe Pro Ile Thr Phe Gly
    110                 115                 120 caa ggg aca cga ctg gag att aaa cgt acg gtg gct gca cca tct gtc        434
Gln Gly Thr Arg Leu Glu Ile Lys Arg Thr Val Ala Ala Pro Ser Val
125                 130                 135                 140 ttc atc ttc ccg cca tct gat gag cag ttg aaa tct gga act gcc tct        482
Phe Ile Phe Pro Pro Ser Asp Glu Gln Leu Lys Ser Gly Thr Ala Ser
                145                 150                 155 gtt gtg tgc ctg ctg aat aac ttc tat ccc aga gag gcc aaa gta cag        530
Val Val Cys Leu Leu Asn Asn Phe Tyr Pro Arg Glu Ala Lys Val Gln
            160                 165                 170 tgg aag gtg gat aac gcc ctc caa tcg ggt aac tcc cag gag agt gtc        578
Trp Lys Val Asp Asn Ala Leu Gln Ser Gly Asn Ser Gln Glu Ser Val
        175                 180                 185 aca gag cag gac agc aag gac agc acc tac agc ctc agc agc acc ctg        626
Thr Glu Gln Asp Ser Lys Asp Ser Thr Tyr Ser Leu Ser Ser Thr Leu
    190                 195                 200 acc ctg agc aaa gca gac tac gag aaa cac aaa gtc tac gcc tgc gaa        674
Thr Leu Ser Lys Ala Asp Tyr Glu Lys His Lys Val Tyr Ala Cys Glu
205                 210                 215                 220 gtc acc cat cag ggc ctg agc tcg ccc gtc aca aag agc ttc aac agg        722
Val Thr His Gln Gly Leu Ser Ser Pro Val Thr Lys Ser Phe Asn Arg
                225                 230                 235 gga gag tgt tag tctaga                                                 740
```

Gly Glu Cys  *

<210> SEQ ID NO 8
<211> LENGTH: 239
<212> TYPE: PRT
<213> ORGANISM: Homo Sapiens

<400> SEQUENCE: 8

Met Arg Val Pro Ala Gln Leu Leu Gly Leu Leu Met Leu Trp Val Pro
1               5                   10                  15

Gly Ser Ser Gly Asp Ile Val Met Thr Gln Thr Pro Leu Ser Ser Pro
            20                  25                  30

Val Thr Leu Gly Gln Pro Ala Ser Ile Ser Cys Arg Ser Ser Gln Ser
        35                  40                  45

Leu Val His Ser Asp Gly Asn Thr Tyr Leu Ser Trp Leu Gln Gln Arg
    50                  55                  60

Pro Gly Gln Pro Leu Arg Leu Leu Phe Tyr Lys Ile Ser Asn Arg Phe
65                  70                  75                  80

Ser Gly Val Pro Asp Arg Phe Ser Gly Ser Gly Ala Gly Thr Asp Phe
                85                  90                  95

Thr Leu Ile Ile Asn Arg Val Glu Ala Glu Asp Val Gly Val Tyr Tyr
            100                 105                 110

Cys Met His Ala Thr Gln Phe Pro Ile Thr Phe Gly Gln Gly Thr Arg
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 9
<211> LENGTH: 1446
<212> TYPE: DNA
<213> ORGANISM: Homo Sapiens
<220> FEATURE:
<221> NAME/KEY: CDS
<222> LOCATION: (13)...(1440)

<400> SEQUENCE: 9
gaattcctca cc atg gag ttg ggg ctg tgc tgg ctt ttc ctt gtt gct ata       51
              Met Glu Leu Gly Leu Cys Trp Leu Phe Leu Val Ala Ile
                1               5                   10 tta gaa ggt gtc cag tgt ggg gtg cag ctg gtg gag tcg ggg gga ggc         99
Leu Glu Gly Val Gln Cys Gly Val Gln Leu Val Glu Ser Gly Gly Gly
    15                  20                  25 ttg gta cag cct ggg ggg tcc ctg aga ctc tcc tgt gca gcc tct gga        147
Leu Val Gln Pro Gly Gly Ser Leu Arg Leu Ser Cys Ala Ala Ser Gly
30                  35                  40                  45 ttc acc atc agt agg aac gac atg cac tgg gtc cgc caa gct aca gga        195

```
              Phe Thr Ile Ser Arg Asn Asp Met His Trp Val Arg Gln Ala Thr Gly
                           50                  55                  60 aaa ggt ctg gag tgg gtc tca gct att ggt act ggt ggt gac aca tac              243
Lys Gly Leu Glu Trp Val Ser Ala Ile Gly Thr Gly Gly Asp Thr Tyr
             65                  70                  75 tat cca ggc tcc gtg aag ggc cga ttc acc atc tcc aga gaa aat gcc              291
Tyr Pro Gly Ser Val Lys Gly Arg Phe Thr Ile Ser Arg Glu Asn Ala
         80                  85                  90 aag aac tcc ttg tat ctt caa atg aac agc ctg aga gcc ggg gac acg              339
Lys Asn Ser Leu Tyr Leu Gln Met Asn Ser Leu Arg Ala Gly Asp Thr
     95                 100                 105 gct gtg tat tac tgt gca aga ggt cac atg act acg ttt ggg gga ttt              387
Ala Val Tyr Tyr Cys Ala Arg Gly His Met Thr Thr Phe Gly Gly Phe
110                 115                 120                 125 atc gtt ata ggg aac ggt atg gac gtc tgg ggc caa ggg acc acg gtc              435
Ile Val Ile Gly Asn Gly Met Asp Val Trp Gly Gln Gly Thr Thr Val
                130                 135                 140 acc gtc agc tca gcc tcc acc aag ggc cca tcg gtc ttc ccc ctg gca              483
Thr Val Ser Ser Ala Ser Thr Lys Gly Pro Ser Val Phe Pro Leu Ala
            145                 150                 155 ccc tcc tcc aag agc acc tct ggg ggc aca gcg gcc ctg ggc tgc ctg              531
Pro Ser Ser Lys Ser Thr Ser Gly Gly Thr Ala Ala Leu Gly Cys Leu
        160                 165                 170 gtc aag gac tac ttc ccc gaa ccg gtg acg gtg tcg tgg aac tca ggc              579
Val Lys Asp Tyr Phe Pro Glu Pro Val Thr Val Ser Trp Asn Ser Gly
    175                 180                 185 gcc ctg acc agc ggc gtg cac acc ttc ccg gct gtc cta cag tcc tca              627
Ala Leu Thr Ser Gly Val His Thr Phe Pro Ala Val Leu Gln Ser Ser
190                 195                 200                 205 gga ctc tac tcc ctc agc agc gtg gtg acc gtg ccc tcc agc agc ttg              675
Gly Leu Tyr Ser Leu Ser Ser Val Val Thr Val Pro Ser Ser Ser Leu
                210                 215                 220 ggc acc cag acc tac atc tgc aac gtg aat cac aag ccc agc aac acc              723
Gly Thr Gln Thr Tyr Ile Cys Asn Val Asn His Lys Pro Ser Asn Thr
            225                 230                 235 aag gtg gac aag aaa gtt gag ccc aaa tct tgt gac aaa act cac aca              771
Lys Val Asp Lys Lys Val Glu Pro Lys Ser Cys Asp Lys Thr His Thr
        240                 245                 250 tgc cca ccg tgc cca gca cct gaa ctc ctg ggg gga ccg tca gtc ttc              819
Cys Pro Pro Cys Pro Ala Pro Glu Leu Leu Gly Gly Pro Ser Val Phe
    255                 260                 265 ctc ttc ccc cca aaa ccc aag gac acc ctc atg atc tcc cgg acc cct              867
Leu Phe Pro Pro Lys Pro Lys Asp Thr Leu Met Ile Ser Arg Thr Pro
270                 275                 280                 285 gag gtc aca tgc gtg gtg gtg gac gtg agc cac gaa gac cct gag gtc              915
Glu Val Thr Cys Val Val Val Asp Val Ser His Glu Asp Pro Glu Val
                290                 295                 300 aag ttc aac tgg tac gtg gac ggc gtg gag gtg cat aat gcc aag aca              963
Lys Phe Asn Trp Tyr Val Asp Gly Val Glu Val His Asn Ala Lys Thr
            305                 310                 315 aag ccg cgg gag gag cag tac aac agc acg tac cgt gtg gtc agc gtc             1011
Lys Pro Arg Glu Glu Gln Tyr Asn Ser Thr Tyr Arg Val Val Ser Val
        320                 325                 330 ctc acc gtc ctg cac cag gac tgg ctg aat ggc aag gag tac aag tgc             1059
Leu Thr Val Leu His Gln Asp Trp Leu Asn Gly Lys Glu Tyr Lys Cys
    335                 340                 345 aag gtc tcc aac aaa gcc ctc cca gcc ccc atc gag aaa acc atc tcc             1107
Lys Val Ser Asn Lys Ala Leu Pro Ala Pro Ile Glu Lys Thr Ile Ser
350                 355                 360                 365
```

```
aaa gcc aaa ggg cag ccc cga gaa cca cag gtg tac acc ctg ccc cca      1155
Lys Ala Lys Gly Gln Pro Arg Glu Pro Gln Val Tyr Thr Leu Pro Pro
            370                 375                 380 tcc cgg gat gag ctg acc aag aac cag gtc agc ctg acc tgc ctg gtc      1203
Ser Arg Asp Glu Leu Thr Lys Asn Gln Val Ser Leu Thr Cys Leu Val
            385                 390                 395 aaa ggc ttc tat ccc agc gac atc gcc gtg gag tgg gag agc aat ggg      1251
Lys Gly Phe Tyr Pro Ser Asp Ile Ala Val Glu Trp Glu Ser Asn Gly
            400                 405                 410 cag ccg gag aac aac tac aag acc acg cct ccc gtg ctg gac tcc gac      1299
Gln Pro Glu Asn Asn Tyr Lys Thr Thr Pro Pro Val Leu Asp Ser Asp
            415                 420                 425 ggc tcc ttc ttc ctc tac agc aag ctc acc gtg gac aag agc agg tgg      1347
Gly Ser Phe Phe Leu Tyr Ser Lys Leu Thr Val Asp Lys Ser Arg Trp
430                 435                 440                 445 cag cag ggg aac gtc ttc tca tgc tcc gtg atg cat gag gct ctg cac      1395
Gln Gln Gly Asn Val Phe Ser Cys Ser Val Met His Glu Ala Leu His
            450                 455                 460 aac cac tac acg cag aag agc ctc tcc ctg tct ccg ggt aaa taa          1440
Asn His Tyr Thr Gln Lys Ser Leu Ser Leu Ser Pro Gly Lys *
            465                 470                 475 tctaga                                                                1446

<210> SEQ ID NO 10
<211> LENGTH: 475
<212> TYPE: PRT
<213> ORGANISM: Homo Sapiens

<400> SEQUENCE: 10

Met Glu Leu Gly Leu Cys Trp Leu Phe Leu Val Ala Ile Leu Glu Gly
 1               5                  10                  15

Val Gln Cys Gly Val Gln Leu Val Glu Ser Gly Gly Gly Leu Val Gln
            20                  25                  30

Pro Gly Gly Ser Leu Arg Leu Ser Cys Ala Ala Ser Gly Phe Thr Ile
        35                  40                  45

Ser Arg Asn Asp Met His Trp Val Arg Gln Ala Thr Gly Lys Gly Leu
    50                  55                  60

Glu Trp Val Ser Ala Ile Gly Thr Gly Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Gly His Met Thr Thr Phe Gly Gly Phe Ile Val Ile
        115                 120                 125

Gly Asn Gly Met Asp Val Trp Gly Gln Gly Thr Thr Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220
```

```
Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
            245                 250                 255

Cys Pro Ala Pro Glu Leu Leu Gly Gly Pro Ser Val Phe Leu Phe Pro
        260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 11
<211> LENGTH: 725
<212> TYPE: DNA
<213> ORGANISM: Homo Sapiens
<220> FEATURE:
<221> NAME/KEY: CDS
<222> LOCATION: (15)...(719)

<400> SEQUENCE: 11
gcggccgcct cacc atg gaa acc cca gcg cag ctc ctc ttc ctc ctg cta        50
                Met Glu Thr Pro Ala Gln Leu Leu Phe Leu Leu Leu
                 1               5                  10 ctc tgg ctc cca gat acc act gga gaa ata gtg atg acg cag tct cca        98
Leu Trp Leu Pro Asp Thr Thr Gly Glu Ile Val Met Thr Gln Ser Pro
        15                  20                  25 gcc acc ctg tct gtg tct cca ggg gaa aga gcc acc ctc tcc tgc agg       146
Ala Thr Leu Ser Val Ser Pro Gly Glu Arg Ala Thr Leu Ser Cys Arg
            30                  35                  40 gcc agt cag agt gtt cgc agc aac tta gcc tgg tac cag cag aaa cct       194
Ala Ser Gln Ser Val Arg Ser Asn Leu Ala Trp Tyr Gln Gln Lys Pro
45                  50                  55                  60 ggc cag gct ccc agg ctc ctc atc tat ggt gca tcc acc agg gcc act       242
Gly Gln Ala Pro Arg Leu Leu Ile Tyr Gly Ala Ser Thr Arg Ala Thr
                65                  70                  75
```

```
ggt atc cca gcc agg ttc agt ggc agt ggg tct ggg aca gag ttt act       290
Gly Ile Pro Ala Arg Phe Ser Gly Ser Gly Ser Gly Thr Glu Phe Thr
            80                  85                  90 ctc acc atc agc agc ctg cag tct gaa gat ttt gca gtt tat tcc tgt       338
Leu Thr Ile Ser Ser Leu Gln Ser Glu Asp Phe Ala Val Tyr Ser Cys
        95                 100                 105 cag cag tat aat aac tgg ccg tgg acg ttc ggc caa ggg acc aag gtg       386
Gln Gln Tyr Asn Asn Trp Pro Trp Thr Phe Gly Gln Gly Thr Lys Val
    110                 115                 120 gaa atc aaa cgt acg gtg gct gca cca tct gtc ttc atc ttc ccg cca       434
Glu Ile Lys Arg Thr Val Ala Ala Pro Ser Val Phe Ile Phe Pro Pro
125                 130                 135                 140 tct gat gag cag ttg aaa tct gga act gcc tct gtt gtg tgc ctg ctg       482
Ser Asp Glu Gln Leu Lys Ser Gly Thr Ala Ser Val Val Cys Leu Leu
                145                 150                 155 aat aac ttc tat ccc aga gag gcc aaa gta cag tgg aag gtg gat aac       530
Asn Asn Phe Tyr Pro Arg Glu Ala Lys Val Gln Trp Lys Val Asp Asn
            160                 165                 170 gcc ctc caa tcg ggt aac tcc cag gag agt gtc aca gag cag gac agc       578
Ala Leu Gln Ser Gly Asn Ser Gln Glu Ser Val Thr Glu Gln Asp Ser
        175                 180                 185 aag gac agc acc tac agc ctc agc agc acc ctg acg ctg agc aaa gca       626
Lys Asp Ser Thr Tyr Ser Leu Ser Ser Thr Leu Thr Leu Ser Lys Ala
    190                 195                 200 gac tac gag aaa cac aaa gtc tac gcc tgc gaa gtc acc cat cag ggc       674
Asp Tyr Glu Lys His Lys Val Tyr Ala Cys Glu Val Thr His Gln Gly
205                 210                 215                 220 ctg agc tcg ccc gtc aca aag agc ttc aac agg gga gag tgt tag           719
Leu Ser Ser Pro Val Thr Lys Ser Phe Asn Arg Gly Glu Cys *
                225                 230 tctaga                                                                 725

<210> SEQ ID NO 12
<211> LENGTH: 234
<212> TYPE: PRT
<213> ORGANISM: Homo Sapiens

<400> SEQUENCE: 12

Met Glu Thr Pro Ala Gln Leu Leu Phe Leu Leu Leu Leu Trp Leu Pro
 1               5                  10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Arg Ser Asn Leu Ala Trp Tyr Gln Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Ser Cys Gln Gln Tyr Asn
            100                 105                 110

Asn Trp Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
```

```
                145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
                180                 185                 190
Tyr Ser Leu Ser Ser Thr Leu Thr Leu Ser Lys Ala Asp Tyr Glu Lys
                195                 200                 205
His Lys Val Tyr Ala Cys Glu Val Thr His Gln Gly Leu Ser Ser Pro
                210                 215                 220
Val Thr Lys Ser Phe Asn Arg Gly Glu Cys
225                 230

<210> SEQ ID NO 13
<211> LENGTH: 5
<212> TYPE: PRT
<213> ORGANISM: Artificial Sequence
<220> FEATURE:
<223> OTHER INFORMATION: AA 50-54 of SEQ ID NO 2

<400> SEQUENCE: 13

Ser Tyr Gly Met His
1               5

<210> SEQ ID NO 14
<211> LENGTH: 17
<212> TYPE: PRT
<213> ORGANISM: Artificial Sequence
<220> FEATURE:
<223> OTHER INFORMATION: AA 69-85 of SEQ ID NO 2

<400> SEQUENCE: 14

Val Ile Trp Tyr Asp Gly Asn Asn Lys Tyr Tyr Ala Asp Ser Val Lys
1               5                   10                  15
Gly

<210> SEQ ID NO 15
<211> LENGTH: 9
<212> TYPE: PRT
<213> ORGANISM: Artificial Sequence
<220> FEATURE:
<223> OTHER INFORMATION: AA 118-126 of SEQ ID NO 2

<400> SEQUENCE: 15

Thr Ser Gly Ile Ala Ala Phe Asp Tyr
1               5

<210> SEQ ID NO 16
<211> LENGTH: 5
<212> TYPE: PRT
<213> ORGANISM: Artificial Sequence
<220> FEATURE:
<223> OTHER INFORMATION: AA 50-54 of SEQ ID NO 6

<400> SEQUENCE: 16

Ser Tyr Asp Met His
1               5

<210> SEQ ID NO 17
<211> LENGTH: 16
<212> TYPE: PRT
<213> ORGANISM: Artificial Sequence
<220> FEATURE:
<223> OTHER INFORMATION: AA 69-84 of SEQ ID NO 6
```

```
<400> SEQUENCE: 17

Gly Ile Asp Ile Ala Gly Asp Thr Tyr Tyr Pro Gly Ser Val Lys Gly
1               5                   10                  15

<210> SEQ ID NO 18
<211> LENGTH: 9
<212> TYPE: PRT
<213> ORGANISM: Artificial Sequence
<220> FEATURE:
<223> OTHER INFORMATION: AA 117-125 of SEQ ID NO 6

<400> SEQUENCE: 18

Gly Asp Tyr Asp Gly Thr Phe Asp Tyr
1               5

<210> SEQ ID NO 19
<211> LENGTH: 5
<212> TYPE: PRT
<213> ORGANISM: Artificial Sequence
<220> FEATURE:
<223> OTHER INFORMATION: AA 50-54 of SEQ ID NO 10

<400> SEQUENCE: 19

Arg Asn Asp Met His
1               5

<210> SEQ ID NO 20
<211> LENGTH: 16
<212> TYPE: PRT
<213> ORGANISM: Artificial Sequence
<220> FEATURE:
<223> OTHER INFORMATION: AA 69-84 of SEQ ID NO 10

<400> SEQUENCE: 20

Ala Ile Gly Thr Gly Gly Asp Thr Tyr Tyr Pro Gly Ser Val Lys Gly
1               5                   10                  15

<210> SEQ ID NO 21
<211> LENGTH: 18
<212> TYPE: PRT
<213> ORGANISM: Artificial Sequence
<220> FEATURE:
<223> OTHER INFORMATION: AA 117-134 of SEQ ID NO 10

<400> SEQUENCE: 21

Gly His Met Thr Thr Phe Gly Gly Phe Ile Val Ile Gly Asn Gly Met
1               5                   10                  15

Asp Val

<210> SEQ ID NO 22
<211> LENGTH: 17
<212> TYPE: PRT
<213> ORGANISM: Artificial Sequence
<220> FEATURE:
<223> OTHER INFORMATION: AA 44-59 of SEQ ID NO 4

<400> SEQUENCE: 22

Lys Ser Ser Gln Ser Val Leu Tyr Asn Ser Asn Tyr Lys Asn Tyr Leu
1               5                   10                  15

Ala

<210> SEQ ID NO 23
<211> LENGTH: 7
<212> TYPE: PRT
<213> ORGANISM: Artificial Sequence
```

```
<220> FEATURE:
<223> OTHER INFORMATION: AA 76-82 of SEQ ID NO 4

<400> SEQUENCE: 23

Trp Ala Ser Thr Arg Glu Ser
1               5

<210> SEQ ID NO 24
<211> LENGTH: 9
<212> TYPE: PRT
<213> ORGANISM: Artificial Sequence
<220> FEATURE:
<223> OTHER INFORMATION: AA 115-123 of SEQ ID NO 4

<400> SEQUENCE: 24

Gln Gln Tyr Tyr Asn Thr Pro Leu Thr
1               5

<210> SEQ ID NO 25
<211> LENGTH: 16
<212> TYPE: PRT
<213> ORGANISM: Artificial Sequence
<220> FEATURE:
<223> OTHER INFORMATION: AA 44-59 of SEQ ID NO 8

<400> SEQUENCE: 25

Arg Ser Ser Gln Ser Leu Val His Ser Asp Gly Asn Thr Tyr Leu Ser
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: AA75-82 of SEQ ID NO 8

<400> SEQUENCE: 26

Lys Ile Ser Asn Arg Phe Ser
1               5

<210> SEQ ID NO 27
<211> LENGTH: 9
<212> TYPE: PRT
<213> ORGANISM: Artificial Sequence
<220> FEATURE:
<223> OTHER INFORMATION: AA114-122 of SEQ ID NO 8

<400> SEQUENCE: 27

Met His Ala Thr Gln Phe Pro Ile Thr
1               5

<210> SEQ ID NO 28
<211> LENGTH: 11
<212> TYPE: PRT
<213> ORGANISM: Artificial Sequence
<220> FEATURE:
<223> OTHER INFORMATION: AA 44-54 of SEQ ID NO 12

<400> SEQUENCE: 28

Arg Ala Ser Gln Ser Val Arg Ser Asn Leu Ala
1               5                   10

<210> SEQ ID NO 29
<211> LENGTH: 7
<212> TYPE: PRT
<213> ORGANISM: Artificial Sequence
<220> FEATURE:
```

```
<223> OTHER INFORMATION: AA 70-76 of SEQ ID NO 12

<400> SEQUENCE: 29

Gly Ala Ser Thr Arg Ala Thr
1               5

<210> SEQ ID NO 30
<211> LENGTH: 9
<212> TYPE: PRT
<213> ORGANISM: Artificial Sequence
<220> FEATURE:
<223> OTHER INFORMATION: AA 109-117 of SEQ ID NO 12

<400> SEQUENCE: 30

Gln Gln Tyr Asn Asn Trp Pro Trp Thr
1               5

<210> SEQ ID NO 31
<211> LENGTH: 39
<212> TYPE: DNA
<213> ORGANISM: Artificial Sequence
<220> FEATURE:
<223> OTHER INFORMATION: sc077 3'primer

<400> SEQUENCE: 31
aaaaagagag ctgagctgac ggtgaccagg gttccctgg                              39

<210> SEQ ID NO 32
<211> LENGTH: 39
<212> TYPE: DNA
<213> ORGANISM: Artificial Sequence
<220> FEATURE:
<223> OTHER INFORMATION: sc077 5'primer

<400> SEQUENCE: 32
aaaaactctg aattcctcac catggagttg ggactgtgt                              39

<210> SEQ ID NO 33
<211> LENGTH: 39
<212> TYPE: DNA
<213> ORGANISM: Artificial Sequence
<220> FEATURE:
<223> OTHER INFORMATION: sc077 3'primer

<400> SEQUENCE: 33
aaaaagagac gtacgtttga tctccacttt ggtccctcc                              39

<210> SEQ ID NO 34
<211> LENGTH: 44
<212> TYPE: DNA
<213> ORGANISM: Artificial Sequence
<220> FEATURE:
<223> OTHER INFORMATION: sc077 5'primer

<400> SEQUENCE: 34
aaaaactctg cggccgcctc accatggtgt tgcagaccca ggtc                        44

<210> SEQ ID NO 35
<211> LENGTH: 39
<212> TYPE: DNA
<213> ORGANISM: Artificial Sequence
<220> FEATURE:
<223> OTHER INFORMATION: sc189 3'primer

<400> SEQUENCE: 35
aaaaagagag ctgagctgac ggtgaccagg gttccctgg                              39
```

<210> SEQ ID NO 36
<211> LENGTH: 39
<212> TYPE: DNA
<213> ORGANISM: Artificial Sequence
<220> FEATURE:
<223> OTHER INFORMATION: sc189 5'primer

<400> SEQUENCE: 36
aaaaactctg aattcctcac catggaattt ggacttcgc                          39

<210> SEQ ID NO 37
<211> LENGTH: 39
<212> TYPE: DNA
<213> ORGANISM: Artificial Sequence
<220> FEATURE:
<223> OTHER INFORMATION: sc189 3'primer

<400> SEQUENCE: 37
aaaaagagac gtacgtttaa tctccagtcg tgtcccttg                          39

<210> SEQ ID NO 38
<211> LENGTH: 41
<212> TYPE: DNA
<213> ORGANISM: Artificial Sequence
<220> FEATURE:
<223> OTHER INFORMATION: sc189 5'primer

<400> SEQUENCE: 38
aaaaactctg cggccgcctc accatgaggg tccctgctca g                       41

<210> SEQ ID NO 39
<211> LENGTH: 39
<212> TYPE: DNA
<213> ORGANISM: Artificial Sequence
<220> FEATURE:
<223> OTHER INFORMATION: sc209 3'primer

<400> SEQUENCE: 39
aaaaagagag ctgagctgac ggtgaccgtg gtcccttgg                          39

<210> SEQ ID NO 40
<211> LENGTH: 39
<212> TYPE: DNA
<213> ORGANISM: Artificial Sequence
<220> FEATURE:
<223> OTHER INFORMATION: sc209 5'primer

<400> SEQUENCE: 40
aaaaactctg aattcctcac catggagttg gggctgtgc                          39

<210> SEQ ID NO 41
<211> LENGTH: 39
<212> TYPE: DNA
<213> ORGANISM: Artificial Sequence
<220> FEATURE:
<223> OTHER INFORMATION: sc209 3'primer

<400> SEQUENCE: 41
aaaaagagac gtacgtttga tttccacctt ggtcccttg                          39

<210> SEQ ID NO 42
<211> LENGTH: 41
<212> TYPE: DNA
<213> ORGANISM: Artificial Sequence
<220> FEATURE:

<223> OTHER INFORMATION: sc209 5'primer

<400> SEQUENCE: 42
aaaaactctg cggccgcctc accatggaaa ccccagcgca g    41

<210> SEQ ID NO 43
<211> LENGTH: 849
<212> TYPE: DNA
<213> ORGANISM: Homo Sapiens
<220> FEATURE:
<221> NAME/KEY: CDS
<222> LOCATION: (1)...(849)

<400> SEQUENCE: 43

| | | | | | | | | | | | | | | | | |
|---|---|---|---|---|---|---|---|---|---|---|---|---|---|---|---|---|
| atg | gct | tcc | ctg | ggg | cag | atc | ctc | ttc | tgg | agc | ata | att | agc | atc | atc | 48 |
| Met | Ala | Ser | Leu | Gly | Gln | Ile | Leu | Phe | Trp | Ser | Ile | Ile | Ser | Ile | Ile | |
| 1 | | | | 5 | | | | | 10 | | | | | 15 | | |
| att | att | ctg | gct | gga | gca | att | gca | ctc | atc | att | ggc | ttt | ggt | att | tca | 96 |
| Ile | Ile | Leu | Ala | Gly | Ala | Ile | Ala | Leu | Ile | Ile | Gly | Phe | Gly | Ile | Ser | |
| | | | 20 | | | | | 25 | | | | | 30 | | | |
| ggg | aga | cac | tcc | atc | aca | gtc | act | act | gtc | gcc | tca | gct | ggg | aac | att | 144 |
| Gly | Arg | His | Ser | Ile | Thr | Val | Thr | Thr | Val | Ala | Ser | Ala | Gly | Asn | Ile | |
| | | | 35 | | | | | 40 | | | | | 45 | | | |
| ggg | gag | gat | gga | atc | ctg | agc | tgc | act | ttt | gaa | cct | gac | atc | aaa | ctt | 192 |
| Gly | Glu | Asp | Gly | Ile | Leu | Ser | Cys | Thr | Phe | Glu | Pro | Asp | Ile | Lys | Leu | |
| | 50 | | | | | 55 | | | | | 60 | | | | | |
| tct | gat | atc | gtg | ata | caa | tgg | ctg | aag | gaa | ggt | gtt | tta | ggc | ttg | gtc | 240 |
| Ser | Asp | Ile | Val | Ile | Gln | Trp | Leu | Lys | Glu | Gly | Val | Leu | Gly | Leu | Val | |
| 65 | | | | | 70 | | | | | 75 | | | | | 80 | |
| cat | gag | ttc | aaa | gaa | ggc | aaa | gat | gag | ctg | tcg | gag | cag | gat | gaa | atg | 288 |
| His | Glu | Phe | Lys | Glu | Gly | Lys | Asp | Glu | Leu | Ser | Glu | Gln | Asp | Glu | Met | |
| | | | | 85 | | | | | 90 | | | | | 95 | | |
| ttc | aga | ggc | cgg | aca | gca | gtg | ttt | gct | gat | caa | gtg | ata | gtt | ggc | aat | 336 |
| Phe | Arg | Gly | Arg | Thr | Ala | Val | Phe | Ala | Asp | Gln | Val | Ile | Val | Gly | Asn | |
| | | | 100 | | | | | 105 | | | | | 110 | | | |
| gcc | tct | ttg | cgg | ctg | aaa | aac | gtg | caa | ctc | aca | gat | gct | ggc | acc | tac | 384 |
| Ala | Ser | Leu | Arg | Leu | Lys | Asn | Val | Gln | Leu | Thr | Asp | Ala | Gly | Thr | Tyr | |
| | | | | 115 | | | | | 120 | | | | | 125 | | |
| aaa | tgt | tat | atc | atc | act | tct | aaa | ggc | aag | ggg | aat | gct | aac | ctt | gag | 432 |
| Lys | Cys | Tyr | Ile | Ile | Thr | Ser | Lys | Gly | Lys | Gly | Asn | Ala | Asn | Leu | Glu | |
| | 130 | | | | | 135 | | | | | 140 | | | | | |
| tat | aaa | act | gga | gcc | ttc | agc | atg | ccg | gaa | gtg | aat | gtg | gac | tat | aat | 480 |
| Tyr | Lys | Thr | Gly | Ala | Phe | Ser | Met | Pro | Glu | Val | Asn | Val | Asp | Tyr | Asn | |
| 145 | | | | | 150 | | | | | 155 | | | | | 160 | |
| gcc | agc | tca | gag | acc | ttg | cgg | tgt | gag | gct | ccc | cga | tgg | ttc | ccc | cag | 528 |
| Ala | Ser | Ser | Glu | Thr | Leu | Arg | Cys | Glu | Ala | Pro | Arg | Trp | Phe | Pro | Gln | |
| | | | | 165 | | | | | 170 | | | | | 175 | | |
| ccc | aca | gtg | gtc | tgg | gca | tcc | caa | gtt | gac | cag | gga | gcc | aac | ttc | tcg | 576 |
| Pro | Thr | Val | Val | Trp | Ala | Ser | Gln | Val | Asp | Gln | Gly | Ala | Asn | Phe | Ser | |
| | | | 180 | | | | | 185 | | | | | 190 | | | |
| gaa | gtc | tcc | aat | acc | agc | ttt | gag | ctg | aac | tct | gag | aat | gtg | acc | atg | 624 |
| Glu | Val | Ser | Asn | Thr | Ser | Phe | Glu | Leu | Asn | Ser | Glu | Asn | Val | Thr | Met | |
| | | | | 195 | | | | | 200 | | | | | 205 | | |
| aag | gtt | gtg | tct | gtg | ctc | tac | aat | gtt | acg | atc | aac | aac | aca | tac | tcc | 672 |
| Lys | Val | Val | Ser | Val | Leu | Tyr | Asn | Val | Thr | Ile | Asn | Asn | Thr | Tyr | Ser | |
| | 210 | | | | | 215 | | | | | 220 | | | | | |
| tgt | atg | att | gaa | aat | gac | att | gcc | aaa | gca | aca | ggg | gat | atc | aaa | gtg | 720 |
| Cys | Met | Ile | Glu | Asn | Asp | Ile | Ala | Lys | Ala | Thr | Gly | Asp | Ile | Lys | Val | |
| 225 | | | | | 230 | | | | | 235 | | | | | 240 | |
| aca | gaa | tcg | gag | atc | aaa | agg | cgg | agt | cac | cta | cag | ctg | cta | aac | tca | 768 |
| Thr | Glu | Ser | Glu | Ile | Lys | Arg | Arg | Ser | His | Leu | Gln | Leu | Leu | Asn | Ser | |

```
                     245                 250                 255
aag gct tct ctg tgt gtc tct tct ttc ttt gcc atc agc tgg gca ctt      816
Lys Ala Ser Leu Cys Val Ser Ser Phe Phe Ala Ile Ser Trp Ala Leu
            260                 265                 270 ctg cct ctc agc cct tac ctg atg cta aaa taa                          849
Leu Pro Leu Ser Pro Tyr Leu Met Leu Lys *
        275                 280

<210> SEQ ID NO 44
<211> LENGTH: 282
<212> TYPE: PRT
<213> ORGANISM: Homo Sapiens

<400> SEQUENCE: 44

Met Ala Ser Leu Gly Gln Ile Leu Phe Trp Ser Ile Ile Ser Ile Ile
 1               5                  10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
 50                  55                  60

Ser Asp Ile Val Ile Gln Trp Leu Lys Glu Gly Val Leu Gly Leu Val
 65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280

<210> SEQ ID NO 45
<211> LENGTH: 235
<212> TYPE: PRT
<213> ORGANISM: Artificial Sequence
<220> FEATURE:
<223> OTHER INFORMATION: amino acids 32-257 of OV064 with 6HIS tag
``` sequence

<400> SEQUENCE: 45

Arg Gly Ser His His His His His Ser Gly Arg His Ser Ile Thr
1               5                   10                  15

Val Thr Thr Val Ala Ser Ala Gly Asn Ile Gly Glu Asp Gly Ile Leu
            20                  25                  30

Ser Cys Thr Phe Glu Pro Asp Ile Lys Leu Ser Asp Ile Val Ile Gln
        35                  40                  45

Trp Leu Lys Glu Gly Val Leu Gly Leu Val His Glu Phe Lys Glu Gly
    50                  55                  60

Lys Asp Glu Leu Ser Glu Gln Asp Glu Met Phe Arg Gly Arg Thr Ala
65                  70                  75                  80

Val Phe Ala Asp Gln Val Ile Val Gly Asn Ala Ser Leu Arg Leu Lys
                85                  90                  95

Asn Val Gln Leu Thr Asp Ala Gly Thr Tyr Lys Cys Tyr Ile Ile Thr
            100                 105                 110

Ser Lys Gly Lys Gly Asn Ala Asn Leu Glu Tyr Lys Thr Gly Ala Phe
        115                 120                 125

Ser Met Pro Glu Val Asn Val Asp Tyr Asn Ala Ser Ser Glu Thr Leu
    130                 135                 140

Arg Cys Glu Ala Pro Arg Trp Phe Pro Gln Pro Thr Val Val Trp Ala
145                 150                 155                 160

Ser Gln Val Asp Gln Gly Ala Asn Phe Ser Glu Val Ser Asn Thr Ser
                165                 170                 175

Phe Glu Leu Asn Ser Glu Asn Val Thr Met Lys Val Val Ser Val Leu
            180                 185                 190

Tyr Asn Val Thr Ile Asn Asn Thr Tyr Ser Cys Met Ile Glu Asn Asp
        195                 200                 205

Ile Ala Lys Ala Thr Gly Asp Ile Lys Val Thr Glu Ser Glu Ile Lys
    210                 215                 220

Arg Arg Ser His Leu Gln Leu Leu Asn Ser Lys
225                 230                 235

<210> SEQ ID NO 46
<211> LENGTH: 253
<212> TYPE: PRT
<213> ORGANISM: Artificial Sequence
<220> FEATURE:
<223> OTHER INFORMATION: amino acids 32-257 of OV064 with 6HIS and FLAG
      tag sequences

<400> SEQUENCE: 46

Asp Tyr Lys Asp Asp Asp Asp Lys Leu Ala Ala Ala Asn Ser Leu Ile
1               5                   10                  15

Ile Gly Phe Gly Ile Ser Gly Arg His Ser Ile Thr Val Thr Thr Val
            20                  25                  30

Ala Ser Ala Gly Asn Ile Gly Glu Asp Gly Ile Leu Ser Cys Thr Phe
        35                  40                  45

Glu Pro Asp Ile Lys Leu Ser Asp Ile Val Ile Gln Trp Leu Lys Glu
    50                  55                  60

Gly Val Leu Gly Leu Val His Glu Phe Lys Glu Gly Lys Asp Glu Leu
65                  70                  75                  80

Ser Glu Gln Asp Glu Met Phe Arg Gly Arg Thr Ala Val Phe Ala Asp
                85                  90                  95

Gln Val Ile Val Gly Asn Ala Ser Leu Arg Leu Lys Asn Val Gln Leu

-continued

```
                    100                 105                 110
Thr Asp Ala Gly Thr Tyr Lys Cys Tyr Ile Ile Thr Ser Lys Gly Lys
        115                 120                 125

Gly Asn Ala Asn Leu Glu Tyr Lys Thr Gly Ala Phe Ser Met Pro Glu
        130                 135                 140

Val Asn Val Asp Tyr Asn Ala Ser Ser Glu Thr Leu Arg Cys Glu Ala
145             150                 155                 160

Pro Arg Trp Phe Pro Gln Pro Thr Val Val Trp Ala Ser Gln Val Asp
                165             170                 175

Gln Gly Ala Asn Phe Ser Glu Val Ser Asn Thr Ser Phe Glu Leu Asn
            180                 185                 190

Ser Glu Asn Val Thr Met Lys Val Val Ser Val Leu Tyr Asn Val Thr
        195                 200                 205

Ile Asn Asn Thr Tyr Ser Cys Met Ile Glu Asn Asp Ile Ala Lys Ala
        210                 215                 220

Thr Gly Asp Ile Lys Val Thr Glu Ser Glu Ile Lys Arg Arg Ser His
225             230                 235                 240

Leu Gln Leu Leu Asn Ser Lys His His His His His
                245                 250
```

ANTIBODIES THAT BIND OV064 AND METHODS OF USE THEREFOR

RELATED APPLICATIONS

The present application is a Continuation of U.S. application Ser. No. 13/666,751 (published), filed Feb. 20, 2009 which is a Divisional of U.S. application Ser. No. 11/886,434 (published), filed Feb. 20, 2009, which is a National Stage of International Application Serial No. PCT/US06/08892, filed Mar. 10, 2006, and claims priority to U.S. Provisional Application Ser. No. 60/664,828, filed Mar. 24, 2005, the entire contents of which are incorporated herein by reference.

FIELD OF INVENTION

The present invention relates to antibodies and antigen binding fragments thereof which bind OV064, as well as therapeutic and diagnostic methods of use and compositions comprising the described antibodies and antigen binding fragments.

BACKGROUND OF THE INVENTION

Despite advances in the field of cancer therapy, tumor cell resistance to chemotherapeutic agents remains a significant problem in clinical oncology, as one of the main reasons many prevalent forms of human cancer resist effective chemotherapeutic intervention. Cell surface proteins expressed on cancer cells are presently being utilized for targeting specific cancer therapy in several tumor types. For example, Panorex® (edrocolomab), a monoclonal antibody which targets metastatic colon cancer, was the first monoclonal antibody approved for cancer treatment. Additional monoclonal antibody therapies have been approved in other cancers, for example, Herceptin® (trastuzumab), which is an antibody against the Her2/neu antigen, is currently being used to treat breast cancer (Finn and Slamon, *Cancer Chemother Biol Response Modif* 21: 223-233 (2003)). RituxanMabThera® (rituximab), which binds to the CD20 antigen, is being used to treat B-cell lymphomas (Multani and White, *Cancer Chemother Biol Response Modif* 21: 235-258 (2003)). Furthermore, several monoclonal antibody candidates presently undergoing clinical trials are showing great promise in colon and prostate cancers (Galsky et al., *Phase I trial of MLN2704 in patients with castrate-metastatic prostate cancer (CMPC).* ASCO Annual Meeting (2004); Hoff et al., *Oncology* (Huntingt) 18: 736-741; discussion 742, 745-736 (2004); Milowsky et al., *J Clin Oncol* 22: 2522-2531 (2004)). Many antibodies that are currently in development for cancer indications are unconjugated human or humanized IgG molecules that illicit the desired effect by inhibiting growth factor mediated proliferation or induce antibody dependent cell mediated cytotoxicity (ADCC) on cells expressing the targeted antigen. Any individual target of interest may not be appropriate for use in antibody targeted therapeutics or applicable for effective therapies in all cancers, however.

Additional approaches to antibody targeted therapeutics include utilization of tumor specific expression of a cell surface antigen to target toxins to the tumor site using monoclonal antibody-drug immunoconjugates (Payne, *Cancer Cell* 3: 207-212 (2003)). However, in common with chemotherapeutic approaches, immunotoxin therapy also suffers from significant drawbacks when applied to solid tumors. For example, antigen-negative or antigen-deficient cells can survive and repopulate the tumor or lead to further metastases. An additional reason for solid tumor resistance to antibody-based therapies is that the tumor mass is generally impermeable to macromolecular agents such as antibodies and immunotoxins (Burrows et al., *Cancer Res.* 52: 5954-62 (1992); Dvorak et al., *Cancer Cells.* 3: 77-85 (1991); Baxter and Jain, *Microvasc Res.* 41: 5-23 (1991)). Both the physical diffusion distances and the interstitial pressure within the tumor are significant limitations to this type of therapy. Therefore, solid tumors, which make up over 90% of all human cancers, have so far proven resistant to immunotoxin and antibody treatment. Further development and efficacy in clinical trials with useful antigens will be valuable advancements in identifying additional effective cancer therapies. Particularly useful are target antigens that have the ability to internalize and release the toxin inside the tumor cell and induce cell killing (Payne, *Cancer Cell* 3: 207-212 (2003)). Additionally, particularly useful targets would be primarily expressed in tumors, while lacking non-specific tissue expression. This approach has been shown to work very well in preclinical models and in vitro on cells expressing the antigen. To date, a couple of antibodies are in clinical development that are conjugated with the microtubule inhibitor maytansinoid, or DM1 (Tassone et al., *Cancer Res* 64: 4629-4636 (2004); Tolcher et al., *J Clin Oncol* 21: 211-222 (2003).

In view of the shortcoming of existing cancer therapies, there exists a need for identification of additional and improved modalities for ameliorating and treating cancers. The identification of additional effective targets is thus useful in conjunction with development of antibody targeted therapeutics and is certain to aid in the identification and generation of novel therapeutic regimens for cancer treatment.

DESCRIPTION OF THE FIGURE

FIG. 1 depicts the structure of the complete combination heavy and light chain immunoglobulin DNA cassette antibody expression vector pLKTOK58D.

DESCRIPTION OF THE INVENTION

The present invention relates to methods of using compositions comprising antibodies or antigen binding fragments which target OV064 for the treatment of cancers. In particular, the provided methods comprise treating a subject having a cancer by administering to a subject a sufficient amount of an immunoconjugate to treat the subject's cancer. The methods comprise utilizing an immunoconjugate which comprises an antibody or an antigen binding fragment and a cytotoxic moiety. The antibody or antigen binding fragment of the immunoconjugate binds specifically to an epitope on OV064 selected from any one of: an epitope comprising amino acid residues selected from amino acid residues 167-176 of OV064, an epitope comprising amino acid residues selected from amino acid residues 177-181 of OV064, an epitope comprising amino acid residues selected from amino acid residues 238-257 of OV064, an epitope recognized by sc77, an epitope recognized by sc189, an epitope recognized by sc209, an epitope recognized by 4G10, an epitope recognized by 3A4, or an epitope recognized by 2F3. Binding of the immunoconjugate to a cell expressing OV064 induces internalization of the immunoconjugate and OV064 into the cell. The cytotoxic moiety of the immunoconjugate can comprise a radioisotope, a therapeutic agent, or a tumor-activated prodrug. In some aspects, the cytotoxic moiety is a therapeutic agent comprising a maytansine, an auristatin, a dolastatin, a duocarmycin, a cryptophycin, a taxane, a DNA alkylating agent, calicheamicin, or a derivative of any one of these.

The invention also relates to antibodies and antigen-binding fragments of antibodies which bind specifically to the extracellular domain of OV064 sufficient to induce internalization of the antibody or the antigen binding fragment thereof and OV064 into the cell. The antibody or the antigen binding fragments of the invention bind specifically to an epitope on OV064 selected from any one of: an epitope comprising amino acid residues selected from amino acid residues 167-176 of OV064, an epitope comprising amino acid residues selected from amino acid residues 177-181 of OV064, an epitope comprising amino acid residues selected from amino acid residues 238-257 of OV064, an epitope recognized by sc77, an epitope recognized by sc189, an epitope recognized by sc209, an epitope recognized by 4G10, an epitope recognized by 3A4, or an epitope recognized by 2F3. Further provided are antibodies or antigen binding fragments which bind specifically to an epitope comprising amino acid residues 67-76 of OV064, or an epitope recognized by 8G5. Human and modified antibodies and antigen binding fragments thereof are provided. For example, humanized and chimeric antibodies, and antigen binding fragments of the foregoing are encompassed in the invention.

The invention provides immunoconjugates comprising an antibody or antigen-binding fragment thereof coupled to a cytotoxic moiety that has the ability to kill cells expressing OV064. The antibody or the antigen binding fragment of the immunoconjugates bind specifically to the extracellular domain of OV064 sufficient to induce internalization of the antibody or the antigen binding fragment thereof and OV064 into the cell. The antibody or the antigen binding fragments of the immunoconjugates bind specifically to an epitope on OV064 selected from any one of: an epitope comprising amino acid residues selected from amino acid residues 167-176 of OV064, an epitope comprising amino acid residues selected from amino acid residues 177-181 of OV064, an epitope comprising amino acid residues selected from amino acid residues 238-257 of OV064, an epitope recognized by sc77, an epitope recognized by sc189, an epitope recognized by sc209, an epitope recognized by 4G10, an epitope recognized by 3A4, or an epitope recognized by 2F3. The provided immunoconjugates may comprise any one of the antibodies or antigen binding fragments of the invention. The cytotoxic moiety of the immunoconjugates can comprise a radioisotope, a therapeutic agent, or a tumor-activated prodrug. In one aspect, the immunoconjugate comprising an antibody or antigen-binding fragment thereof of the invention can reduce tumor-cell induced immune suppression of tumor cells expressing OV064. In an additional aspect, the immunoconjugate comprising an antibody or antigen-binding fragment thereof can inhibit tumor growth. In some aspects, the immunoconjugate comprises an antibody or an antigen binding fragment of the invention conjugated to a matansine, an auristatin, a dolastatin, a duocarmycin, a cryptophicin, a taxol, a DNA alkylating agent, or a calicheamicin or a derivative of any of the foregoing. In certain aspects, maytasines of the immunoconjugates of the invention comprise DM1 or DM4 conjugated to an antibody or an antigen binding fragment of the invention.

In still additional aspects, the antibody or antigen-binding fragment can inhibit OV064-mediated cell signaling of a first cell expressing an OV064 by inhibiting interaction with a second cell bearing a ligand of OV064, such as T-cells. In some aspects, the antibody or antigen-binding fragment competitively inhibits binding of one or more of the antibodies provided and described herein (e.g., mAb 4G10, mAb 3A4, mAb 2F3, mAb sc77, mAb sc189, and/or mAb sc209).

In particular, one embodiment of the invention provides a method of treating cancer in a subject. The method comprises administering to a subject an immunoconjugate in an effective amount so as to treat the cancer. The methods comprise utilizing an immunoconjugate which comprises an antibody or an antigen binding fragment and a cytotoxic moiety. The antibody or the antigen binding fragment of the immunoconjugate binds specifically to an epitope on OV064 selected from any one of: an epitope comprising amino acid residues selected from amino acid residues 167-176 of OV064, an epitope comprising amino acid residues selected from amino acid residues 177-181 of OV064, an epitope comprising amino acid residues selected from amino acid residues 238-257 of OV064, an epitope recognized by sc77, an epitope recognized by sc189, an epitope recognized by sc209, an epitope recognized by 4G10, an epitope recognized by 3A4, or an epitope recognized by 2F3. Binding of the immunoconjugate to a cell expressing OV064 induces internalization of the immunoconjugate and OV064 into the cell, and administration of the effective amount of immunoconjugate, is sufficient to reduce or inhibit the growth of the subject's tumor.

In certain embodiments, the cytotoxic moiety of the immunoconjugate comprises a radioisotope, a therapeutic agent, or a tumor activated pro-drug. Where the cytotoxic moiety is a therapeutic agent, the agent can comprise a maytansine, an auristatin, a duocarmycin, a dolastatin, a cryptophicin, a taxol, a DNA alkylating agent, or calicheamicin, or a derivative of any of the foregoing. In some aspects the therapeutic agent is a maytansine which is DM1 or DM4.

The invention also relates to methods of inhibiting OV064 mediated cell signaling resulting from interaction of a cell expressing OV064 with an OV064 receptor. For example, the method comprises contacting a cell with a sufficient amount of an antibody or an antigen-binding fragment of the invention which binds specifically to an epitope on OV064 selected from any one of: an epitope comprising amino acid residues selected from amino acid residues 167-176 of OV064, an epitope comprising amino acid residues selected from amino acid residues 177-181 of OV064, an epitope comprising amino acid residues selected from amino acid residues 238-257 of OV064, an epitope recognized by sc77, an epitope recognized by sc189, an epitope recognized by sc209, an epitope recognized by 4G10, an epitope recognized by 3A4, or an epitope recognized by 2F3. Binding of the antibody or antigen binding fragment thereof to a cell expressing OV064 induces internalization of the antibody and OV064 into the cell, and reduces the amount of OV064 available for interaction with the OV064 receptor. The method thereby results in inhibiting OV064 mediated cell signaling resulting from interaction of a cell expressing OV064 with an OV064 receptor. Provided methods of the invention also include a method of killing a cell expressing OV064. For example, an antibody or an antigen binding fragment of the invention which is an immunoconjugate comprising a cytotoxic moiety may be used in the method. Alternatively, an antibody or an antigen binding fragment which is bound to a secondary antibody or antigen binding fragment which comprises an immunoconjugate coupled to a cytotoxic moiety may be used in the method. For example, the method comprises contacting a cell expressing OV064 with an effective amount of an antibody or an antigen binding fragment of the invention which binds the extracellular domain of OV064, and which is an immunoconjugate comprising a cytotoxic moiety or is bound to a secondary antibody which is an immunoconjugate comprising a cytotoxic moiety. Binding of the antibody or antigen binding fragment to the cell induces internalization of the antibody or antigen binding fragment and OV064 into the cell, and internalization is sufficient to deliver toxic payload into the cell, thereby killing the cell. The methods of either inhibition of OV064 cell signaling, or killing a OV064 expressing cell are useful in cells expressing OV064. For example, cells include ES-2 ovarian carcinoma cells, SKBR-3 breast carcinoma cells, ZR75-1 cells, OVCAR3 cells, MDA-MB-468 cells, MCF-7 cells, DLD1 cells, fresh or frozen ovarian tumor cells, or cells comprising a recombinant nucleic acid encoding OV064 or a portion thereof. In certain aspects the OV064 receptor is BTLA. The method of inhibition of signaling, or the method of killing cells expressing OV064 may be carries out in vitro, in vivo, ex vivo, or in situ.

The methods comprise use of an antibody or antigen binding fragment which binds the extracellular domain of OV064, as well as use of immunoconjugates comprising an antibody or an antigen binding fragment thereof which binds the extracellular domain of OV064. Thus, provided are antibodies or antigen binding fragments thereof for use in the compositions (e.g., immunoconjugates) and in the methods provided herein. The invention encompasses the provided antibodies or antigen binding fragments thereof, immunoconjugates of the provided antibodies or antigen binding fragments thereof, as well as uses of any of the provided antibodies or antigen binding fragments, or immunoconjugates comprising the antibodies or the antigen binding fragments in conjunction with the described methods. Use of the provided antibodies or antigen binding fragments or any combination of the provided antibodies or antigen binding fragments in compositions and/or methods of the invention provided is intended. Provided antibodies or antigen binding fragments include an antibody or antigen binding fragment thereof which binds specifically to an epitope on OV064 selected from any one of: an epitope comprising amino acid residues selected from amino acid residues 167-176 of OV064, an epitope comprising amino acid residues selected from amino acid residues 177-181 of OV064, an epitope comprising amino acid residues selected from amino acid residues 238-257 of OV064, an epitope recognized by sc77, an epitope recognized by sc189, an epitope recognized by sc209, an epitope recognized by 4G10, an epitope recognized by 3A4, or an epitope recognized by 2F3. Binding of the antibody or the antigen binding fragment to a cell expressing OV064 induces internalization of the antibody or the antigen binding fragment and OV064 into the cell. Also included in the invention is an antibody or antigen binding fragment which binds specifically to an epitope on OV064 which is an epitope recognized by 8G5, or an epitope comprising amino acid residues selected from amino acid residues 67-71 of OV064.

Provided antibody or antigen binding fragments compete with one or more of sc77, sc189, sc209, 4G10, 3A4, or 2F3 for binding to OV064. Additional human antibody or antigen binding fragments compete with 8G5 for binding to OV064.

In certain embodiments, the antibody or antigen binding fragment thereof comprises the ability to kill cells expressing OV064 when coupled to a cytotoxic moiety. In other embodiments, the antibody or antigen-binding fragment comprises the ability to reduce tumor-cell induced immune suppression of tumor cells expressing OV064.

In some embodiments the antibody or the antigen binding fragment is a human antibody or antigen binding fragment thereof.

In additional embodiments, the antibody may be a modified antibody or an antigen binding fragment thereof. Where the antibody or the antigen binding fragment is modified, it may be a modified rodent, rabbit, or human antibody or antigen binding fragment. In one aspect, the rodent antibody or antigen binding fragment is a murine antibody or antigen binding fragment. In certain aspects, the modified antibody or antigen binding fragment comprises a CDR-grafted antibody, a humanized antibody, or a chimeric antibody, or an antigen binding fragment or fragments of the foregoing. Certain aspects include a humanized or chimeric antibody or an antigen-binding fragment thereof having binding specificity for an epitope on OV064 selected from any one of: an epitope comprising amino acid residues selected from amino acid residues 167-176 of OV064, an epitope comprising amino acid residues selected from amino acid residues 177-181 of OV064, an epitope comprising amino acid residues selected from amino acid residues 238-257 of OV064, an epitope recognized by sc77, an epitope recognized by sc189, an epitope recognized by sc209, an epitope recognized by 4G10, an epitope recognized by 3A4, or an epitope recognized by 2F3. In some embodiments, the antibody or antigen binding fragment thereof comprises a light chain, wherein the light chain comprises one, two, or three complementarity determining region derived from monoclonal antibody 4G10, 3A4, or 2F3. In additional aspects the light chain comprises one, two, or three complementarity determining region derived from monoclonal antibody 4G10, 3A4, or 2F3 and the framework region sequence is derived from a light chain of human origin. In other embodiments, the heavy chain comprises one, two, or three complementarity determining region derived from monoclonal antibody 4G10, 3A4, or 2F3. In additional aspects, the heavy chain comprises one, two, or three complementarity determining region derived from monoclonal antibody 4G10, 3A4, or 2F3 and the framework region derived from a heavy chain of human origin. In some aspects, the humanized antibody competes with murine antibody 4G10, 3A4, or 2F3 for binding to OV064. In some aspects the light chain comprises at least one complementarity determining region derived from monoclonal antibody 4G10, 3A4, or 2F3 and the heavy chain comprises at least one complementarity determining region derived from monoclonal antibody 4G10, 3A4, or 2F3. In additional aspects, the humanized antibody or antigen-binding fragment comprises all three complementarity determining regions derived from the light chain of monoclonal antibody 4G10, 3A4, or 2F3; and the heavy chain comprises all three complementarity determining regions derived from the heavy chain of monoclonal antibody 4G10, 3A4, or 2F3.

In still other embodiments, a humanized antibody competes with murine antibody 8G5 for binding to OV064. In additional aspects the humanized antibody or the antigen binding fragment comprises one, two or three complementarity determining regions derived from the heavy chain of monoclonal antibody 8G5 and one, two, or three complementarity determining regions derived from the light chain of monoclonal antibody 8G5. In some aspects the light chain comprises at least one complementarity determining region derived from monoclonal antibody 8G5 and the heavy chain comprises at least one complementarity determining region derived from monoclonal antibody 8G5. In additional aspects, the humanized antibody or antigen-binding fragment comprises all three complementarity determining regions derived from the light chain of monoclonal antibody 8G5; and the heavy chain comprises all three complementarity determining regions derived from the heavy chain of monoclonal antibody 8G5

In certain embodiments, an antibody or modified antibody has one or more complementarity determining regions from the human monoclonal antibody sc77, sc189, or sc209. In additional embodiments, the antibody or antigen binding fragment thereof competes for binding with the same epitope as monoclonal antibody sc77, sc189, or sc209, and/or competes for binding the same epitope as murine monoclonal antibody 4G10, 3A4, or 2F3.

For example, in specific embodiments the antibody or antigen-binding fragment comprises one, two or three heavy chain complementarity determining region (HCDR1, HCDR2 and/or HCDR3) of the monoclonal antibody sc77. The complementarity determining region may comprise an amino acid sequence of: HCDR1 (e.g., SEQ ID NO: 13; SEQ ID NO: 13 wherein optionally one or two amino acids are conservatively substituted); HCDR2 (e.g., SEQ ID NO: 14; SEQ ID NO: 14 wherein optionally one or two amino acids are conservatively substituted); or HCDR3 (e.g., SEQ ID NO: 15 or SEQ ID NO: 15 wherein optionally one or two amino acids are conservatively substituted). In certain aspects, the antibody or antigen-binding fragment comprises all three heavy chain complementarity determining regions (HCDR1 (e.g., SEQ ID NO: 13; SEQ ID NO: 13 wherein optionally one or two amino acids are conservatively substituted); HCDR2 (e.g., SEQ ID NO: 14; SEQ ID NO: 14 wherein optionally one or two amino acids are conservatively substituted); and HCDR3 (e.g., SEQ ID NO: 15 or SEQ ID NO: 15 wherein optionally one or two amino acids are conservatively substituted)) of the monoclonal antibody sc77. In some embodiments, the heavy chain sequence comprises human heavy chain constant region sequence of human isotype IgG1 or IgG2.

In other embodiments, the antibody or the antigen binding fragment may comprise one, two or three light chain complementarity determining region (LCDR1, LCDR2 and/or LCDR3) of the monoclonal antibody sc77. The complementarity determining region may comprise an amino acid sequence of: LCDR1 (e.g., SEQ ID NO: 22, SEQ ID NO: 22 wherein optionally one or two amino acids are conservatively substituted); LCDR2 (e.g., SEQ ID NO: 23, SEQ ID NO: 23 wherein one or two amino acids are conservatively substituted); or LCDR3 (e.g., SEQ ID NO: 24, SEQ ID NO: 24 wherein optionally one or two amino acids are conservatively substituted). In certain aspects, the antibody or the antigen binding fragment comprises all three light chain complementarity determining regions (LCDR1 (e.g., SEQ ID NO: 22, SEQ ID NO: 22 wherein optionally one or two amino acids are conservatively substituted); LCDR2 (e.g., SEQ ID NO: 23, SEQ ID NO: 23 wherein one or two amino acids are conservatively substituted); and LCDR3 (e.g., SEQ ID NO: 24, SEQ ID NO: 24 wherein optionally one or two amino acids are conservatively substituted)) of the monoclonal antibody sc77.

In certain aspects, the antibody or the antigen binding fragment comprises one, two or three heavy chain complementarity determining region (HCDR1 (e.g., SEQ ID NO: 13; SEQ ID NO: 13 wherein optionally one or two amino acids are conservatively substituted); HCDR2 (e.g., SEQ ID NO: 14; SEQ ID NO: 14 wherein optionally one or two amino acids are conservatively substituted); and/or HCDR3 (e.g., SEQ ID NO: 15 or SEQ ID NO: 15 wherein optionally one or two amino acids are conservatively substituted)) of the monoclonal antibody sc77; and one, two or three light chain complementarity determining region (LCDR1 (e.g., SEQ ID NO: 22, SEQ ID NO: 22 wherein optionally one or two amino acids are conservatively substituted); LCDR2 (e.g., SEQ ID NO: 23, SEQ ID NO: 23 wherein one or two amino acids are conservatively substituted); or LCDR3 (e.g., SEQ ID NO: 24, SEQ ID NO: 24 wherein optionally one or two amino acids are conservatively substituted)) of the monoclonal antibody sc77. In additional aspects, the antibody or the antigen binding fragment comprises all three heavy chain complementarity determining regions (HCDR1 (e.g., SEQ ID NO: 13; SEQ ID NO: 13 wherein optionally one or two amino acids are conservatively substituted); HCDR2 (e.g., SEQ ID NO: 14; SEQ ID NO: 14 wherein optionally one or two amino acids are conservatively substituted); and HCDR3 (e.g., SEQ ID NO: 15 or SEQ ID NO: 15 wherein optionally one or two amino acids are conservatively substituted)) of the monoclonal antibody sc77; and all three light chain complementarity determining regions (LCDR1 (e.g., SEQ ID NO: 22, SEQ ID NO: 22 wherein optionally one or two amino acids are conservatively substituted); LCDR2 (e.g., SEQ ID NO: 23, SEQ ID NO: 23 wherein one or two amino acids are conservatively substituted); or LCDR3 (e.g., SEQ ID NO: 24, SEQ ID NO: 24 wherein optionally one or two amino acids are conservatively substituted)) of the monoclonal antibody sc77. In some embodiments, the heavy chain sequence further comprises human heavy chain constant region sequence of human isotype IgG1 or IgG2.

In additional aspects, the antibody or the antigen binding fragment comprises an amino acid sequence shown as SEQ ID NO:4, an amino acid sequence of the light chain variable region amino acid sequence of the antibody encoded by the purified DNA having ATCC Accession Number PTA-6294, or the amino acid encoded by the nucleotide sequence shown as nucleic acid residues 15-737 of SEQ ID NO:3.

In other additional aspects, the antibody or the antigen binding fragment comprises an amino acid sequence shown as SEQ ID NO:2, an amino acid sequence of the heavy chain variable region amino acid sequence of the antibody encoded by the purified DNA having ATCC Accession Number PTA-6294, or the amino acid sequence encoded by the nucleotide sequence shown as nucleic acid residues 13-1416 of SEQ ID NO:1.

In still other aspects, the antibody or the antigen binding fragment comprises a light chain variable region comprising the amino acid sequence shown as SEQ ID NO:4, or the light chain variable region amino acid sequence of the antibody encoded by the purified DNA having ATCC Accession Number PTA-6294; and a heavy chain variable region comprising the amino acid sequence shown as SEQ ID NO:2, or the heavy chain variable region amino acid sequence of the antibody encoded by the purified DNA having ATCC Accession Number PTA-6294. In further aspects, the antibody or antigen binding fragment comprises two heavy and two light chains.

In some embodiments, the human antibody or antigen binding fragment is sc77, or a fragment thereof.

In another example, the antibody or antigen-binding fragment comprises one, two, or three heavy chain complementarity determining region (HCDR1, HCDR2 and/or HCDR3) of the monoclonal antibody sc189. The complementarity determining region may comprise an amino acid sequence of: HCDR1 (e.g., SEQ ID NO: 16, SEQ ID NO: 16 wherein optionally one or two amino acids are conservatively substituted); HCDR2 (e.g., SEQ ID NO: 17, SEQ ID NO: 17 wherein optionally one or two amino acids are conservatively substituted); or HCDR3 (e.g., SEQ ID NO: 18, SEQ ID NO: 18 wherein optionally one or two amino acids are conservatively substituted). In certain aspects, the antibody or antigen-binding fragment comprises all three heavy chain complementarity determining regions (HCDR1 (e.g., SEQ ID NO: 16, SEQ ID NO: 16 wherein optionally one or two amino acids are conservatively substituted); HCDR2 (e.g., SEQ ID NO: 17, SEQ ID NO: 17 wherein optionally one or two amino acids are conservatively substituted); and HCDR3 (e.g., SEQ ID NO: 18, SEQ ID NO: 18 wherein optionally one or two amino acids are conservatively substituted)) of the monoclonal antibody sc189. In some embodiments, the heavy chain sequence further comprises human heavy chain constant region sequence of human isotype IgG1 or IgG2.

In other embodiments, the antibody or antigen binding fragment may comprise one, two, or three light chain complementarity determining region (LCDR1, LCDR2 and/or LCDR3) of the monoclonal antibody sc189. The complementarity determining region may comprise an amino acid sequence of: LCDR1 (e.g., SEQ ID NO: 25, SEQ ID NO: 25 wherein optionally one or two amino acids are conservatively substituted); LCDR2 (e.g., SEQ ID NO: 26, SEQ ID NO: 26 wherein optionally one or two amino acids are conservatively substituted); or LCDR3 (e.g., SEQ ID NO: 27, SEQ ID NO: 27 wherein optionally one or two amino acids are conservatively substituted). In certain aspects, the antibody or antigen binding fragment may comprise all three light chain complementarity determining regions (LCDR1 (e.g., SEQ ID NO: 25, SEQ ID NO: 25 wherein optionally one or two amino acids are conservatively substituted); LCDR2 (e.g., SEQ ID NO: 26, SEQ ID NO: 26 wherein optionally one or two amino acids are conservatively substituted); and LCDR3 (e.g., SEQ ID NO: 27, SEQ ID NO: 27 wherein optionally one or two amino acids are conservatively substituted)) of the monoclonal antibody sc189.

In certain aspects, the antibody or antigen binding fragment comprises one, two, or three heavy chain complementarity determining region (HCDR1 (e.g., SEQ ID NO: 16, SEQ ID NO: 16 wherein optionally one or two amino acids are conservatively substituted); HCDR2 (e.g., SEQ ID NO: 17, SEQ ID NO: 17 wherein optionally one or two amino acids are conservatively substituted); and/or HCDR3 (e.g., SEQ ID NO: 18, SEQ ID NO: 18 wherein optionally one or two amino acids are conservatively substituted)) of the monoclonal antibody sc189; and one, two, or three light chain complementarity determining region (LCDR1 (e.g., SEQ ID NO: 25, SEQ ID NO: 25 wherein optionally one or two amino acids are conservatively substituted); LCDR2 (e.g., SEQ ID NO: 26, SEQ ID NO: 26 wherein optionally one or two amino acids are conservatively substituted); and/or LCDR3 (e.g., SEQ ID NO: 27, SEQ ID NO: 27 wherein optionally one or two amino acids are conservatively substituted)) of the monoclonal antibody sc189. In additional aspects, the antibody or antigen binding fragment comprises all three heavy chain complementarity determining regions (HCDR1 (e.g., SEQ ID NO: 16, SEQ ID NO: 16 wherein optionally one or two amino acids are conservatively substituted); HCDR2 (e.g., SEQ ID NO: 17, SEQ ID NO: 17 wherein optionally one or two amino acids are conservatively substituted); and HCDR3 (e.g., SEQ ID NO: 18, SEQ ID NO: 18 wherein optionally one or two amino acids are conservatively substituted)) of the monoclonal antibody sc189; and all three light chain complementarity determining regions (LCDR1 (e.g., SEQ ID NO: 25, SEQ ID NO: 25 wherein optionally one or two amino acids are conservatively substituted); LCDR2 (e.g., SEQ ID NO: 26, SEQ ID NO: 26 wherein optionally one or two amino acids are conservatively substituted); and LCDR3 (e.g., SEQ ID NO: 27, SEQ ID NO: 27 wherein optionally one or two amino acids are conservatively substituted)) of the monoclonal antibody sc189. In some embodiments, the heavy chain sequence further comprises human heavy chain constant region sequence of human isotype IgG1 or IgG2.

In additional aspects, the antibody or antigen binding fragment comprises and amino acid sequence shown as SEQ ID NO: 8, an amino acid sequence of the light chain variable region amino acid sequence of the antibody encoded by the purified DNA having ATCC Accession Number PTA-6295, or the amino encoded by the nucleotide sequence shown as nucleic acid residues 15-734 of SEQ ID NO:7.

In other additional aspects, the antibody or antigen binding fragment thereof comprises an amino acid sequence shown as SEQ ID NO:6, an amino acid sequence of the heavy chain variable region amino acid sequence of the antibody encoded by the purified DNA having ATCC Accession Number PTA-6295, or the amino acid sequence encoded by the nucleotide sequence shown as nucleic acid residues 13-1413 of SEQ ID NO:5.

In still other aspects, the antibody or antigen binding fragment comprises a light chain variable region comprising the amino acid sequence shown as SEQ ID NO:8, or the light chain variable region amino acid sequence of the antibody encoded by the purified DNA having ATCC Accession Number PTA-6295; and a heavy chain variable region comprising the amino acid sequence shown as SEQ ID NO:6, or the heavy chain variable region amino acid sequence of the antibody encoded by the purified DNA having ATCC Accession Number PTA-6295. In certain aspects antibody or antigen binding fragment comprises two heavy and two light chains.

In other embodiments, the human antibody or antigen binding fragment is sc189, or a fragment thereof.

Still further provided are specific embodiments wherein the antibody or antigen-binding fragment comprises one, two, or three heavy chain complementarity determining region (HCDR1, HCDR2 and/or HCDR3) of the monoclonal antibody sc209. The complementarity determining region may comprise an amino acid sequence of: HCDR1 (e.g., SEQ ID NO: 19, SEQ ID NO: 19 wherein optionally one or two amino acids are conservatively substituted); HCDR2 (e.g., SEQ ID NO: 20, SEQ ID NO: 20 wherein optionally one or two amino acids are conservatively substituted); or HCDR3 (e.g., SEQ ID NO: 21, SEQ ID NO: 21 wherein optionally one or two amino acids are conservatively substituted). In certain aspects, the antibody or antigen-binding fragment comprises all three heavy chain complementarity determining regions (HCDR1 (e.g., SEQ ID NO: 19, SEQ ID NO: 19 wherein optionally one or two amino acids are conservatively substituted); HCDR2 (e.g., SEQ ID NO: 20, SEQ ID NO: 20 wherein optionally one or two amino acids are conservatively substituted); and HCDR3 (e.g., SEQ ID NO: 21, SEQ ID NO: 21 wherein optionally one or two amino acids are conservatively substituted)) of the monoclonal antibody sc209. In some embodiments, the heavy chain sequence comprises human heavy chain constant region sequence of human isotype IgG1 or IgG2.

In other embodiments, the antibody or antigen binding fragment may comprise one, two or three light chain complementarity determining region (LCDR1, LCDR2 and/or LCDR3) of the monoclonal antibody sc209. The complementarity determining region may comprise an amino acid sequence of: LCDR1, (e.g., SEQ ID NO: 28 or SEQ ID NO: 28 wherein optionally one or two amino acids are conservatively substituted); LCDR2, (e.g., SEQ ID NO: 29 or SEQ ID NO: 29 wherein optionally one or two amino acids are conservatively substituted); or LCDR3, (e.g., SEQ ID NO: 30 or SEQ ID NO: 30 wherein optionally one or two amino acids are conservatively substituted). In certain aspects, the antibody or antigen binding fragment may comprise all three light chain complementarity determining regions (LCDR1, (e.g., SEQ ID NO: 28 or SEQ ID NO: 28 wherein optionally one or two amino acids are conservatively substituted); LCDR2, (e.g., SEQ ID NO: 29 or SEQ ID NO: 29 wherein optionally one or two amino acids are conservatively substituted); and LCDR3, (e.g., SEQ ID NO: 30 or SEQ ID NO: 30 wherein optionally one or two amino acids are conservatively substituted)) of the monoclonal antibody sc209.

In certain aspects, the antibody or antigen binding fragment comprises one, two or three heavy chain complementarity determining region (HCDR1 (e.g., SEQ ID NO: 19, SEQ ID NO: 19 wherein optionally one or two amino acids are conservatively substituted); HCDR2 (e.g., SEQ ID NO: 20, SEQ ID NO: 20 wherein optionally one or two amino acids are conservatively substituted); and/or HCDR3 (e.g., SEQ ID NO: 21, SEQ ID NO: 21 wherein optionally one or two amino acids are conservatively substituted)) of the monoclonal antibody sc209; and one, two, or three chain complementarity determining region (LCDR1, (e.g., SEQ ID NO: 28 or SEQ ID NO: 28 wherein optionally one or two amino acids are conservatively substituted); LCDR2, (e.g., SEQ ID NO: 29 or SEQ ID NO: 29 wherein optionally one or two amino acids are conservatively substituted); and/or LCDR3, (e.g., SEQ ID NO: 30 or SEQ ID NO: 30 wherein optionally one or two amino acids are conservatively substituted)) of the monoclonal antibody sc209. In additional aspects, the antibody or antigen binding fragment comprises all three heavy chain complementarity determining regions (HCDR1 (e.g., SEQ ID NO: 19, SEQ ID NO: 19 wherein optionally one or two amino acids are conservatively substituted); HCDR2 (e.g., SEQ ID NO: 20, SEQ ID NO: 20 wherein optionally one or two amino acids are conservatively substituted); and HCDR3 (e.g., SEQ ID NO: 21, SEQ ID NO: 21 wherein optionally one or two amino acids are conservatively substituted)) of the monoclonal antibody sc209; and all three light chain complementarity determining regions (LCDR1, (e.g., SEQ ID NO: 28 or SEQ ID NO: 28 wherein optionally one or two amino acids are conservatively substituted); LCDR2, (e.g., SEQ ID NO: 29 or SEQ ID NO: 29 wherein optionally one or two amino acids are conservatively substituted); and LCDR3, (e.g., SEQ ID NO: 30 or SEQ ID NO: 30 wherein optionally one or two amino acids are conservatively substituted)) of the monoclonal antibody sc209. In some embodiments, the heavy chain sequence comprises human heavy chain constant region sequence of human isotype IgG1 or IgG2.

In additional aspects, the antibody or antigen binding fragment comprises an amino acid sequence shown as SEQ ID NO:12, an amino acid sequence of the light chain variable region amino acid sequence of the antibody encoded by the purified DNA having ATCC Accession Number PTA-6296, or the amino encoded by the nucleotide sequence shown as nucleic acid residues 15-719 of SEQ ID NO:11.

In other additional aspects, the antibody or antigen binding fragment thereof comprises an amino acid sequence shown as SEQ ID NO:10, an amino acid sequence of the heavy chain variable region amino acid sequence of the antibody encoded by the purified DNA having ATCC Accession Number PTA-6296, or the amino acid sequence encoded by the nucleotide sequence shown as nucleic acid residues 13-1440 of SEQ ID NO:9.

In still other aspects, the antibody or antigen binding fragment comprises a light chain variable region comprising the amino acid sequence shown as SEQ ID NO:12, or the light chain variable region amino acid sequence of the antibody encoded by the purified DNA having ATCC Accession Number PTA-6296; and a heavy chain variable region comprising the amino acid sequence shown as SEQ ID NO:10, or the heavy chain variable region amino acid sequence of the antibody encoded by the purified DNA having ATCC Accession Number PTA-6296. In certain aspects antibody or antigen binding fragment comprises two heavy and two light chains.

In specific embodiments the human antibody or antigen binding fragment is sc209, or a fragment thereof.

Provided antibodies that bind the extracellular domain of OV064, induce internalization of OV064, and deliver toxic payload include chimeric antibodies or humanized antibodies, and antigen-binding fragments of the foregoing. Such chimeric or humanized antibodies and antigen binding fragments thereof are useful in the immunoconjugates, compositions, and methods of treatment and diagnosis provided herein.

In some embodiments, the antibody is mAb 8G5, mAb 4G10, mAb 3A4, or mAb 2F3 or an antigen-binding fragment of mAb 8G5, mAb 4G10, mAb 3A4, or mAb 2F3. Also provided is a chimeric or humanized mAb 8G5 or an antigen binding fragment thereof, a chimeric or humanized mAb 4G10 or an antigen binding fragment thereof, a chimeric or humanized mAb 3A4 or an antigen binding fragment thereof, or a chimeric or humanized mAb 2F, or an antigen binding fragment thereof.

Provided antibodies that bind the extracellular domain of OV064, induce internalization of OV064, and deliver toxic payload include human antibodies, and derivatives thereof. Such human antibodies and antigen binding fragments thereof are useful in the immunoconjugates, compositions, and methods of treatment and diagnosis provided herein.

In some embodiments, the antibody is mAb sc77, mAb sc189, or mAb sc209 or an antigen binding fragment of mAb sc77, an antigen binding fragment of mAb sc189, or an antigen binding fragment of mAb sc209.

In certain aspects, the methods of treatment of cancer include treatment of a subject with an immunoconjugate of the invention as individual therapy. In other aspects, the immunoconjugate can be used in combination with one or more other therapies. For example, the immunoconjugate may be combined with one or more additional chemotherapeutic agent(s) for combination therapy. Chemotherapeutic agents for combination therapy may suppress tumor growth, or kill tumor cells. Thus, methods of the invention comprise the methods of treatment of cancer comprising administering an immunoconjugate of the invention as described herein, and in combination with an additional chemotherapeutic agent. The methods comprising administration of an additional chemotherapeutic include administration of the additional agent prior to, concurrent with, or following administration of the immunoconjugate.

In certain embodiments, the provided methods are useful for treatment of a cancer which is a solid tumor, soft tissue tumor, liquid tumor, or a metastastic lesion of any of the foregoing. For example, the cancer may be ovarian cancer, breast cancer, lung cancer, pancreatic cancer or endometrial cancer.

In specific embodiments, the cancer is ovarian cancer, and the methods may be used for example, for treatment of ovarian adenocarcinoma, clear cell ovarian carcinoma, or serous ovarian carcinoma. Additionally, the methods may be useful for treatment of metastatic ovarian cancer involving a uterine, pelvic, extra-pelvic peritoneal, non-peritoneal or lymph node metastasis.

In specific embodiments, the cancer is lung cancer, and the methods may be used for example, for treatment of squamous cell carcinoma, or non-small-cell lung cancer.

In specific embodiments, the cancer is breast cancer, and the methods may be used for example, for treatment of early stage or late stage breast cancers, or different classification of breast cancer patients, including stage 0 breast cancer patients, stage I breast cancer patients, stage IIA breast cancer patients, stage IIB breast cancer patients, stage IIIA breast cancer patients, stage IIIB breast cancer patients, stage IV breast cancer patients, grade I breast cancer patients, grade II breast cancer patients, grade III breast cancer patients, malignant breast cancer patients, ductal carcinoma breast cancer patients, and lobular carcinoma breast cancer patients.

The invention also relates to fusion proteins comprising an antibody or portion thereof (e.g., heavy chain, light chain, variable region) of the invention and a non-immunoglobulin moiety.

The invention also relates to immunoconjugates comprising an antibody or an antigen-binding fragment of the invention. In some aspects the immunoconjugate comprises a cytotoxic moiety. For example, the cytotoxic moiety can comprise a radioisotope (e.g, a radioactive ion), a therapeutic agent (e.g., a chemotherapeutic agent, an antimetabolite, an alkylating agent, an anthracycline, an antibiotic, an anti-mitotic agent, a biological response modifier (e.g., a cytokine (e.g., an interleukin, an interferon, a tumor necrosis factor), a growth factor (e.g., a neurotrophic factor)), or a tumor activated prodrug (e.g., an enzyme and/or enzyme activated compound). When the cytotoxic moiety of the immunoconjugate is a therapeutic agent, the agent can comprise a maytansine, an auristatin, a dolastatin, a duocarmycin, a cryptophycin, a taxol, a DNA alkylating agent, a calicheamicin, or a derivative of any of the foregoing. In some aspects the cytotoxic moiety comprises a maytansine selected from DM1 or DM4. In other aspects the immunoconjugate comprises a detectable label moiety.

The invention further relates to liposome compositions comprising the antibodies, antigen-binding fragments, or immunoconjugates thereof of the invention. In some embodiments, the liposome is coated with antibody or antigen binding fragment. In additional embodiments, the liposome is filled with a cytotoxic or a cytostatic agent. In some aspects, the liposome is filled with a cytotoxin selected from the group consisting of a maytansine, an auristatin, a dolastatin, a duocarmycin, a cryptophycin, a taxol, a DNA alkylating agent, or a calicheamicin, or a derivative of the foregoing. In another embodiment the liposome is filled with nucleic acid sequence comprising RNA interference molecules which are capable of diminishing OV064 expression.

The invention further relates to an antibody, an antigen-binding fragment of an antibody, an antigen binding fragment of an antibody, a fusion protein or an immuno-conjugate of the invention as described herein for use in therapy or diagnosis of a cancer (e.g., ovarian cancer, breast cancer, lung cancer, pancreatic cancer and endometrial cancer). Additionally the invention relates to the use of an antibody, an antigen-binding fragment of an antibody, a fusion protein or an immuno-conjugate of the invention for the manufacture of a medicament for the treatment of a cancer (e.g., ovarian cancer, breast cancer, lung cancer, pancreatic cancer and endometrial cancer).

Still further the invention relates to pharmaceutical compositions comprising an antibody or antigen-binding fragment of the invention and a physiological acceptable carrier. Additionally encompassed in the invention are pharmaceutical compositions comprising immunoconjugates, and/or liposome compositions of the invention and a physiologically acceptable carrier.

The invention also relates to a method for detecting an OV064 expressing cell, or tumors expressing OV064, comprising contacting a composition comprising a cell or a tumor with a detectably labeled antibody or antigen-binding fragment thereof of the invention under conditions which allow interaction of the anti-OV064 antibody and the OV064 protein, and detecting formation of a complex between antibody or antigen binding fragment and the OV064 protein in the sample in order to detect the presence of the OV064 expressing cell or tumor expressing OV064 in the sample.

In one embodiment, methods for detecting the presence of tumor cells expressing OV064 can be performed in vivo, wherein a detectably labeled anti-OV064 antibody or antigen binding fragment of the invention is administered to a subject under conditions that allow interaction of the OV064 antibody or antigen binding fragment and the OV064 protein to occur; followed by detection of formation of a complex of OV064 and antibody or antigen binding fragment to thereby detect the presence of tumor cells expressing OV064 in vivo. The methods of detection, whether in vitro or in vivo, are useful for diagnosing or staging a cancerous disorder. In some embodiments, the disorder for diagnosis or staging is ovarian cancer, breast cancer, lung cancer, pancreatic cancer or endometrial cancer.

Any anti-OV064 antibody or antigen binding fragment of the invention provided herein may be useful in the diagnostic methods. For example, the antibody or antigen binding fragment can be an antibody or antigen binding fragment that competes with any monoclonal antibody selected from sc77, sc189, sc209, 3A4, 2F3, 4G10, and/or 8G5, which detects OV064 expressed on cells. The anti-OV064 antibody or antigen binding fragment thereof of the invention used in the in vivo and in vitro diagnostic methods can be directly or indirectly labeled with a detectable substance to facilitate detection of the bound or unbound binding agent. Suitable detectable substances include various biologically active enzymes, prosthetic groups, fluorescent materials, luminescent materials, paramagnetic (e.g., nuclear magnetic resonance active) materials, and radioactive materials. In some embodiments, the anti-OV064 antibody or fragment thereof is coupled to a radioactive ion, e.g., indium ($^{111}$In), iodine ($^{131}$I or $^{125}$I), yttrium ($^{90}$Y), lutetium ($^{177}$Lu), actinium ($^{225}$Ac), bismuth ($^{212}$Bi or $^{213}$Bi), sulfur ($^{35}$S), carbon ($^{14}$C), tritium ($^3$H), rhodium ($^{188}$Rh), technetium ($^{99}$mTc), praseodymium, or phosphorous ($^{32}$P).

The invention also relates to isolated and/or recombinant nucleic acids encoding the antibodies, antigen-binding fragments, heavy chains, light chains and portions of the heavy chains and light chains of the antibodies described herein, and to expression constructs or vectors comprising the expression constructs. In specific embodiments the invention includes plasmid Ov64sc077 (ATCC Accession No. PTA-6294), plasmid Ov64sc189 (ATCC Accession No. PTA-6295) or plasmid Ov64sc209 (ATCC Accession No. PTA-6296). Still further, the invention encompasses antibodies produced by host cells expressing the antibodies encoded by plasmid Ov64sc077 (ATCC Accession No. PTA-6294), plasmid Ov64sc189 (ATCC Accession No. PTA-6295) or plasmid Ov64sc209 (ATCC Accession No. PTA-6296).

For example, in one embodiment is provided an expression vector comprising a gene encoding a humanized antibody light chain, comprising a nucleotide sequence encoding a complementarity determining region sequence derived from a light chain of a murine antibody (e.g., 4G10, 3A4, 2F3, 8G5), and a framework region derived from a light chain of human origin. In another embodiment is provided an expression vector comprising a gene encoding a humanized antibody heavy chain, comprising a nucleotide sequence encoding a complementarity determining region derived from a heavy chain of a murine antibody (e.g., 4G10, 3A4, 2F3, 8G5), and a framework region derived from a heavy chain of human origin. An additional embodiment provides a host cell comprising the foregoing expression vectors, expressing heavy and light chain antibodies, and a still further embodiment provides a method of producing a humanized antibody comprising maintaining the host cell under conditions appropriate for expression of a humanized immunoglobulin, whereby humanized immunoglobulin chains are expressed and a humanized antibody is produced. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NS0), Chinese hamster ovary cells (CHO), COS cells. Additionally cells include oocyte cells, and cells from a transgenic animal, e.g., mammary epithelial cell. For example, nucleic acids encoding an antibody or a modified antibody or an antigen binding fragment thereof described herein can be expressed in a transgenic animal.

In another embodiment is provided an expression vector comprising a gene encoding a human antibody light chain, comprising a nucleotide sequence encoding one, two, or three complementarity determining region sequences from a light chain of a human antibody (e.g., sc77, sc189, or sc209), and a framework region derived from a light chain of human origin. For example, provided expression vectors include expression vectors encoding a human antibody light chain comprising all three complementarity determining regions from a light chain of human antibody (e.g., sc77, sc189, or sc209). In another embodiment is provided an expression vector comprising a gene encoding a human antibody heavy chain, comprising a nucleotide sequence encoding one, two, or three complementarity determining regions from a heavy chain of a human antibody (e.g., sc77, sc189, or sc209), and a framework region derived from a heavy chain of human origin. Additionally, provided expression vectors include expression vectors encoding a human antibody heavy chain comprising all three complementarity determining regions from a heavy chain of human antibody (e.g., sc77, sc189, or sc209). An additional embodiment provides a host cell comprising the foregoing expression vectors encoding heavy and light chain antibody sequences. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NS0), Chinese hamster ovary cells (CHO), COS cells. Additionally cells include oocyte cells, and cells from a transgenic animal, e.g., mammary epithelial cell. For example, nucleic acids encoding an antibody or a modified antibody or an antigen binding fragment thereof described herein can be expressed in a transgenic animal.

A still further embodiment provides a method of producing a human antibody comprising maintaining the host cell under conditions appropriate for expression of a human immunoglobulin, whereby human immunoglobulin chains are expressed and a human antibody is produced. For example, methods of expression of human antibodies include use of host cells wherein a first recombinant nucleic acid molecule encoding a human antibody light chain and a second recombinant nucleic acid molecule encoding a human antibody heavy chain are comprised in a single expression vector The invention also relates to a host cell that comprises a nucleic acid of the invention. In specific embodiments, the invention is Hybridoma 8G5 (ATCC Accession No. PTA-6403), Hybridoma 4G10 (ATCC Accession No. PTA-6402), Hybridoma 3A4 (ATCC Accession No. PTA-6401), or Hybridoma 2F3 (ATCC Accession No. PTA-6400). Still further, the invention encompasses antibodies produced by Hybridoma 8G5 (ATCC Accession No. PTA-6403), Hybridoma 4G10 (ATCC Accession No. PTA-6402), Hybridoma 3A4 (ATCC Accession No. PTA-6401), or Hybridoma 2F3 (ATCC Accession No. PTA-6400).

We have found that certain antibodies to the Ov064 (also known as B7H4, B7x, B7S1) protein rapidly internalize and can bring toxic payloads of toxin (e.g., maytansines, e.g., DM1 and DM4) into Ov064 expressing cells, leading to cell death. Ov064 is expressed on >90% of ovarian cancer tissues as well as breast and lung cancer tissue samples. See International Patent Publication No. WO200012758, published Mar. 9, 2000; International Patent Publication No. WO200036107, published Jun. 22, 2000; U.S. Patent Application Publication No. US20030165504, published Sep. 4, 2003; and U.S. Patent Application Publication No. US20030091580, published May 15, 2003. As a result, we concluded toxin conjugated antibodies to OV064 have therapeutic utility in cancers where OV064 is expressed (e.g., breast cancer, ovarian cancer). Ov064, also known as B7-H4, B7x, and B7S1, a 282 amino acid protein, has been described as a member of the B7-family of lymphocyte co-inhibitory proteins (See, Prasad et al., *Immunity* 18: 863-873 (2003); Sica et al., *Immunity* 18: 849-861 (2003); Zang et al., *Proc Natl Acad Sci USA* 100: 10388-10392 (2003); GenBank Accession No. NMO24626, each of which are incorporated herein by reference). It has also been demonstrated that Ov064 is a ligand for BTLA, a co-inhibitory receptor which shares homology with CTLA4 and CD28 co-stimulatory receptors. Ov064 has been shown to inhibit T-cell activation (Prasad et al., *Immunity* 18: 863-873 (2003); Sica et al., *Immunity* 18: 849-861 (2003); Zang et al., *Proc Natl Acad Sci USA* 100: 10388-10392 (2003)). It is also possible that tumor cells express this antigen to avoid being recognized by the immune system. Thus, anti-Ov064 antibodies may act in certain aspects in a similar manner as that found for anti-CTLA4 antibodies (Egen et al., *Nat Immunol* 3: 611-618 (2002). An antibody to Ov064 therefore could possibly exert a dual effect in patients with cancer: anti-Ov064 antibodies may deliver a toxic payload to tumor cells expressing OV064, as well as diminish the immunosuppressive effects of Ov064, thereby enhancing tumor cell killing via direct delivery of toxin, as well as activated immune cells. We have found that only a subset of antibodies which bind OV064 are efficacious in delivery to cells of toxic payloads sufficient to induce cell killing. This effect does not appear to relate directly to affinity of binding to OV064, rather a subset of antibodies which compete with the monoclonal antibodies and human monoclonal antibodies provided herein are preferred for use in the methods described. We have found an anti-OV064 antibody which binds to an epitope located within the region of about amino acids 133-257 of SEQ ID NO:44 is capable of delivering toxic payload to a cell expressing OV064. For example, an anti-OV064 antibody which binds to an epitope located wholly or partially within the region of about amino acids 167-176 or about amino acids 177-181 of human OV064 (SEQ ID NO:44) is capable of delivery of toxic payload. In another example, an anti-OV064 antibody which binds to an epitope wholly or partially within the region of about amino acids 238-257 of human OV064 (SEQ ID NO:44) is capable of delivery of toxic payload. In contrast, an anti-OV064 antibody which binds to an epitope located within the region of amino acids 32-133 of SEQ ID NO:44 was found not capable of delivery of toxic payload to cells expressing OV064. For example, an antibody which binds an epitope located wholly or partially within the region of about amino acids 67-76 of human OV064 (SEQ ID NO:44) was incapable of delivery of toxic payload.

Unless otherwise defined herein, scientific and technical terms used in connection with the present invention have the meanings that are commonly understood by those of ordinary skill in the art. Generally, nomenclature utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation and transfection (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (3rd ed., Cold Spring Harbor Laboratory Press, Cold Spring Harbor, N.Y. (2000)), See generally, Harlow, E. and Lane, D. (1988) *Antibodies: A Laboratory Manual*, Cold Spring Harbor Laboratory Press, Cold Spring Harbor, N.Y. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients. Furthermore, unless otherwise required by context, singular terms shall include pluralities and plural terms shall include the singular.

The instant invention is most clearly understood with reference to the following definitions, as well as additional definitions as set forth throughout the description:

As used herein, the term "antibody" "antibody peptide(s)" or "immunoglobulin" refers to single chain, two-chain, and multi-chain proteins and glycoproteins that belong to the classes of polyclonal, monoclonal, chimeric and human or humanized immunoglobulin proteins. The term "antibody" also includes synthetic and genetically engineered variants thereof.

As used herein, the term "antibody fragment" or "antigen binding fragment" of an antibody refers to Fab, Fab', F(ab')$_2$, and Fv fragments, single chain antibodies, functional heavy chain antibodies (nanobodies), as well as any portion of an antibody having specificity toward at least one desired epitope, that competes with the intact antibody for specific binding (e.g., an isolated portion of a complementarity determining region having sufficient framework sequences so as to bind specifically to an epitope). Antigen binding fragments can be produced by recombinant techniques, or by enzymatic or chemical cleavage of an intact antibody.

As used herein, the term "human antibody" refers to an antibody that possesses a sequence that is derived from a human germ-line immunoglobulin sequence, such as antibodies derived from transgenic mice having human immunoglobulin genes (e.g., XENOMOUSE™ genetically engineered mice (Abgenix)), human phage display libraries, or human B cells.

As used herein, the term "humanized antibody" refers to an antibody that is derived from a non-human antibody (e.g., murine) that retains or substantially retains the antigen-binding properties of the parent antibody but is less immunogenic in humans. Humanized as used herein is intended to include deimmunized antibodies.

The term "modified" antibody, as used herein, refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such modified antibodies include humanized, CDR grafted, chimeric, in vitro generated (e.g., by phage display) antibodies, and may optionally include variable or constant regions derived from human germline immunoglobulin sequences or human immunoglobulin genes or antibodies which have been prepared, expressed, created or isolated by any means that involves splicing of human immunoglobulin gene sequences to alternative immunoglobulin sequences.

The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition.

The term "bispecific antibody" or "bifunctional antibody" refers to an antibody that displays dual binding specificity for two epitopes, where each binding site differs and recognizes a different epitope.

The term "agent" is used herein to denote a chemical compound, a mixture of chemical compounds, a biological macromolecule, or an extract made from biological materials.

The term "anti-cancer agent" or "chemotherapeutic agent" is used herein to refer to agents that have the functional property of inhibiting a development or progression of a neoplasm in a human, particularly a malignant (cancerous) lesion, such as a carcinoma, sarcoma, lymphoma, or leukemia Inhibition of metastasis is frequently a property of anti-cancer or chemotherapeutic agents. A chemotherapeutic agent may be a cytotoxic or cytostatic agent. A cytostatic agent refers to an agent which inhibits or suppresses cell growth and/or multiplication of cells.

"Cytotoxic agents" refer to compounds which cause cell death primarily by interfering directly with the cell's functioning or inhibit or interfere with cell myosis, including, but not limited to, alkylating agents, tumor necrosis factors, intercalators, microtubulin inhibitors, and topoisomerase inhibitors. A toxic payload as used herein refers to a sufficient amount of cytotoxic agent which, when delivered to a cell results in cell death. A toxic payload may include a sufficient amount of immunoconjugate comprising a cytotoxic agent, wherein the immunoconjugate comprises an antibody or antigen binding fragment of the invention. A toxic payload may also include a sufficient amount of an immunoconjugate comprising a cytotoxic agent, wherein the immunoconjugate comprises a secondary antibody or antigen binding fragment thereof which recognizes and binds an antibody or antigen binding fragment of the invention.

As used herein the phrase, a sequence "derived from" or "specific for a designated sequence" refers to a sequence that comprises a contiguous sequence of approximately at least 6 nucleotides or at least 2 amino acids, preferably at least about 9 nucleotides or at least 3 amino acids, more preferably at least about 10-12 nucleotides or 4 amino acids, and even more preferably at least about 15-21 nucleotides or 5-7 amino acids corresponding, i.e., identical or complementary to, a region of the designated sequence. In certain embodiments, the sequence comprises all of a designated nucleotide or amino acid sequence. The sequence may be complementary (in the event a polynucleotide sequence) or identical to a sequence that is unique to a particular sequence as determined by techniques known in the art. Regions from which sequences may be derived, include but are not limited to, regions encoding specific epitopes, regions encoding complementarity determining regions, regions encoding framework sequences, regions encoding constant domain regions, regions encoding variable domain regions, as well as non-translated and/or non-transcribed regions. The derived sequence will not necessarily be derived physically from the sequence of interest under study, but may be generated in any manner, including, but not limited to, chemical synthesis, replication, reverse transcription or transcription, that is based on the information provided by the sequence of bases in the region(s) from which the polynucleotide is derived. As such, it may represent either a sense or an antisense orientation of the original polynucleotide. In addition, combinations of regions corresponding to that of the designated sequence may be modified or combined in ways known in the art to be consistent with the intended use. For example, a sequence may comprise two or more contiguous sequences which each comprise part of a designated sequence, and are interrupted with a region which is not identical to the designated sequence is intended to represent a sequence derived from the designated sequence.

As used herein, the phrase "encoded by" refers to a nucleic acid sequence that codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. The nucleic acid sequences of the present invention which code for antibodies can be selected from the group consisting of SEQ ID NO:1, SEQ ID NO:3, SEQ ID NO:5, SEQ ID NO:7, SEQ ID NO:9, and SEQ ID NO:11. Also encompassed are polypeptide sequences that are immunologically identifiable with a polypeptide encoded by the sequence. Thus, a "polypeptide," "protein" or "amino acid" sequence has at least about 70%, 75%, 80%, 85%, 90%, 95% or more identity to the antibodies of the present invention. Further, the antibodies of the present invention may have at least about 60%, 70%, 75%, 80%, 85%, 90% or 95% similarity to a polypeptide or amino sequences of the antibodies of the present invention. The amino acid sequences of the antibodies of the present invention can be selected from the group consisting of SEQ ID NO:2, SEQ ID NO:4, SEQ ID NO:6, SEQ ID NO:8, SEQ ID NO:10, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:30.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the same.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 30%, 40%, or 50%, preferably at least 60%, and more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. The percent homology between two amino acid sequences can be determined using any method known in the art. For example, the Needleman and Wunsch, *J. Mol. Biol.* 48:444-453 (1970), algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. The percent homology between two nucleotide sequences can also be determined using the GAP program in the GCG software package, using a NWSgapdna.CMP matrix and a gap weight of 40, 50, 60, 70, or 80 and a length weight of 1, 2, 3, 4, 5, or 6. An exemplary set of parameters for determination of homology are a Blossum 62 scoring matrix with a gap penalty of 12, a gap extend penalty of 4, and a frameshift gap penalty of 5.

As used herein, the term "hybridizes under stringent conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the antibodies and antigen binding fragment thereof of the invention may have additional conservative or non-essential amino acid substitutions, which do not have a substantial effect on the polypeptide functions. Whether or not a particular substitution will be tolerated, i.e., will not adversely affect desired biological properties, such as binding activity can be determined as described in Bowie, J U et al. *Science* 247:1306-1310 (1990). A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of the binding agent, e.g., the antibody, without abolishing or more preferably, without substantially altering a biological activity, whereas an "essential" amino acid residue results in such a change.

As used herein, the term "isolated" refers to material that is removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

As used herein, the term "replicon" refers to any genetic element, such as a plasmid, a chromosome or a virus, that behaves as an autonomous unit of polynucleotide replication within a cell.

As used herein, the term "operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequence.

As used herein, the term "vector" refers to a replicon in which another polynucleotide segment is attached, such as to bring about the replication and/or expression of the attached segment.

As used herein, the term "control sequence" refers to a polynucleotide sequence that is necessary to effect the expression of a coding sequence to which it is ligated. The nature of such control sequences differs depending upon the host organism. In prokaryotes, such control sequences generally include a promoter, a ribosomal binding site and terminators and, in some instances, enhancers. The term "control sequence" thus is intended to include at a minimum all components whose presence is necessary for expression, and also may include additional components whose presence is advantageous, for example, leader sequences.

As used herein, the term "purified product" refers to a preparation of the product which has been isolated from the cellular constituents with which the product is normally associated and from other types of cells that may be present in the sample of interest.

As used herein, the term "epitope" refers to any protein determinate capable of binding specifically to an antibody or T-cell receptors. Epitopic determinants usually consist of chemically active surface groupings of molecules such as amino acids or sugar side chains and usually have specific three dimensional structural characteristics, as well as specific charge characteristics.

As used herein, "isotype" refers to the antibody class (e.g., IgM or IgG1) that is encoded by heavy chain constant region genes.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic as described in more detail herein. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, .beta.-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "specific binding" "bind(s) specifically" or "binding specificity" refers to the property of the antibody to: (1) to bind to OV064, e.g., human OV064 protein, with an affinity of at least $1 \times 10^7$ $M^{-1}$, and (2) preferentially bind to OV064, e.g., human OV064 protein, with an affinity that is at least two-fold, 50-fold, 100-fold, 1000-fold, or more greater than its affinity for binding to a non-specific antigen (e.g., BSA, casein) other than OV064.

As used herein, the term "treat" or "treatment" is defined as the application or administration of an anti-OV064 antibody or antigen binding fragment thereof to a subject, e.g., a patient, or application or administration to an isolated tissue or cell from a subject, e.g., a patient, which is returned to the subject. The anti-OV064 antibody or antigen binding fragment thereof, can be administered alone or in combination with, a second agent. The subject can be a patient (e.g., a human patient, a veterinary patient) having a cancer (e.g., ovarian cancer, breast cancer, lung cancer, pancreatic cancer and endometrial cancer)), a symptom of a cancer in which at least some of the cells express OV064 (e.g., ovarian cancer, breast cancer, lung cancer, pancreatic cancer and endometrial cancer), or a predisposition toward a cancer in which at least some of the cells express OV064 (e.g., ovarian cancer, breast cancer, lung cancer, pancreatic cancer and endometrial cancer). The treatment can be to cure, heal, alleviate, relieve, alter, remedy, ameliorate, palliate, improve or affect the disorder, the symptoms of the disorder or the predisposition toward the cancer. While not wishing to be bound by theory treating is believed to cause the inhibition, ablation, or killing of a cell in vitro or in vivo, or otherwise reducing capacity of a cell, e.g., an aberrant cell, to mediate a disorder, e.g., a disorder as described herein (e.g., a cancer).

As used herein, an amount of an anti-OV064 antibody "effective" or "sufficient" to treat a disorder, or a "therapeutically effective amount" or "therapeutically sufficient amount" refers to an amount of the antibody which is effective, upon single or multiple dose administration to a subject, in treating a cell, e.g., cancer cell (e.g., an OV064-expressing tumor cell), or in prolonging curing, alleviating, relieving or improving a subject with a disorder as described herein beyond that expected in the absence of such treatment. As used herein, "inhibiting the growth" of the tumor or cancer refers to slowing, interrupting, arresting or stopping its growth and metastases and does not necessarily indicate a total elimination of the tumor growth.

As used herein, "OV064," also known as "B7H4", "B7x", "B7S1," "Ovr110" protein refers to mammalian OV064, preferably human OV0664 protein. Human OV064 includes the protein product encoded by the nucleic acid sequence of OV064 shown in SEQ ID NO: 43; the amino acid sequence of OV064 is shown in SEQ ID NO: 44. The transcript encodes a protein product of 282 amino acids, and is described in Genbank accession no.: AY280972, submitted Apr. 22, 2003, and characterized as a B7-like member of the immunoglobulin superfamily of proteins, believed to play a critical role in antigen specific immune responses. OV064 has been characterized as a protein involved in immune responses, as well as cancers, including ovarian, breast, lung, endometrial, and pancreatic cancers. See also, Prasad et al., *Immunity* 18: 863-873 (2003); Sica et al., *Immunity* 18: 849-861 (2003); Zang et al., *Proc Natl Acad Sci USA* 100: 10388-10392 (2003); also International Patent Publication No. WO9963088, published Dec. 9, 1999; International Patent Publication No. WO200012758, published Mar. 9, 2000; International Publication No. WO200036107, published Jun. 22, 2000; International Publication No. WO200140269, published Jun. 7, 2001; International Publication No. WO200206317, published Jan. 24, 2002; International Publication No. WO0194641, published Dec. 13, 2001; International Publication No. WO0202624, published Jan. 10, 2002; International Publication No. WO02010187, published Feb. 7, 2002; International Publication No. WO03000012, published Jan. 3, 2003; International Publication No. WO04000221, published Dec. 31, 2003; International Publication No. WO040101756, published Nov. 25, 2004; and International Publication No. WO04113500, published Dec. 29, 2004. Accordingly, the term "human OV064" refers to protein product which has or is homologous to (e.g., at least about 85%, 90%, 95% identical to) an amino acid sequence as shown in SEQ ID NO: 44, or which is encoded by (a) a human OV064 nucleic acid sequence (e.g., SEQ ID NO: 43); (b) a nucleic acid sequence degenerate to a naturally occurring human OV064 sequence; (c) a nucleic acid sequence homologous to (e.g., at least about 85%, 90%, 95% identical to) the naturally occurring human OV064 nucleic acid sequence; or (d) a nucleic acid sequence that hybridizes to one of the foregoing nucleic acid sequences under stringent conditions, e.g., highly stringent conditions. The OV064 target is a member of the co-inhibitory cell surface molecules that can down regulate or inhibit an immune response (Chen, *Nat Rev Immunol* 4: 336-347 (2004)). It is generally known as B7-H4, B7x or B7S1 in the literature, and is believed to interact with BTLA (Choi et al., *J Immunol* 171: 4650-4654 (2003); Prasad et al., *Immunity* 18: 863-873 (2003); Sica et al., *Immunity* 18: 849-861 (2003); Zang et al., *Proc Natl Acad Sci USA* 100: 10388-10392 (2003). Further, OV064 is a cell surface protein found in greater than 90% of ovarian cancers and 25-30% of lung and breast cancer patient samples (See Choi et al., *J Immunol* 171: 4650-4654 (2003)). Antibody therapeutics directed to Ov064 can be used alone in unconjugated form to thereby inhibit the OV064-expressing cancerous cells by, e.g., bypass tumor induced immune suppression and promote T-cell mediated killing of tumor cells.

An "anti-OV064 antibody" is an antibody that interacts with (e.g., binds to) OV064, preferably human OV064 protein. The provided anti-OV064 antibodies or antigen binding fragments thereof interact with, e.g., binds to, the extracellular domain of OV064, e.g., the extracellular domain of human OV064 located at about amino acids 32-282 of human OV064. In one embodiment, the anti-OV064 antibody or antigen binding fragment thereof binds all or part of the epitope of an antibody described herein, e.g., sc77, sc189, sc209, 4G10, 3A4, 2F3 and/or 8G5. The anti-OV064 antibody can inhibit, e.g., competitively inhibit, the binding of an antibody described herein, e.g., sc77, sc189, sc209, 4G10, 3A4 2F3 and/or 8G5 to human OV064. An anti-OV064 antibody may bind to an epitope, e.g., a conformational or a linear epitope, which epitope when bound prevents binding of an antibody described herein, e.g., sc77, sc189, sc209, 4G10, 3A4, 2F3 and/or 8G5. In one embodiment, the anti-OV064 antibody binds to an epitope located within the region of about amino acids 133-257 of SEQ ID NO:44, or about amino acids 133-183 of SEQ ID NO:44, and preferably wholly or partially within the region of about amino acids 167-176 or about amino acids 177-181 of human OV064 (SEQ ID NO:44). In another embodiment, the anti-OV064 antibody binds to an epitope located within the region of about amino acids 133-257 of SEQ ID NO:44, or about amino acids 189-257 of SEQ ID NO:44, and preferably wholly or partially within the region of about amino acids 238-257 of human OV064 (SEQ ID NO:44). In still another embodiment, the anti-OV064 antibody binds to an epitope located within the region of about amino acids 32-133 of SEQ ID NO:44, preferably wholly or partially within the region of about amino acids 67-76 of human OV064 (SEQ ID NO:44).

Antibodies

The antibody structural unit is a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety). The variable regions of each light/heavy chain pair form the antibody binding site. Preferred isotypes for the anti-OV064 antibodies are IgG immunoglobulins, which are classified into four subclasses, IgG1, IgG2, IgG3 and IgG4, having different gamma heavy chains. Most therapeutic antibodies are human, chimeric, or humanized antibodies of the IgG1 type.

The variable regions of each heavy and light chain pair form the antigen binding site. Thus, an intact IgG antibody has two binding sites which are the same. However, bifunctional or bispecific antibodies are artificial hybrid constructs which have two different heavy/light chain pairs, resulting in two different binding sites.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk *J. Mol. Biol.* 196:901-917 (1987); Chothia et al. *Nature* 342:878-883 (1989). As used herein, CDRs are referred to for each of the heavy (HCDR1, HCDR2, HCDR3) and light (LCDR1, LCDR2, LCDR3) chains.

Useful immunogens for the purpose of this invention include OV064 (e.g., human OV064)-expressing cells (e.g., a tumor cell line, e.g., SKBR3 cells, ZR75-1 cells, OVCAR3 cells, MDA-MB-468 cells, MCF7 cells, DLD1 cells, or fresh or frozen ovarian tumor cells, recombinant cells expressing OV064); membrane fractions of OV064-expressing cells (e.g., a ovarian tumor cell line, e.g., SKBR3 cells, or fresh or frozen ovarian tumor cells, recombinant cells expressing OV064); isolated or purified OV064, e.g., human OV064 protein (e.g., biochemically isolated OV064, or a portion thereof, e.g., the extracellular domain of OV064, recombinant cells expressing OV064).

The antibodies of the present invention can be polyclonal antibodies, monoclonal antibodies, chimeric antibodies (See U.S. Pat. No. 6,020,153) or human or humanized antibodies or antibody fragments or derivatives thereof. Synthetic and genetically engineered variants (See U.S. Pat. No. 6,331,415) of any of the foregoing are also contemplated by the present invention. Monoclonal antibodies can be produced by a variety of techniques, including conventional murine monoclonal antibody methodology e.g., the standard somatic cell hybridization technique of Kohler and Milstein, *Nature* 256: 495 (1975). See generally, Harlow, E. and Lane, D. (1988) *Antibodies: A Laboratory Manual*, Cold Spring Harbor Laboratory Press, Cold Spring Harbor, N.Y. Preferably, for therapeutic applications, the antibodies of the present invention are human or humanized antibodies. The advantage of human or humanized antibodies is that they potentially decrease or eliminate the immunogenicity of the antibody in a host recipient, thereby permitting an increase in the bioavailability and a reduction in the possibility of adverse immune reaction, thus potentially enabling multiple antibody administrations.

Modified antibodies include humanized, chimeric or CDR-grafted antibodies. Human anti-mouse antibody (HAMA) responses have led to development of chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. The presence of such murine or rat derived proteins can lead to the rapid clearance of the antibodies or can lead to the generation of an immune response against the antibody by a patient. In order to avoid the utilization of murine or rat derived antibodies, humanized antibodies where sequences are introduced to an antibody sequence to make it closer to human antibody sequence, or fully human antibodies generated by the introduction of human antibody function into a rodent have been developed so that the rodent would produce antibodies having fully human sequences. Human antibodies avoid certain of the problems associated with antibodies that possess murine, rabbit, or rat variable and/or constant regions.

Human Antibodies

Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations. Also, human antibodies can be produced using genetically engineered strains of animals in which the antibody gene expression of the animal is suppressed and functionally replaced with human antibody gene expression.

Methods for making humanized and human antibodies are known in the art. One method for making human antibodies employs the use of transgenic animals, such as a transgenic mouse. These transgenic animals contain a substantial portion of the human antibody producing genome inserted into their own genome and the animal's own endogenous antibody production is rendered deficient in the production of antibodies. Methods for making such transgenic animals are known in the art. Such transgenic animals can be made using XENOMOUSE™ technology or by using a "minilocus" approach. Methods for making XENOMICE™ are described in U.S. Pat. Nos. 6,162,963, 6,150,584, 6,114,598 and 6,075,181, which are incorporated herein by reference. Methods for making transgenic animals using the "minilocus" approach are described in U.S. Pat. Nos. 5,545,807, 5,545,806 and 5,625,825; also see International Publication No. WO93/12227, which are each incorporated herein by reference.

Using the XENOMOUSE™ technology, human antibodies can be obtained by immunizing a XENOMOUSE™ mouse (Abgenix, Fremont, Calif.) with an antigen of interest. The lymphatic cells (such as B-cells) are recovered from the mice that express antibodies. These recovered cells can be fused with myeloid-type cell line to prepare immortal hybridoma cell lines, using standard methodology. These hybridoma cell lines can be screened and selected to identify hybridoma cell lines that produce antibodies specific to the antigen of interest. Alternatively, the antibodies can be expressed in cell lines other than hybridoma cell lines. More specifically, sequences encoding particular antibodies can be cloned from cells producing the antibodies and used for transformation of a suitable mammalian host cell. In a preferred method, spleen and/or lymph node lymphocytes from immunized mice are isolated from the mice and plated in plaque assays as described previously in Babcook et al., *Proc Natl Acad Sci USA*. 93: 7843-8 (1996), which is incorporated herein by reference. Briefly, cells are plated in agar with sheep red blood cells, coated with OV064 antigen and cells secreting mAb against the OV064 antigen would fix complement and lyse the red blood cells immediately surrounding the mAb producing cells. Cells within the cleared plaques are lifted for sequencing of the immunoglobulin sequences and subcloning into expression vectors. Supernatants from transiently transfected cells containing OV064 specific mAb were subsequently screened by ELISA and for binding to cells by flow cytometry. We utilized these techniques in accordance with the present invention for the preparation of antibodies specific to OV064. The variable sequences, or a portion thereof of the produced human antibodies comprising complementarity determining regions which bind particular epitopes may be utilized for production of modified antibodies. For example, the variable regions of the produced antibodies may be spliced into an expression cassette for ease of transfer of constructs, increased expression of constructs, and/or incorporation of constructs into vectors capable of expression of full length antibodies. Herein, we describe the production of multiple hybridoma cell lines that produce antibodies specific to OV064. Further, we provide a characterization of the antibodies produced by such cell lines, including nucleotide and amino acid sequence analyses of the heavy and light chains of such antibodies, and vectors comprising the coding sequences of the immunoglobulin chains.

Humanization and Display Technologies

As discussed above, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art. See e.g., Winter and Harris *Immunol Today* 14:43-46 (1993) and Wright et al. *Crit. Reviews in Immunol*. 12125-168 (1992). The antibody of interest may be engineered by recombinant DNA techniques to substitute the CH1, CH2, CH3, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al. *Proc Natl Acad Sci USA.* 84:3439 (1987) and *J. Immunol.* 139:3521 (1987)). mRNA is isolated from a hybridoma or other cell producing the antibody and used to produce cDNA: The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Isotypes can be IgG1, IgG2, IgG3 or IgG4. Preferred isotypes for antibodies of the invention are IgG1 and IgG2. Either of the human light chain constant regions, kappa or lambda, may be used. The chimeric, humanized antibody is then expressed by conventional methods.

Humanized antibodies can also be made using a CDR-grafted approach. Techniques of generation of such humanized antibodies are well known in the art. Generally, humanized antibodies are produced by obtaining nucleic acid sequences that encode the variable heavy and variable light sequences of an antibody that binds to OV064, identifying the complementary determining region or "CDR" in the variable heavy and variable light sequences and grafting the CDR nucleic acid sequences on to human framework nucleic acid sequences. (See, for example, U.S. Pat. Nos. 4,816,567 and 5,225,539, which are incorporated by reference). The location of the CDRs and framework residues can be determined (see, Kabat, E. A., et al. (1991) *Sequences of Proteins of Immunological Interest, Fifth Edition*, U.S. Department of Health and Human Services, NIH Publication No. 91-3242, and Chothia, C. et al. *J. Mol. Biol.* 196:901-917 (1987), which are incorporated herein by reference). The human framework that is selected is one that is suitable for in vivo administration, meaning that it does not exhibit immunogenicity. For example, such a determination can be made by prior experience with in vivo usage of such antibodies and studies of amino acid similarities.

Once the CDRs and FRs of the cloned antibody that are to be humanized are identified, the amino acid sequences encoding the CDRs are identified and the corresponding nucleic acid sequences grafted on to selected human FRs. This can be done using known primers and linkers, the selection of which are known in the art. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen. After the CDRs are grafted onto selected human FRs, the resulting "humanized" variable heavy and variable light sequences are expressed to produce a humanized Fv or humanized antibody that binds to OV064. Typically, the humanized variable heavy and light sequences are expressed as a fusion protein with human constant domain sequences so an intact antibody that binds to OV064 is obtained. However, a humanized Fv antibody can be produced that does not contain the constant sequences.

Also within the scope of the invention are humanized antibodies in which specific amino acids have been substituted, deleted or added. In particular, humanized antibodies have amino acid substitutions in the framework region, such as to improve binding to the antigen. For example, a selected, small number of acceptor framework residues of the humanized immunoglobulin chain can be replaced by the corresponding donor amino acids. Locations of the substitutions include amino acid residues adjacent to the CDR, or which are capable of interacting with a CDR (see e.g., U.S. Pat. No. 5,585,089). The acceptor framework can be a mature human antibody framework sequence or a consensus sequence. As used herein, the term "consensus sequence" refers to the sequence formed from the most frequently in a region among related family members.

Other techniques for humanizing antibodies are described in Padlan et al. EP 519596 A1, published on Dec. 23, 1992.

The anti-OV064 antibody, or antigen fragment thereof, includes other humanized antibodies which may also be modified by specific deletion of human T cell epitopes or "deimmunization" by the methods disclosed in WO 98/52976 and WO 00/34317, the contents of which are incorporated herein by reference. Briefly, the murine heavy and light chain variable regions of an anti-OV064 antibody can be analyzed for peptides that bind to MHC Class II; these peptides represent potential T-cell epitopes. For detection of potential T-cell epitopes, a computer modelling approach termed "peptide threading" can be applied, and in addition a database of human MHC class II binding peptides can be searched for motifs present in the murine VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible conservative substitutions are made, often but not exclusively, an amino acid common at this position in human germline antibody sequences may be used. Human germline sequences are disclosed in Tomlinson, I. A. et al. *J. Mol. Biol.* 227:776-798(1992); Cook, G. P. et al. *Immunol. Today* Vol. 16 (5): 237-242(1995); Chothia, D. et al. *J. Mol. Bio.* 227:799-817(1992). The V BASE directory provides a comprehensive directory of human immunoglobulin variable region sequences (compiled by Tomlinson, I. A. et al. MRC Centre for Protein Engineering, Cambridge, UK). After the deimmunized VH and VL of an anti-OV064 antibody are constructed by mutagenesis of the murine VH and VL genes, the mutagenized variable sequence can, optionally, be fused to a human constant region, e.g., human IgG1 or κ constant regions.

Anti-OV064 antibodies that are not intact antibodies are also useful in this invention. Such antibodies may be derived from any of the antibodies described above. For example, antigen-binding fragments, as well as full-length monomeric, dimeric or trimeric polypeptides derived from the above-described antibodies are themselves useful. Useful antibody homologs of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546 (1989)), which consists of a VH domain; (vii) a single domain functional heavy chain antibody, which consists of a VHH domain (known as a nanobody) see e.g., Cortez-Retamozo, et al., *Cancer Res.* 64: 2853-2857(2004), and references cited therein; and (vii) an isolated complementarity determining region (CDR), e.g., one or more isolated CDRs together with sufficient framework to provide an antigen binding fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. Science 242:423-426 (1988); and Huston et al. Proc. Natl. Acad. Sci. USA 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antibody fragments, such as Fv, F(ab')$_2$ and Fab may be prepared by cleavage of the intact protein, e.g. by protease or chemical cleavage.

In one approach, consensus sequences encoding the heavy and light chain J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, cosmids, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, Examples of suitable vectors that can be used include those that are suitable for mammalian hosts and based on viral replication systems, such as simian virus 40 (SV40), Rous sarcoma virus (RSV), adenovirus 2, bovine papilloma virus (BPV), papovavirus BK mutant (BKV), or mouse and human cytomegalovirus (CMV), and moloney murine leukemia virus (MMLV), native Ig promoters, etc.

Expression in eukaryotic host cells is useful because such cells are more likely than prokaryotic cells to assemble and secrete a properly folded and immunologically active antibody. However, any antibody produced that is inactive due to improper folding may be renaturable according to well known methods (Kim and Baldwin, "Specific Intermediates in the Folding Reactions of Small Proteins and the Mechanism of Protein Folding", Ann. Rev. Biochem. 51, pp. 459-89 (1982)). It is possible that the host cells will produce portions of intact antibodies, such as light chain dimers or heavy chain dimers, which also are antibody homologs according to the present invention.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Winter and Harris Immunol Today 14:43-46 (1993) and Wright et al. Crit. Reviews in Immunol. 12125-168 (1992), Hanes and Plucthau PNAS USA 94:4937-4942 (1997) (ribosomal display), Parmley and Smith Gene 73:305-318 (1988) (phage display), Scott TIBS 17:241-245 (1992), Cwirla et al. Proc Natl Acad Sci USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH 10:80-84 (1992), and U.S. Pat. No. 5,733,743. If display technologies are utilized to produce antibodies that are not human, such antibodies can be humanized as described above.

It will be appreciated that antibodies that are generated need not initially possess a particular desired isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816,397), cell-cell fusion techniques (see e.g., U.S. Pat. No. 5,916,771), among others. In the cell-cell fusion technique, a myeloma or other cell line is prepared that possesses a heavy chain with any desired isotype and another myeloma or other cell line is prepared that possesses the light chain. Such cells can, thereafter, be fused and a cell line expressing an intact antibody can be isolated.

By way of example, many of the OV064 antibodies discussed herein are human anti-OV064 IgG1 antibodies. Since such antibodies possess desired binding to the OV064 molecule, any one of such antibodies can be readily isotype switched to generate a human IgG4 isotype, for example, while still possessing the same variable region (which defines the antibody's specificity and affinity, to a certain extent). Accordingly, as antibody candidates are generated that meet desired "structural" attributes as discussed above, they can generally be provided with at least certain additional "functional" attributes that are desired through isotype switching.

Design and Generation of Other Therapeutics

In accordance with the present invention and based on the activity of the antibodies that are produced and characterized herein with respect to OV064, the design of other therapeutic modalities including other antibodies, other antagonists, or chemical moieties other than antibodies is facilitated. Such modalities include, without limitation, antibodies having similar binding activity or functionality, advanced antibody therapeutics, such as bispecific antibodies, immunoconjugates, and radiolabeled therapeutics, generation of peptide therapeutics, particularly intrabodies, and small molecules. Furthermore, as discussed above, the effector function of the antibodies of the invention may be changed by isotype switching to an IgG1, IgG2, IgG3, IgG4, IgD, IgA, IgE, or IgM for various therapeutic uses.

In connection with bispecific antibodies, bispecific antibodies can be generated that comprise (i) two antibodies one with a specificity to OV064 and another to a second molecule that are conjugated together, (ii) a single antibody that has one chain specific to OV064 and a second chain specific to a second molecule, or (iii) a single chain antibody that has specificity to OV064 and the other molecule. Such bispecific antibodies can be generated using techniques that are well known. For example, bispecific antibodies may be produced by crosslinking two or more antibodies (of the same type or of different types). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill. See also, e.g., Fanger et al. Immunol Methods 4:72-81 (1994) and Winter and Harris Immunol Today 14:43-46 (1993) and Wright et al. Crit. Reviews in Immunol. 12125-168 (1992). and in connection with (iii) see e.g., Traunecker et al. *Int. J. Cancer* (Suppl.) 7:51-52 (1992). Songsivilai & Lachmann Clin. *Exp. Immunol.* 79: 315-321 (1990), Kostelny et al. *J. Immunol.* 148: 1547-1553 (1992).

In addition, "Kappabodies" (Ill. et al. "Design and construction of a hybrid immunoglobulin domain with properties of both heavy and light chain variable regions" Protein Eng 10:949-57 (1997)), "Minibodies" (Martin et al. *EMBO J* 13:5303-9 (1994)), "Diabodies" (Holliger et al. *Proc Natl Acad Sci USA* 90:6444-6448 (1993)), or "Janusins" (Traunecker et al. *EMBO J* 10:3655-3659 (1991) and Traunecker et al. *Int J Cancer Suppl* 7:51-52 (1992)) may also be prepared.

Nucleic Acid and Polypeptides

In another embodiment, the present invention relates to polynucleotide and polypeptide sequences that encode for the antibodies or fragments thereof described herein. Such polynucleotides encode for both the variable and constant regions of each of the heavy and light chains, although other combinations are also contemplated by the present invention in accordance with the compositions described herein. The present invention also contemplates oligonucleotide fragments derived from the disclosed polynucleotides and nucleic acid sequences complementary to these polynucleotides.

The polynucleotides can be in the form of RNA or DNA. Polynucleotides in the form of DNA, cDNA, genomic DNA, nucleic acid analogs and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence which coding sequence, as a result of the redundancy or degeneracy of the genetic code, encodes the same polypeptide as the DNA provided herein.

The provided polynucleotides encode at least one heavy chain variable region and at least one light chain variable region of the present invention. Examples of such polynucleotides are shown in SEQ ID NOS: 1, 3, 5, 7, 9, and 11 as well as fragments, complements and degenerate codon equivalents thereof. For example, SEQ ID NO: 1 encodes for the heavy chain of sc77 and SEQ ID NO:3 encodes for the light chain of sc77. SEQ ID NO:5 encodes for the heavy chain of sc189 and SEQ ID NO: 7 encodes for the light chain of sc189. SEQ ID NO:9 encodes for the heavy chain of sc209 and SEQ ID NO: 11 encodes for the light chain of sc209.

The present invention also includes variant polynucleotides containing modifications such as polynucleotide deletions, substitutions or additions, and any polypeptide modification resulting from the variant polynucleotide sequence. A polynucleotide of the present invention may also have a coding sequence that is a variant of the coding sequence provided herein.

It is contemplated that polynucleotides will be considered to hybridize to the sequences provided herein if there is at least 50%, 60%, 70%, 75%, 80%, 85%, 90%, 95% identity between the polynucleotide and the sequence.

The present invention further relates to polypeptides that encode for the antibodies of the present invention as well as fragments, analogs and derivatives of such polypeptides. The polypeptides of the present invention may be recombinant polypeptides, naturally produced polypeptides or synthetic polypeptides. The fragment, derivative or analogs of the polypeptides of the present invention may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence that is employed for purification of the polypeptide or a proprotein sequence. Such fragments, derivatives and analogs are within the scope of the present invention. In various aspects, the polypeptides of the invention may be partially purified, or purified product.

A polypeptide of the present invention may have an amino acid sequence that is identical to that of the antibodies described herein or that is different by minor variations due to one or more amino acid substitutions. The variation may be a "conservative change" typically in the range of about 1 to 5 amino acids, wherein the substituted amino acid has similar structural or chemical properties, e.g., replacement of leucine with isoleucine or threonine with serine; replacement of lysine with arginine or histidine. In contrast, variations may include nonconservative changes, e.g., replacement of a glycine with a tryptophan. Similar minor variations may also include amino acid deletions or insertions or both. Guidance in determining which and how many amino acid residues may be substituted, inserted, or deleted without changing biological or immunological activity may be found using computer programs well known in the art, for example DNASTAR software (DNASTAR, Inc., Madison, Wis.).

The provided polypeptides encode at least one heavy chain variable region or at least one light chain variable region of the antibodies of the present invention. The provided polypeptides can encode at least one heavy chain variable region and one light chain variable region of the antibodies of the present invention. Examples of such polypeptides are those having the amino acid sequences shown in SEQ ID NOS: 2, 4, 6, 8, 10, 12, 13, 14, 15, 16, 17, 18, 19, 20, 21, 22, 23, 24, 25, 26, 27, 28, 29, and 30, and fragments thereof. Specifically, the heavy chain of sc77 has the amino acid sequence shown in SEQ ID NO: 2 and the light chain has the amino acid sequence shown in SEQ ID NO:4. The amino acid sequence of the heavy chain of sc189 is shown in SEQ ID NO:6 and the light chain has the amino acid sequence shown in SEQ ID NO:8. The amino acid sequence of the heavy chain of sc209 is shown in SEQ ID NO:10 and the light chain has the amino acid sequence shown in SEQ ID NO:12. The heavy chain CDR sequences of sc77 have the amino acid sequence shown in SEQ ID NO: 13 (HCDR1), SEQ ID NO:14 (HCDR2) and SEQ ID NO:15 (HCDR3); and the light chain CDRs have the amino acid sequence shown in SEQ ID NO:22 (LCDR1); SEQ ID NO:23 (LCDR2); and SEQ ID NO:24 (LCDR3). The amino acid sequence of the heavy chain CDRs of sc189 are shown in SEQ ID NO:16 (HCDR1), SEQ ID NO:17 (HCDR2), and SEQ ID NO:18 (HCDR3); and the light chain CDRs have the amino acid sequences shown in SEQ ID NO:25 (LCDR1), SEQ ID NO:26 (LCDR2), and SEQ ID NO:27 (LCDR3). The amino acid sequence of the heavy chain CDRs of sc209 are shown in SEQ ID NO:19 (HCDR1), SEQ ID NO:20 (HCDR2), and SEQ ID NO:21 (HCDR3) and the light chain CDRs have the amino acid sequences shown in SEQ ID NO:28 (LCDR1), SEQ ID NO:29 (LCDR2) and SEQ ID NO:30 (LCDR3).

The present invention also provides vectors that include the polynucleotides of the present invention, host cells which are genetically engineered with vectors of the present invention and the production of the antibodies of the present invention by recombinant techniques.

The appropriate DNA sequence may be inserted into the vector by a variety of procedures. In general, the DNA sequence is inserted into appropriate restriction endonuclease sites by procedures known in the art. The polynucleotide sequence in the expression vector is operatively linked to an appropriate expression control sequence (i.e. promoter) to direct mRNA synthesis. Examples of such promoters include, but are not limited to, the LTR or the SV40 promoter, the *E. coli* lac or trp, the phage lambda $P_L$, promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. For example, the vector can contain enhancers, which are transcription-stimulating DNA sequences of viral origin, such as those derived form simian virus such as SV40, polyoma virus, cytomegalovirus, bovine papilloma virus or Moloney sarcoma virus, or genomic, origin. The vector preferably also contains an origin of replication. The vector can be constructed to contain an exogenous origin of replication or, such an origin of replication can be derived from SV40 or another viral source, or by the host cell chromosomal replication mechanism.

In addition, the vectors optionally contain a marker gene for selection of transfected host cells such as dihydrofolate reductase or antibiotics, such as neomycin, GA418 (geneticin, a neomycin-derivative) or hygromycin, or genes which complement a genetic lesion of the host cells such as the absence of thymidine kinase, hypoxanthine phosphoribosyl transferase, dihydrofolate reductase, etc.

In order to obtain the antibodies of the present invention, one or more polynucleotide sequences that encode for the light and heavy chain variable regions and light and heavy chain constant regions of the antibodies of the present invention should be incorporated into a vector. Polynucleotide sequences encoding the light and heavy chains of the antibodies of the present invention can be incorporated into one or multiple vectors and then incorporated into the host cells.

As will be appreciated, antibodies in accordance with the present invention can be expressed in cell lines other than hybridoma cell lines. Sequences encoding the cDNAs or genomic clones for the particular antibodies can be used for a suitable mammalian or nonmammalian host cells. Transformation can be by any known method for introducing polynucleotides into a host cell, including, for example packaging the polynucleotide in a virus (or into a viral vector) and transducing a host cell with the virus (or vector) or by transfection procedures known in the art, for introducing heterologous polynucleotides into mammalian cells, e.g., dextran-mediated transfection, calcium phosphate precipitation, polybrene mediated transfection, protoplast fusion, electroporation, encapsulation of the polynucleotide(s) into liposomes and direct microinjection of the DNA molecule. The transformation procedure used depends upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, particle bombardment, encapsulation of the polynucleotide(s) in liposomes, peptide conjugates, dendrimers, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. Site directed mutagenesis of the antibody CH2 domain to eliminate glycosylation may be preferred in order to prevent changes in either the immunogenicity, pharmacokinetic, and/or effector functions resulting from non-human glycosylation. The expression methods are selected by determining which system generates the highest expression levels and produce antibodies with constitutive OV064 binding properties.

Further, expression of antibodies of the invention (or other moieties therefrom) from production cell lines can be enhanced using a number of known techniques. For example, the glutamine sythetase and DHFR gene expression systems are common approaches for enhancing expression under certain conditions. High expressing cell clones can be identified using conventional techniques, such as limited dilution cloning, Microdrop technology, or any other methods known in the art. The GS system is discussed in whole or part in connection with European Patent Nos. 0 216 846, 0 256 055, and 0 323 997 and European Patent Application No. 89303964.4.

In an exemplary system for recombinant expression of a modified antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750, 172, and 5,741,957.

Antibodies in accordance with the present invention have been analyzed structurally and functionally. In connection with the structures of the antibodies, amino acid sequences of each of the human heavy and kappa light chains were predicted based on cDNA sequences obtained through RT-PCR of the hybridomas. See Examples, Table 1, Table 2, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12. N-terminal sequencing of the antibodies was also conducted in confirmation of the results discussed in Examples to confirm sequences of the human antibody chains. Kinetic analyses of the antibodies were conducted to determine affinities. See Examples, Table 4. Antibodies in accordance with the invention have high affinities for OV064. Additionally, binding characteristics of the antibodies was conducted to determine epitopes which the antibodies recognize. Further, antibodies were analyzed for internalization into cells expressing OV064, by reducing gel electrophoresis (SDS-PAGE), western blot analysis, and antibody production by the hybridomas or host cells producing antibodies was assessed. See Examples and Tables below.

Conjugates

Several properties of Ov064 make it a suitable target for immunoconjugate tumor activated prodrug (TAP) or immunotoxin conjugate development: first, it is highly expressed on a large fraction of most ovarian cancers, and significantly expressed in lung and breast cancers; second, Ov064 rapidly internalizes and is capable of bringing cytotoxic concentrations of toxin (e.g., maytansine, e.g., DM1, DM4) into cells; third, Ov064 is expressed at very low levels or is absent in most normal human tissues and finally, Ov064 shows evidence of being polarized in normal tissue that express the antigen. The invention thus provides monoclonal antibodies which are internalized and capable of delivering toxic payloads of immunoconjugate into cells expressing OV064, but not into cells where the target is not expressed. The toxic payload may include immunotoxin comprising a cytotoxic agent. Immunoconjugates of antibodies, e.g., modified monoclonal antibodies and fully human mAb antibodies, and antigen binding fragments or derivatives thereof which specifically bind the extracellular domain of OV064, are provided.

As used herein, "immunoconjugate" comprises an anti-OV064 antibody or antigen binding fragment or derivative thereof, which is conjugated to another entity (e.g., to a cytotoxic or cytostatic moiety, a label moiety, a therapeutic moiety) or modified as described in more detail herein. As used herein, a "moiety" of an immunoconjugate is intended to refer to a component of the conjugate (e.g., an immunoglobulin moiety (i.e., an antibody or antigen binding fragment or derivative thereof), a therapeutic moiety, a cytotoxic moiety). For example, a cytotoxic moiety of an immunoconjugate comprises a cytotoxic agent which is conjugated to an antibody or antigen binding fragment. An anti-OV064 antibody or an antigen binding fragment thereof may be conjugated to another molecular entity, e.g., a cytotoxic or cytostatic agent, e.g., a therapeutic agent, a drug, a compound emitting radiation, molecules of plant, fungal, or bacterial origin, or a biological protein (e.g., a protein toxin) or particle (e.g., a recombinant viral particle, e.g., via a viral coat protein); a detectable agent; a pharmaceutical agent; and/or a protein or peptide that can mediate association of the antibody or antibody portion with another molecule (such as a streptavidin core region or a polyhistidine tag). For example, an antibody or antibody portion of the invention can be functionally linked by any suitable method (e.g., chemical coupling, genetic fusion, noncovalent association or otherwise) to one or more other molecular entities. Examples of linkers capable of being used to couple an immunotoxin to an antibody or antibody portion of the invention include, for example, N-succinimidyl 3-(2-pyridyldithio)proprionate (also known as N-succinimidyl 4-(2-pyridyldithio)pentanoate or SPP); 4-succinimidyl-oxycarbonyl-a-(2-pyridyldithio)-toluene (SMPT); N-succinimidyl-3-(2-pyridyldithio)butyrate (SDPB); 2-iminothiolane; S-acetylsuccinic anhydride; disulfide benzyl carbamate; carbonate; hydrazone linkers; N-(α-Maleimidoacetoxy) succinimide ester; N-[4-(p-Azidosalicylamido)butyl]-3'-(2'-pyridyldithio)propionamide (AMAS); N-[β-Maleimidopropyloxy]succinimide ester (BMPS); [N-e-Maleimidocaproyloxy]succinimide ester (EMCS); N-[g-Maleimidobutyryloxy]succinimide ester (GMBS); Succinimidyl-4-[N-Maleimidomethyl]cyclohexane-1-carboxy-[6-amidocaproate] (LC-SMCC); Succinimidyl 6-(3-[2-pyridyldithio]-propionamido)hexanoate (LC-SPDP); m-Maleimidobenzoyl-N-hydroxysuccinimide ester (MBS); N-Succinimidyl[4-iodoacetyl]aminobenzoate (SIAB); Succinimidyl 4-[N-maleimidomethyl]cyclohexane-1-carboxylate (SMCC); N-Succinimidyl 3-[2-pyridyldithio]-propionamido (SPDP); [N-e-Maleimidocaproyloxy]sulfosuccinimide ester (Sulfo-EMCS); N-[g-Maleimidobutyryloxy]sulfosuccinimide ester (Sulfo-GMBS); 4-Sulfosuccinimidyl-6-methyl-α-(2-pyridyldithio)toluamido]hexanoate) (Sulfo-LC-SMPT); Sulfosuccinimidyl 6-(3'-[2-pyridyldithio]-propionamido)hexanoate (Sulfo-LC-SPDP); m-Maleimidobenzoyl-N-hydroxysulfosuccinimide ester (Sulfo-MBS); N-Sulfosuccinimidyl[4-iodoacetyl]aminobenzoate (Sulfo-SIAB); Sulfosuccinimidyl 4-[N-maleimidomethyl]cyclohexane-1-carboxylate (Sulfo-SMCC); Sulfosuccinimidyl 4[p-maleimidophenyl]butyrate (Sulfo-SMPB); EGS; DST; DOTA; DTPA; and thiourea linkers.

In connection with immunoconjugates, the provided antibodies or antigen binding fragments thereof can be modified to act as immunoconjugates utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (U.S. Re. Pat. No. 35,500), 5,648,471, and 5,697,902. Immunoconjugates comprising toxins, tumor activated prodrugs, and radiolabeled molecules would be likely to kill cells expressing OV064, and particularly in those cells in which the provided antibodies and antigen binding fragments of the invention are effective (e.g., tumor cells expressing OV064, e.g., ovarian, lung, breast tumor cells).

As discussed, the antibody, antigen binding fragment, or derivative thereof can be conjugated to a therapeutic agent. For example, the anti-OV064 antibody, or antigen-binding fragment thereof, can be coupled to a biological protein, a molecule of plant or bacterial origin (or derivative thereof), e.g., a maytansinoid (e.g., maytansinol, e.g., DM1, DM4), a taxane, a calicheamicin, a duocarmycin, or derivatives thereof. The maytansinoid can be, for example, maytansinol or a maytansinol analogue. Examples of maytansinol analogues include those having a modified aromatic ring (e.g., C-19-decloro, C-20-demethoxy, C-20-acyloxy) and those having modifications at other positions (e.g., C-9-CH, C-14-alkoxymethyl, C-14-hydroxymethyl or aceloxymethyl, C-15-hydroxy/acyloxy, C-15-methoxy, C-18-N-demethyl, 4,5-deoxy). Maytansinol and maytansinol analogues are described, for example, in U.S. Pat. Nos. 5,208,020, 6,333, 410, the contents of which is incorporated herein by reference. Maytansinol can be coupled to antibodies using, e.g., an N-succinimidyl 3-(2-pyridyldithio)proprionate (also known as N-succinimidyl 4-(2-pyridyldithio)pentanoate or SPP), 4-succinimidyl-oxycarbonyl-a-(2-pyridyldithio)-toluene (SMPT), N-succinimidyl-3-(2-pyridyldithio)butyrate (SDPB), 2-iminothiolane, or S-acetylsuccinic anhydride. The taxane can be, for example, a taxol, taxotere, or novel taxane (see, e.g., International Patent Publication No. WO 01/38318, published May 31, 2001). The calicheamicin can be, for example, a bromo-complex calicheamicin (e.g., an alpha, beta or gamma bromo-complex), an iodo-complex calicheamicin (e.g., an alpha, beta or gamma iodo-complex), or analogs and mimics thereof. Bromo-complex calicheamicins include $I_1$—BR, $I_2$—BR, $I_3$—BR, $I_4$—BR, $\theta_1$-BR, $\theta_2$-BR and $K_1$—BR. Iodo-complex calicheamicins include $I_1$—I, $I_2$—I, $I_3$—I, $\theta_1$-I, $\theta_2$-I, $\Lambda_1$-I and $K_1$—BR. Calicheamicin and mutants, analogs and mimics thereof are described, for example, in U.S. Pat. No. 4,970,198, issued Nov. 13, 1990, U.S. Pat. No. 5,264,586, issued Nov. 23, 1993, U.S. Pat. No. 5,550,246, issued Aug. 27, 1996, U.S. Pat. No. 5,712,374, issued Jan. 27, 1998, and U.S. Pat. No. 5,714,586, issued Feb. 3, 1998, the contents of which are incorporated herein by reference. Duocarmycin analogs (e.g., KW-2189, DC88, DC89 CBI-TMI, and derivatives thereof are described, for example, in U.S. Pat. Nos. 5,070,092, 5,187,186, 5,641,780, 5,641,780, 4,923,990, and 5,101,038, the contents of which are incorporated herein by reference.

Examples of other therapeutic agents include, but are not limited to, cytochalasin B, gramicidin D, ethidium bromide, emetine, etoposide, tenoposide, colchicin, dihydroxy anthracin dione, mitoxantrone, 1-dehydrotestosterone, glucocorticoids, procaine, tetracaine, lidocaine, propranolol, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065 (see U.S. Pat. Nos. 5,475,092, 5,585,499, 5,846, 545), melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, mitomycin, puromycin anthramycin (AMC)), duocarmycin and analogs or derivatives thereof, and anti-mitotic agents (e.g., vincristine, vinblastine, taxol, auristatins (e.g., auristatin E) and maytansinoids, and analogs or homologs thereof.

The conjugates of the invention can be used for modifying a given biological response. The therapeutic agent is not to be construed as limited to classical chemical therapeutic agents. For example, the therapeutic agent may be a protein or polypeptide possessing a desired biological activity. Such proteins may include, for example, a toxin such as abrin, ricin A, pseudomonas exotoxin, gelonin, diphtheria toxin, or a component thereof (e.g., a component of pseudomonas exotoxin is PE38); a protein such as tumor necrosis factor, interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors. Similarly, the therapeutic agent can be a viral particle, e.g., a recombinant viral particle, that is conjugated (e.g., via a chemical linker) or fused (e.g., via a viral coat protein) to an anti-OV064 antibody of the invention. Introduction of the viral nucleic acid molecules, e.g., recombinant viral nucleic acid molecules, into cells, e.g., cancer cells, e.g., ovarian, breast or lung cancer cells associated with tumors that express OV064 can occur following binding and endocytosis of the anti-OV064 antibody/viral particle conjugate or fusion.

Therapeutically active radioisotopes can also be coupled to anti-OV064 antibodies, or antigen binding fragments, or derivatives thereof. Radioactive isotopes can be used in diagnostic or therapeutic applications. Radioactive isotopes that can be coupled to the anti-OV064 antibodies include, but are not limited to a-, b-, or g-emitters, or b- and g-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I) indium ($^{111}$In), technetium ($^{99}$mTc), phosphorus ($^{32}$P), carbon ($^{14}$C), and tritium ($^{3}$H), or one or more of the therapeutic isotopes listed above.

Useful detectable agents with which an antibody or an antibody portion of the invention may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described above). Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, b-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Pharmaceutical Compositions

In another aspect, the present invention provides compositions, e.g., pharmaceutically acceptable compositions, which include an antibody or an antigen binding fragment molecule, or derivative thereof described herein, formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical compositions are in the form of injectable or infusible solutions. The mode of administration is parenteral (e.g., intravenous, subcutaneous, intraperitoneal, intramuscular). In some embodiments, the antibody is administered by intravenous infusion or injection. In other embodiments, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the provided methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antigen binding fragments of the present invention can be administered by a variety of methods known in the art, although for many therapeutic applications, the route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or an antibody portion of the invention may be orally administered, for example, with an inert diluent or an assimilable edible carrier. The compound (and other ingredients if desired) may also be enclosed in a hard or soft shell gelatin capsule, compressed into tablets, buccal tablets, troches, capsules, elixiers, suspensions, syrups, wafers, and the like. To administer an antibody or an antibody fragment of the invention by other than parenteral administration, it may be necessary to coat the compound with, or co-administer the compound with, a material to prevent its inactivation.

Therapeutic compositions can be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody or an antigen binding fragment of the invention is 0.1-20 mg/kg, or 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective" amount of an antibody or an antigen binding fragment of the invention. A "therapeutically effective" amount refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter, e.g., tumor growth rate by at least about 20%, at least about 40%, at least about 60%, and in some aspects preferably at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

Also within the scope of the invention are kits comprising an anti-OV064 antibody, or antigen-binding fragment thereof. Also included in the invention are kits comprising immunoconjugates comprising an anti-OV064 antibody or antigen binding fragment conjugated to a cytotoxic moiety or a detectable label. Further included are kits comprising liposome compositions comprising anti-OV064 antibodies or antigen binding fragments thereof. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject. Instructions for use can include instructions for diagnostic applications of the anti-OV064 antibodies (or antigen-binding fragment thereof) to detect OV064, in vitro, e.g., in a sample, e.g., a biopsy or cells from a patient having a cancer, or in vivo. The instructions can include instructions for therapeutic application including suggested dosages and/or modes of administration, e.g., in a patient with a cancer (e.g., ovarian, breast, lung cancer). Other instructions can include instructions on coupling of the antibody to a chelator, a label or a therapeutic agent, or for purification of a conjugated antibody, e.g., from unreacted conjugation components. As discussed above, the kit can include a label, e.g., any of the labels described herein. As discussed above, the kit can include a therapeutic agent, e.g., a therapeutic agent described herein. In some applications the antibody will be reacted with other components, e.g., a chelator or a label or therapeutic agent, e.g., a radioisotope, e.g., yttrium or lutetium. In such cases the kit can include one or more of a reaction vessel to carry out the reaction or a separation device, e.g., a chromatographic column, for use in separating the finished product from starting materials or reaction intermediates.

The kit can further contain at least one additional reagent, such as a diagnostic or therapeutic agent, e.g., a diagnostic or therapeutic agent as described herein, and/or one or more additional anti-OV064 antibodies (or fragments thereof), formulated as appropriate, in one or more separate pharmaceutical preparations.

The kit can further contain a radioprotectant. The radiolytic nature of isotopes, e.g., $^{90}$Yttrium ($^{90}$Y) is known. In order to overcome this radiolysis, radioprotectants may be included, e.g., in the reaction buffer, as long as such radioprotectants are benign, meaning that they do not inhibit or otherwise adversely affect the labeling reaction, e.g., of an isotope, such as of $^{90}$Y, to the antibody. The formulation buffer of the present invention may include a radioprotectant such as human serum albumin (HSA) or ascorbate, which minimize radiolysis due to yttrium or other strong radionuclides. Other radioprotectants are known in the art and can also be used in the formulation buffer of the present invention, i.e., free radical scavengers (phenol, sulfites, glutathione, cysteine, gentisic acid, nicotinic acid, ascorbyl palmitate, HOP(:O)H$_2$I glycerol, sodium formaldehyde sulfoxylate, Na$_2$S$_2$0., Na$_2$S$_2$0$_3$, and S0$_2$, etc.).

A provided kit is one useful for radiolabeling a chelator-conjugated protein or peptide with a therapeutic radioisotope for administration to a patient. The kit includes (i) a vial containing chelator-conjugated antibody, (ii) a vial containing formulation buffer for stabilizing and administering the radiolabeled antibody to a patient, and (iii) instructions for performing the radiolabeling procedure. The kit provides for exposing a chelator-conjugated antibody to the radioisotope or a salt thereof for a sufficient amount of time under amiable conditions, e.g., as recommended in the instructions. A radiolabeled antibody having sufficient purity, specific activity and binding specificity is produced. The radiolabeled antibody may be diluted to an appropriate concentration, e.g., in formulation buffer, and administered directly to the patient with or without further purification. The chelator-conjugated antibody may be supplied in lyophilized form.

Uses of the Invention

The antibodies have in vitro and in vivo diagnostic, therapeutic and prophylactic utilities. For example, these antibodies can be administered to cells in culture, e.g. in vitro or ex vivo, or in a subject, e.g., in vivo, to treat, prevent, and/or diagnose a variety of disorders, such as cancers (e.g., ovarian, breast, lung). More specifically, antibodies or antibody fragments of the invention and compositions comprising the provided antibodies or antibody fragment (e.g., immunoconjugates (e.g., coupled to cytotoxic agents), can be used to treat cancers (e.g., a cancer where the target protein is expressed in at least some of the cells, e.g., ovarian cancer, breast cancer, lung cancer). The antibodies or antigen binding fragments of the invention, and immunoconjugates or compositions comprising the antibodies or antigen binding fragments provided herein can be used to treat cancers (e.g., ovarian cancer, breast cancer, lung cancer) in which OV064 is expressed. The provided antibody or antigen binding fragments can furthermore be used in cancer immunotherapy by blocking tumor induced immune silencing to inhibit T-cell proliferation and activation. Furthermore, the anti-OV064 antibodies or antigen binding fragments provided and compositions comprising same can also be used to diagnose and determine what cancers to be treated.

As used herein, the term "subject" is intended to include human and non-human animals. For example, a subject includes a patient (e.g., a human patient, a veterinary patient), having a disorder characterized by an OV064-expressing cell (e.g., a cancer cell). The term "non-human animals" of the invention includes all vertebrates, e.g., mammals and non-mammals, such as non-human primates, sheep, dog, cow, chickens, amphibians, reptiles, etc.

In one embodiment, the subject is a human subject. Alternatively, the subject can be a mammal expressing an OV064 antigen with which a antibody of the invention cross-reacts. An antibody or an antigen binding fragment molecule of the invention can be administered to a human subject for therapeutic purposes. Moreover, an anti-OV064 antibody, or fragment thereof can be administered to a non-human mammal expressing the OV064-like antigen with which the antibody cross-reacts (e.g., a primate, pig or mouse) for veterinary purposes or as an animal model of human disease. Animal models may be useful for evaluating the therapeutic efficacy of antibodies of the invention (e.g., testing of dosages and time courses of administration).

In one embodiment, the invention provides a method of inhibiting OV064-mediated cell signaling or a method of killing a cell. The method may be used with any cell or tissue which expresses OV064 such as a cancerous cell, (e.g., an ovarian cancer, breast cancer, pancreatic cancer, lung cancer cell), or a metastatic lesion (e.g., a cell found in renal, urothelial (e.g., bladder), testicular, colon, rectal, lung (e.g., non-small cell lung carcinoma), breast, liver, neural (e.g., neuroendocrine), glial (e.g., glioblastoma), pancreatic (e.g., pancreatic duct) cancer and/or metastasic melanoma (e.g., malignant melanoma), or soft tissue sarcoma). Methods of the invention include the steps of contacting the cell, with a anti-OV064 antibody or antigen binding fragment as described herein, or an immunoconjugate or composition comprising an anti-OV064 antibody or antigen binding fragment thereof, in an amount sufficient to inhibit OV064-mediated cell signaling or an amount sufficient to kill the cell. In methods of killing a cell, the method comprises using an immunoconjugate comprising an anti-OV064 antibody or antigen binding fragment thereof and a cytotoxic moiety.

The subject method can be used on cells in culture, e.g. in vitro or ex vivo. For example, cells which express OV064 such as cancer cells (e.g., malignant ovarian, breast, pancreatic or lung cancer cells), metastatic cells (e.g., renal, an urothelial, colon, rectal, lung, ovarian, breast, lung, pancreas, endometrial, or liver, cancerous or metastatic cells), or recombinant cells which express OV064, can be cultured in vitro in culture medium and the contacting step can be effected by adding the anti-OV064 antibody or fragment thereof, to the culture medium. The method can be performed on cells present in a subject, as part of an in vivo (e.g., therapeutic) protocol. For in vivo embodiments, the contacting step is effected in a subject and includes administering an immunoconjugate comprising an anti-OV064 antibody or fragment thereof and a cytotoxic moiety to the subject under conditions effective to permit both binding of the antibody or fragment to the extracellular domain of OV064 expressed on the cell, and the treating of the cell.

Examples of disorders that can be treated include, but are not limited to, ovarian cancer, breast cancer, lung cancer, pancreatic cancer, endometrial cancer, or metastases thereof, or any cancerous disorder which includes at least some expressing OV064 antigen. As used herein, the term "cancer" is meant to include all types of cancerous growths or oncogenic processes, metastatic tissues or malignantly transformed cells, tissues, or organs, irrespective of histopathologic type or stage of invasiveness. The terms cancer or tumor, may be used interchangeably (e.g., used in the context of "treatment of a cancer" or "treatment of a tumor").

Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting ovarian, lung, pancreas, lymphoid, and genitourinary tract (e.g., endometrial). Adenocarcinomas include malignancies such as non-small cell carcinoma of the lung. Metastatic lesions of the aforementioned cancers can also be treated or prevented using the methods and compositions of the invention. The subject method can be useful in treating malignancies of the various organ systems, such as those affecting those previously described. Additionally, the subject method can be useful in treating a relevant disorder at any stage or subclassification. For example, the subject method can be useful in any of stage 0 breast cancer patients, stage I breast cancer patients, stage IIA breast cancer patients, stage IIB breast cancer patients, stage IIIA breast cancer patients, stage IIIB breast cancer patients, stage IV breast cancer patients, grade I breast cancer patients, grade II breast cancer patients, and grade III breast cancer patients, as well as in malignant breast cancer patients, ductal carcinoma breast cancer patients, and lobular carcinoma breast cancer patients.

Methods of administering antibody molecules are described above. Suitable dosages of the molecules used will depend on the age and weight of the subject and the particular compound used. The antibody molecules can be used as competitive agents for ligand binding to inhibit, reduce an undesirable interaction (e.g., reduce immunosuppressive effects of OV064 mediated signaling).

In one embodiment, the anti-OV064 antibodies, or antigen-binding fragments thereof, can be used to kill or suppress cancerous cells in vivo. For example, the anti-OV064 antibodies can be used to treat a disorder described herein. The antibodies, or fragments thereof can be used by themselves or conjugated to a second agent, e.g., a cytotoxic agent, radioisotope, a pro-drug, or a protein, e.g., a protein toxin or a viral protein. This method includes: administering the antibody, alone or an immunoconjugate where the antibody or antigen binding fragment is conjugated to a cytotoxic agent, to a subject requiring such treatment.

The antibodies of the present invention may be used to deliver a variety of agents, e.g., a therapeutic agent, a drug, a radioisotope, molecules of plant, fungal, or bacterial origin, biological proteins (e.g., protein toxins) or particles (e.g., a recombinant viral particles, e.g., via a viral coat protein), or mixtures thereof. A therapeutic agent can be an intracellularly active drug or other agent, such as short-range radiation emitters, including, for example, short-range, high-energy α-emitters, as described herein. In some embodiments, the anti-OV064 antibody, or antigen binding fragment thereof, can be coupled to a molecule of plant or bacterial origin (or derivative thereof), e.g., a maytansinoid (e.g., maytansinol, e.g., DM1 or DM4 maytansinoid). DM1 is a sulfhydryl-containing derivative of maytansine that can be linked to antibodies via a disulfide linker that releases DM1 when inside target cells. The disulfide linkers display greater stability in storage and in serum than other linkers. Maytansine is a cytotoxic agent that effects cell killing by preventing the formation of microtubules and depolymerization of extant microtubules. It is 100- to 1000-fold more cytotoxic than anticancer agents such as doxorubicin, methotrexate, and vinca alkyloid, which are currently in clinical use. In other examples, the anti-OV064 antibody, or antigen binding fragment thereof, can be coupled to a taxane, an auristatin, a duocarmycin, a calicheamicin, or a derivative thereof. Additionally, anti-OV064 antibody or antigen binding fragment thereof can be coupled to a proteosome inhibitor or a topoisomerase inhibitor. For example, [(1R)-3-methyl-1-[[(2S)-1-oxo-3-phenyl-2-[(3-mercaptoacetyl)amino]propyl]amino] butyl]Boronic acid is a suitable proteosome inhibitor, and N,N'-bis[2-(9-methylphenazine-1-carboxamido)ethyl]-1,2-ethanediamine is a suitable topoisomerase inhibitor.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. In a provided embodiment, the anti-OV064 antibody is conjugated to maytansinoids, e.g., maytansinol (see U.S. Pat. No. 5,208,020), CC-1065 (see U.S. Pat. Nos. 5,475,092, 5,585,499, 5,846, 545). Procedures for preparing enzymatically active polypeptides of the immunotoxins are described in WO84/03508 and WO85/03508, which are hereby incorporated by reference. Examples of cytotoxic moieties that can be conjugated to the antibodies include adriamycin, chlorambucil, auristatin E, daunomycin, duocarmycin and analogs thereof, methotrexate, neocarzinostatin, and platinum.

To kill or suppress tumor cells, a first antibody, e.g., an antibody or an antigen binding fragment can be conjugated with a prodrug which is activated only when in close proximity with a prodrug activator. The prodrug activator is conjugated with a second antibody, e.g., a second antibody according to the present invention, preferably one that binds to a non-competing site on the OV064 molecule. Whether two antibodies bind to competing or non-competing binding sites can be determined by conventional competitive binding assays. Drug-prodrug pairs suitable for use in the practice of the present invention are described in Blakely et al., "ZD2767, an Improved System for Antibody-directed Enzyme Prodrug Therapy That Results in Tumor Regressions in Colorectal Tumor Xenografts," (1996) *Cancer Research*, 56:3287-3292, which is hereby incorporated by reference.

Alternatively, the antibody, e.g., the antibody, can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303-316 (Academic Press 1985), which is hereby incorporated by reference. Other suitable radioisotopes include α-emitters, such as $^{212}$Bi, $^{213}$Bi, and $^{211}$At, and β-emitters, such as $^{186}$Re and $^{90}$Y. Moreover, Lu$^{117}$ may also be used as both an imaging and cytotoxic agent.

Radioimmunotherapy (RIT) using antibodies labeled with $^{131}$I, $^{90}$Y, and $^{177}$Lu is under intense clinical investigation. There are significant differences in the physical characteristics of these three nuclides and as a result, the choice of radionuclide can be important in order to deliver maximum radiation dose to the tumor. The higher beta energy particles of $^{90}$Y may be good for bulky tumors, but it may not be necessary for small tumors and especially bone metastases. The relatively low energy beta particles of $^{131}$I are ideal, but in vivo dehalogenation of radioiodinated molecules is a major disadvantage for internalizing antibody. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the tumor residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers. (Mulligan T et al. *Clin Cancer Res.* 1: 1447-1454 (1995); Meredith R F, et al. *J Nucl Med* 37:1491-1496(1996); Alvarez R D, et al. *Gynecologic Oncology* 65: 94-101(1997)).

The antibodies of the invention can also be conjugated or fused to viral surface proteins present on viral particles. For example, a single-chain anti-OV064 antibody of the present invention could be fused (e.g., to form a fusion protein) to a viral surface protein. Alternatively, a whole anti-OV064 antibody of the present invention, or a fragment thereof, could be chemically conjugated (e.g., via a chemical linker) to a viral surface protein. Preferably, the virus is one that fuses with endocytic membranes, e.g., an influenza virus, such that the virus is internalized along with the anti-OV064 antibody and thereby infects OV064-expressing cells. The virus can be genetically engineered as a cellular toxin. For example, the virus could express or induce the expression of genes that are toxic to cells, e.g., cell death promoting genes. Preferably, such viruses would be incapable of viral replication.

The antibodies or antigen binding fragments, of the present invention can be used and sold together with equipment, as a kit, to detect the particular label.

The antibodies, e.g., the antibodies, or antigen-binding portions thereof, of the present invention bind to extracellular domains of OV064 or portions thereof in cells expressing the antigen. As a result, when practicing the methods of the present invention to kill, suppress, or detect cancerous cells, the antibodies or antigen binding fragments, bind to all such cells, not only to cells which are fixed or cells whose intracellular antigenic domains are otherwise exposed to the extracellular environment. Consequently, binding of the antibodies or antigen binding fragments, is concentrated in areas where there are cells expressing OV064, irrespective of whether these cells are fixed or unfixed, viable or necrotic. Additionally or alternatively, these antibodies, or antigen binding fragments thereof, bind to and are internalized with OV064 upon binding cells expressing the antigen.

The anti-OV064 antibodies described herein, e.g., the anti-OV064 antibodies, or antigen-binding fragments thereof, may be used in combination with other therapies. For example, the combination therapy can include a composition of the present invention co-formulated with, and/or co-administered with, one or more additional therapeutic agents, e.g., one or more anti-cancer agents, e.g., cytotoxic or cytostatic agents, homone treatment, vaccines, and/or other immunotherapies. In other embodiments, the anti-OV064 antibodies are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

When used in combination with one or more additional therapeutic agents, e.g., one or more anti-cancer agents, e.g., cytotoxic or cytostatic agents, homone treatment, vaccines, and/or other immunotherapies, the selected agent or agents depend on the disorder being treated. The additional agent(s) may include, for example, a combination with standard approved therapeutic for the indication being treated (e.g., platinum (e.g., carboplatin, cisplatin, anthracyclines (e.g., doxorubicin, epirubicin), taxanes (e.g., paclitaxel, docetaxel), topoisomerase inhibitors (e.g., topotecan, irinotecan, etoposide), vinca alkaloids (e.g., vinorelbine), immunotherapies (e.g., Herceptin), hormone therapy).

Labeled antibodies can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen Thus, in another aspect, the present invention provides a diagnostic method for detecting the presence of an OV064 protein in vitro (e.g., in a biological sample, such as a tissue biopsy, e.g., from a tumor tissue) or in vivo (e.g., in vivo imaging in a subject). The method includes: (i) contacting the sample with a anti-OV064 antibody or fragment thereof, or administering to the subject, the anti-OV064 antibody; (optionally (ii) contacting a reference sample, e.g., a control sample (e.g., a control biological sample, such as plasma, tissue, biopsy) or a control subject)); and (iii) detecting formation of a complex between the anti-OV064 antibody, and the sample or subject, or the control sample or subject, wherein a change, e.g., a statistically significant change, in the formation of the complex in the sample or subject relative to the control sample or subject is indicative of the presence of OV064 in the sample.

Preferably, the anti-OV064 antibody (or fragment thereof) is directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

Complex formation between the anti-OV064 antibody and OV064 can be detected by measuring or visualizing either the antibody (or antibody fragment) bound to the OV064 antigen or unbound antibody (or antibody fragment). Conventional detection assays can be used, e.g., an enzyme-linked immunosorbent assays (ELISA), an radioimmunoassay (RIA) or tissue immunohistochemistry. Alternative to labeling the anti-OV064 antibody, the presence of OV064 can be assayed in a sample by a competition immunoassay utilizing standards labeled with a detectable substance and an unlabeled anti-OV064 antibody. In this assay, the biological sample, the labeled standards and the OV064 binding agent are combined and the amount of labeled standard bound to the unlabeled antibody is determined. The amount of OV064 in the sample is inversely proportional to the amount of labeled standard bound to the OV064 binding agent.

In still another embodiment, the invention provides a method for detecting the presence of OV064-expressing tumor tissues in vivo. The method includes (i) administering to a subject (e.g., a patient having a cancer) an anti-OV064 antibody or antigen binding fragment thereof, preferably a antibody or antigen binding fragment thereof conjugated to a detectable label or marker; (ii) exposing the subject to a means for detecting said detectable label or marker to the OV064-expressing tissues or cells.

Examples of labels useful for diagnostic imaging in accordance with the present invention are radiolabels such as $^{131}I$, $^{111}In$, $^{123}I$, $^{99m}Tc$, $^{32}P$, $^{125}I$, $^{3}H$, $^{14}C$, and $^{188}Rh$, fluorescent labels such as fluorescein and rhodamine, nuclear magnetic resonance active labels, positron emitting isotopes detectable by a single photon emission computed tomography ("SPECT") detector or positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. The antibody can be labeled with such reagents using techniques known in the art. For example, see Wensel and Meares (1983) *Radioimmunoimaging and Radioimmunotherapy*, Elsevier, New York, which is hereby incorporated by reference, for techniques relating to the radiolabeling of antibodies. See also, D. Colcher et al. *Meth. Enzymol.* 121: 802-816 (1986), which is hereby incorporated by reference.

In the case of a radiolabeled antibody, the antibody is administered to the patient, is localized to the tumor bearing the antigen with which the antibody reacts, and is detected or "imaged" in vivo using known techniques such as radionuclear scanning using e.g., a gamma camera or emission tomography or computed tomography. See e.g., A. R. Bradwell et al., "Developments in Antibody Imaging", *Monoclonal Antibodies for Cancer Detection and Therapy*, R. W. Baldwin et al., (eds.), pp 65-85 (Academic Press 1985), which is hereby incorporated by reference. Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

Fluorophore and chromophore labeled antibodies can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescent compounds and chromophores are described by Stryer *Science*, 162:526 (1968) and Brand, L. et al. *Annual Review of Biochemistry*, 41:843-868 (1972), which are hereby incorporated by reference. The antibodies can be labeled with fluorescent chromophore groups by conventional procedures such as those disclosed in U.S. Pat. Nos. 3,940,475, 4,289,747, and 4,376,110, which are hereby incorporated by reference.

One group of fluorescers having a number of the desirable properties described above is the xanthene dyes, which include the fluoresceins derived from 3,6-dihydroxy-9-henylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

In other embodiments, the invention provide methods for determining the dose, e.g., radiation dose, that different tissues are exposed to when a subject, e.g., a human subject, is administered an anti-OV064 antibody that is conjugated to a radioactive isotope. The method includes: (i) administering an anti-OV064 antibody as described herein, e.g., a anti-OV064 antibody, that is labeled with a radioactive isotope to a subject; (ii) measuring the amount of radioactive isotope located in different tissues, e.g., tumor, or blood, at various time points until some or all of the radioactive isotope has been eliminated from the body of the subject; and (iii) calculating the total dose of radiation received by each tissue analyzed. The measurements can be taken at scheduled time points, e.g., day 1, 2, 3, 5, 7, and 12, following administration (at day 0) of the radioactively labeled anti-OV064 antibody to the subject. The concentration of radioisotope present in a given tissue, integrated over time, and multiplied by the specific activity of the radioisotope can be used to calculate the dose that a given tissue receives. Pharmacological information generated using anti-OV064 antibodies labeled with one radioactive isotope, e.g., a gamma-emitter, e.g., $^{111}In$, can be used to calculate the expected dose that the same tissue would receive from a different radioactive isotope which cannot be easily measured, e.g., a beta-emitter, e.g., $^{90}Y$.

Deposits

Purified plasmid DNA comprising DNA sequences encoding the heavy and light chains of each of the human monoclonal antibodies mAb sc77, mAb sc189, and mAb sc209 were deposited on Nov. 10, 2004, on behalf of Millennium Pharmaceuticals, Inc., 40 Landsdowne St., Cambridge, Mass. 02139, U.S.A., at the American Type Culture Collection, P.O. Box 1549, Manassas, Va. 20108, U.S.A., under Accession Nos. PTA-6294 (Ov64sc77), PTA-6295 (Ov64sc189), and PTA-6296 (Ov64sc209). The deposits have been made pursuant to, and in satisfaction of, the requirements of the Budapest Treaty on the International Recognition of the Deposit of Microorganisms for the Purposes of Patent Procedure.

Hybridoma cell lines producing mouse monoclonal antibodies mAb 4G10, mAb 8G5, mAb 3A4 and mAb 2F3 were deposited on Dec. 1, 2004, on behalf of Millennium Pharmaceuticals, Inc., 40 Landsdowne St., Cambridge, Mass. 02139, U.S.A., at the American Type Culture Collection, P.O. Box 1549, Manassas, Va. 20108, U.S.A., under Accession Nos. PTA-6402 (4G10), PTA-6403 (8G5), PTA-6401 (3A4), and PTA-6400 (2F3). The deposits have been made pursuant to, and in satisfaction of, the requirements of the Budapest Treaty on the International Recognition of the Deposit of Microorganisms for the Purposes of Patent Procedure.

The present invention is illustrated by the following examples, which should not be construed as further limiting. The contents of all references, pending patent applications and published patents, cited throughout this application are hereby expressly incorporated by reference.

EXAMPLES

Example 1

Generation of Anti-Ov064 Antibodies and Characterization

Generation of OV064 Protein for Immunization and Screening: Ov064 antigen was prepared by subcloning amino acids 32-257 (RGSHHHHHHSGRHSITVTTVASAGNI-GEDGILSCTFEPDIKLSDIVIQWLKEGVLGLVH EFKEGKDELSEQDEMFRGRTAV-FADQVIVGNASLRLKNVQLTDAGTYKCYIITSKGK GNANLEYKTGAFSMPEVNVDYNASSETL-RCEAPRWFPQPTVVWASQVDQGANFSEV SNTS-FELNSENVTMKVVSVLYNVTINNTYSC-MIENDIAKATGDIKVTESEIKRRSHLQL LNSK (SEQ ID NO:45)) of OV064 (OV064 sequence in bold) into an expression vector such as pET (Novagen, San Diego, Calif.) and expressed recombinantly in E. coli with a N-terminal 6×-His tag for purification (italic). The protein was purified over a Ni-column according to standard protocols as outlined by the manufacturer (Qiagen, Valencia, Calif.).

For screening of hybridoma supernatants and purified mAbs by ELISA, the nucleic acid encoding the following fusion construct was cloned into pCMV1 expression vector (Sigma): DYKDDDDKLAAANSLIIGFGIS-GRHSITVTTVASAGNIGEDGILSCTFEPDIKLSDIVIQW LKEGVLGLVHEFKEGKDELSEQDEMFR-GRTAVFADQVIVGNASLRLKNVQLTDAGT YKCYI-ITSKGKGNANLEYKTGAFSMPEVNVDY-NASSETLRCEAPRWFPQPTVVWASQ VDQGANFSEVSNTSFELNSENVTMKVVS-VLYNVTINNTYSCMIENDIAKATGDIKVTE SEIKRRSHLQLLNSKHHHHHH (SEQ ID NO:46). Purification tags: FLAG-tag (in the N-terminus) and His-tag (in the C-terminus) were cloned into the construct as well and are noted italics. The OV064 sequence amino acids 32-257 is depicted in bold. The fusion protein construct was transfected into 293 cells, expressed, and recombinant protein was purified over and Anti-FLAG® M2-Agarose Affinity column (Sigma).

Reagents and Cell Lines. ES-2 ovarian carcinoma cells and SKBR-3 breast carcinoma cells were obtained from ATCC and maintained according to ATCC protocols. OV064(32-282) was subcloned into pCMV-3 expression vector (Sigma), similar to above. ES-2_OV064 cells were generated by transfecting OV064(32-282) into wild type ES-2 cells. Cells were analyzed for OV064 expression by flow cytometry and western blot using the antibodies described below. Goat anti-mouse (GAM)-IgG1-DM1, GAM-IgG2b-DM1, mouse anti-human (MAH)-IgG-DM1, and anti-OV064-DM1 were generated according to a one-step process for the production of cytotoxic conjugates of maytansinoids as described in U.S. Pat. No. 6,441,163.

Briefly, maytansinoids having a disulfide moiety that bears a reactive group are linked to cell binding agents, such as antibodies, without prior modification of the cell binding agent. Conjugated antibody is prepared by disulfide exchange between the (2-trimethylsilyl)ethyl ester of PPA (5) and N-methyl-N-(3-mercapto-1-oxopropyl)-L-alanine. Prepared antibody is concentrated by tangential flow filtration (10 kD NMWCO membranes) and diafiltered against 50 mM potassium phosphate, 2 mM EDTA, pH 6.0. Concentrated antibody is filtered through a filter, if opalescent, and then modified with N-succinimidyl 4-(2-pyridyldithio)propionate (SPP) at a concentration of 20-22 mg/ml antibody and 7 molecules of SPP per molecule of antibody. Modification is done in 50 mM potassium phosphate, 2 mM EDTA, 5% ethanol, pH 6.0, for 2.5+/−0.5 hours. The modification vessel is a 500 ml round bottom flask. modified antibody is separated from the reaction mixture of step 2) using gel filtration chromatography and a Sephadex G25™ column. The column load represents about 25% of the column volume and the chromatography is done in 50 mM potassium phosphate, 2 mM EDTA, pH 6.0, at a flow rate of 50 cm/hr. The modified antibody elutes between 38-75% column volume. At a concentration of about 10 mg/ml, the modified antibody is conjugated with DM1 (using 1.7 molecules of DM1/molecule of SPP conjugated to the antibodies) for 20+/−4 hours. Typically, the reaction time is between 16.25 and 17.7 hours and is carried out in a 1 L round bottom glass flask equipped with a magnetic stirring bar. The conjugation reaction is done in 3% DMA, 10% sucrose (100 mg sucrose/ml of reaction). At the end of the reaction the conjugated antibody is filtered and a spectrophotometric reading is taken. Conjugated antibody is separated from unreacted DM1 by gel filtration chromatography using a Sephadex G25™ column.

GAM-IgG1 and GAM-IgG2b were purchased from Southern Biotechnology Company. MAH-IgG was purified from clone HP607 (CRL1753, ATCC).

Generation of murine mAbs by immunization: C57BL6/J mice were immunized with OV064 antigen (see above) and Complete Freund's Adjuvant (CFA). After two weeks, mice were boosted with OV064 antigen and Incomplete Freund's Adjuvant (IFA). Mice continued to receive booster shots containing antigen every 2 weeks until a significant antibody titer in the serum of the mice was detected. Upon reaching sufficient titer, mice were sacrificed and spleens were harvested and homogenized.

Hybridomas that produce murine mAb: Splenocytes from sacrificed C57BL6/J mice were fused to Ag8.35 myeloma cells to produce hybridomas and plated in HAT selection medium. Clones were screened for mAb production and subcloned by limiting dilution.

Generation of human mAbs. XENOMOUSE genetically engineered mice (Abgenix, Fremont, Calif.) (8 to 10 weeks old) were immunized for production of human monoclonal antibodies. See, Mendez et al. *Nature Genetics* 15:146-156 (1997), Green and Jakobovits *J. Exp. Med.* 188:483-495 (1998), the contents of which are incorporated by reference. Briefly, mice were immunized subcutaneously at the base of tails with OV064 antigen (see above) emulsified with complete Freund's adjuvant. In each case, the dose was repeated three or four times in incomplete Freund's adjuvant. Four days before fusion, the mice received a final injection of OV064 antigen. Spleen and/or lymph node lymphocytes from immunized mice were isolated from the mice and plated in plaque assays as described previously in Babcook et al., *Proc Natl Acad Sci USA*. 93: 7843-8 (1996), which is incorporated herein by reference. Briefly, cells were plated in agar with sheep red blood cells, coated with OV064 antigen and cells secreting mAb against the OV064 antigen would fix complement and lyse the red blood cells immediately surrounding the mAb producing cells. Cells within the cleared plaques were lifted and their immunoglobulin sequences were subcloned into expression vectors. The variable regions of the heavy and light chains for each of the single cell isolated for mAb sc77, mAb sc189 and mAb 209 were cloned as described by the methods in Babcook et al., *Proc Natl Acad Sci USA*. 93: 7843-8 (1996). The selected resulting constructs were cloned into adapted pcDNA3.1 (Invitrogen) as described, and constructs encoding these antibodies with a human IgG1 constant region were produced. Supernatants from transiently transfected cells containing OV064 specific mAb were subsequently screened by ELISA and for binding to cells by flow cytometry.

Generation of human expression mAb expression vectors. Each of the heavy and light chain variable regions for mAb sc77, mAb sc189 and mAb 209 was then cloned into an expression vector comprising both the heavy and light chain of each mAb. Briefly, primers were designed with specified cloning sites for PCR amplification of heavy and light chain sequences from the original vectors: 3' VH primers have Blp1 cloning site (underlined); 5' VH primers have EcoR1 cloning site (underlined); 3' VL primers have BsiW1 cloning site (underlined); and 5' VL primers have Not1 cloning site (underlined):

```
sc077 3' VH primer:
                                      (SEQ ID NO: 31)
AAAAAGAGAGCTGAGCTGACGGTGACCAGGGTTCCCTGG sc077 5' VH primer:
                                      (SEQ ID NO: 32)
AAAAACTCTGAATTCCTCACCATGGAGTTGGGACTGTGT sc077 3' VL primer:
                                      (SEQ ID NO: 33)
AAAAAGAGACGTACGTTTGATCTCCACTTTGGTCCCTCC sc077 5' VL primer:
                                      (SEQ ID NO: 34)
AAAAACTCTGCGGCCGCCTCACCATGGTGTTGCAGACCCAGGTC sc189 3' VH primer:
                                      (SEQ ID NO: 35)
AAAAAGAGAGCTGAGCTGACGGTGACCAGGGTTCCCTGG sc189 5' VH primer:
                                      (SEQ ID NO: 36)
AAAAACTCTGAATTCCTCACCATGGAATTTGGACTTCGC sc189 3' VL primer:
                                      (SEQ ID NO: 37)
AAAAAGAGACGTACGTTTAATCTCCAGTCGTGTCCCTTG sc189 5' VL primer:
                                      (SEQ ID NO: 38)
AAAAACTCTGCGGCCGCCTCACCATGAGGGTCCCTGCTCAG sc209 3' VH primer:
                                      (SEQ ID NO: 39)
AAAAAGAGAGCTGAGCTGACGGTGACCGTGGTCCCTTGG sc209 5' VH primer:
                                      (SEQ ID NO: 40)
AAAAACTCTGAATTCCTCACCATGGAGTTGGGGCTGTGC sc209 3' VL primer:
                                      (SEQ ID NO: 41)
AAAAAGAGACGTACGTTTGATTTCCACCTTGGTCCCTTG sc209 5' VL primer:
                                      (SEQ ID NO: 42)
AAAAACTCTGCGGCCGCCTCACCATGGAAACCCCAGCGCAG.
```

5' primers also contain a Kozak sequence in front of the ATG of the native human signal sequence of the antibodies. PCR was done with Invitrogen's Platinum Pfx DNA Polymerase (highest fidelity) cat. no. 11708-021 to amplify each of the human sequences. The resulting PCR products were digested and light chain variable region genes were cloned into the expression vector, pLKTOK58D, followed by insertion of the heavy chain variable region genes.

Expression vector pLKTOK58D contains an expression cassette, the design and generation of which have been described previously. See O'Keefe et al., U.S. Patent Application Publication No. 20040033561, published Feb. 19, 2004, which is incorporated herein by reference. Briefly, pLKTOK58D is a pcDNA3 based expression vector, which was engineered to replace the CMV promoter with an EF-1a promoter. The MfeI restriction site in the EF1a promoter was mutated by site directed mutagenesis. This intermediate expression vector also contains the BGH polyadenylation site following a multiple cloning site downstream of the promoter. Additionally, the DHFR resistance cassette with its own SV40 promoter and polyadenylation site was inserted into the expression vector to create pTOK10. The human heavy chain IgG1 constant region gene was inserted into the multiple cloning site between the EF1a promoter and the BGH polyadenylation site, resulting in a promoter, heavy chain, polyA cassette, with a cloning site allowing addition of variable sequence, creating pLKTOK55 Similarly, human light chain kappa constant region gene was engineered to introduce a silent BlpI mutation, and also inserted into the intermediate expression vector pLKTOK10. The entire region of promoter through polyA site of each of the heavy chain and light chain were combined in one vector, resulting in pLKTOK58D (see FIG. 1). The light chain cassette has cloning sites allowing for insertion of variable sequences in frame into NotI/BsiWI restriction sites, and the heavy chain cassette has cloning sites allowing for insertion of variable sequences in frame into EcoRI/BlpI restriction sites.

The resulting expression vectors contain each of the full length heavy and light chain genes under the control of the EF-1 alpha promoter. Both heavy and light chains also have BGH polyadenylation sites at their 3' ends. The vector also has two selection genes, neomycin and dihydrofolate reductase, for selection in transfected cell line of choice, such as, for example, CHO cells. The ampicillin gene is also in the expression vector for bacterial selection and growth, preferably, for example, an endonuclease and recombination negative strain (endA, recA) such as DH5alpha. Resulting expression vectors for each of the human antibodies mAb sc77 (Ov64sc77), mAb sc189 (Ov64sc189), and mAb sc209 (Ov64sc209) were deposited with the American Type Culture Collection as described above.

Analysis of mAb by ELISA. Microtiter plates were coated with 50 ul of recombinant OV064 in PBS at concentration of 1 μg/ml. Plates were covered with film and incubated overnight at room temperature, antigen was decanted from plates, and plates washed with phosphate buffered saline+1% Tween20. 200 ul per well of blocking solution (10% Nonfat dry milk in phosphate buffered saline) was added and incubated 1 hr at room temperature. 50 ul test reagent (either hybridoma supernatants, mouse serum or purified mAb) was added to the plate and incubated at room temperature. After 1 hr, plates were washed 3 times with phosphate buffered saline+1% Tween20, followed by addition of a working concentration of detection Ab (Anti-mouse or Anti-human horseradish peroxidase conjugate), usually diluted 1:5000 to 1:10000 in blocking buffer and incubated at room temperature. After 1 hr, plates were washed 3 times with phosphate buffered saline+1% Tween20. Bound anti-OV064 mAb was visualized with 3,3,5,5'-tetramehtylbenzidine (TMB) Substrate, and the reaction stopped with 2M $H_2SO_4$. Plates were read at 450 nm.

Analysis of mAb by flow cytometry. 50,000-100,000 test cells were prepared in 100 ul phosphate buffered saline+1% fetal bovine serum (PBSS). 50 ul of test reagent (either hybridoma supernatants, mouse serum or purified mAb) was added, and incubated 30-45 min on ice, then washed 2-3 times in PBSS. 50 ul of fluorescently labeled secondary antibody (Anti-Mouse IgG or Anti-Human IgG) was then added, and incubated 30-45 minutes on ice and washed. The cells were then resuspended in 300 ul of PBSS and analyzed by flow cytometer (FACSCalibur, Becton Dickinson) to assess amount of cell surface bound antibody.

PI-PLC Treatment of GPI linked cell surface proteins. Determination of release of GPI-linked proteins from cultured cells, was assessed using a 60 mm diameter culture dish, containing approximately $0.5.1 \times 106$ cells. The cell culture was rinsed twice with cold phosphate-buffered saline (PBS), then 0.5 mL of the same buffer containing 0.1.1.0 units of *B. cereus* Phosphatidylinositol-specific phospholipase C (PI-PLC) was added, and rocked at 4° for 20 minutes. Buffer was recovered for analysis of released proteins by western blot.

Internalization assay. Cells were plated in duplicate microtiter plates in complete medium and allowed to grow to about 40-50% confluency. Growth medium was removed and cells were placed on ice in PBSS. mAb was added to each well and incubated for 30 minutes on ice. Cells were washed 3 times in PBSS and after final wash 100 ul of PBSS were added. One of the plates was placed at 37 C and the other plate was left on ice and incubated for 1 hour. Cells were fixed in 4% formaldehyde and permeabilized in 1% Triton X-100, both in PBS. Working solutions of Fluorescently labeled secondary antibody (Anti-mouse IgG or Anti-Human IgG) was added to each well and incubated for 30 in on ice. Fluorescence was detected by microscopy.

Cytotoxicity assays. The ability of toxin conjugated anti-OV064 mAbs to kill OV064 expressing cells was tested. 1000-1500 cells were plated in complete medium (DMEM+10% FBS) and various concentrations of unconjugated, or DM1 or DM4 conjugated primary OV064 specific mAb. The ability of unconjugated primary OV064 specific mAb to kill OV064 expressing cells when bound to a DM1 or DM4 conjugated secondary antibody was also tested. Various concentrations of primary unconjugated OV064 specific mAbs were added to cells together with 5-10 nM of a relevant secondary DM1 conjugated antibody (Goat anti-mouse IgG or Mouse anti-human IgG). Cells were incubated for 96 hours. Cell death was measured by adding WST cell viability reagent. After 1-2 hour development the optical density in the wells was read at 650 nM.

Epitope mapping. A variety of techniques are available to determine epitopes specific for any particular antibody. For example, constructs of OV064 truncations were generated in a pCMV3 vector. Constructs representing amino acids 32-282, 133-282, 167-282 and 183-282 of the OV064 protein sequence were generated as N-terminally FLAG tagged proteins that when transfected into 293 cells, will be expressed on the cell surface. OV064 specific antibodies sc077, sc189, sc209 an 8G5 were tested for binding to these expressed constructs by flow cytometry, as described above. Furthermore, epitopes were analyzed using the Novatope system (Novagen Inc). Briefly, OV064 cDNA was treated with DNAse and fragments representing 15-600 bp were cloned into a bacterial expression vector. Each mAb was tested against 2000 clones representing OV064 fragments and each positive clone was picked and sequenced. The minimal common sequence between each of these clones was designated as the epitope to which each antibody bound. Additionally, a synthetic peptide map was utilized for identifying anti-OV064 epitopes. Briefly, 20 amino acid peptides each overlapping with 15 amino acids were printed on a nitrocellulose filter and incubated with anti-OV064 specific antibodies. Peptide spots that reacted strongly with the OV064 specific antibodies indicated the presence of an OV064 epitope.

Results:

Mouse monoclonal antibodies mAb 4G10, mAb 8G5, mAb 3A4 and mAb 2F3, were generated by traditional hybridoma technology. Human monoclonal antibodies sc77, sc189 and sc209 were generated using transgenic mice that generate fully human IgG1 antibodies, utilizing Abgenix XENOMAX transgenic technology. Specificity of the antibodies against OV064 was tested by ELISA and flow cytometry (FCM). A subset of the generated antibodies was selected for further characterization.

Hybridoma cell lines producing mouse monoclonal antibodies mAb 4G10, mAb 8G5, mAb 3A4 and mAb 2F3 were deposited on Dec. 1, 2004, on behalf of Millennium Pharmaceuticals, Inc., 40 Landsdowne St., Cambridge, Mass. 02139, U.S.A., at the American Type Culture Collection, P.O. Box 1549, Manassas, Va. 20108, U.S.A., under Accession Nos. PTA-6402 (4G10), PTA-6403 (8G5), PTA-6401 (3A4), and PTA-6400 (2F3).

The results of sequence analysis for each of the human monoclonal antibodies mAb sc77, mAb sc189, and mAb sc209 are listed in the sequence listing, and summarized in Table 1. Each of the sequences for nucleic acid (NA) and amino acid (AA) are described. The amino acid sequences for each of the heavy and light chains for the human monoclonal antibodies mAb sc77, mAb sc189 and mAb 209 is shown in Table 2.

TABLE 1

Summary of sequences for human monoclonal antibodies.

| mAb | IgG chain | NA SEQ ID | AA SEQ ID |
|---|---|---|---|
| Sc77 | Heavy chain | 1 | 2 |
| | Light chain | 3 | 4 |
| Sc189 | Heavy chain | 5 | 6 |
| | Light chain | 7 | 8 |
| Sc209 | Heavy chain | 9 | 10 |
| | Light chain | 11 | 12 |

TABLE 2

Amino acid sequence of human mAb

| | mAb | IgG chain | SEQ ID NO: | Amino Acid Sequence |
|---|---|---|---|---|
| 1 | Sc77 | Heavy chain | 2 | MELGLCWVFLVALLRGVQCQVQLVESGGGV VQPGRSLRLSCAASGFTFSSYGMHWVRQAP |

TABLE 2-continued

Amino acid sequence of human mAb

| mAb | IgG chain | SEQ ID NO: | Amino Acid Sequence |
|---|---|---|---|
| | | | GKGLEWVAVIWYDGNNKYYADSVKGRFTIS RDNSKNTLYLQMNSLRAEDTAVYYCARTSG IAAFDYWGQGTLVTVSSASTKGPSVFPLAP SSKSTSGGTAALGCLVKDYFPEPVTVSWNS GALTSGVHTFPAVLQSSGLYSLSSVVTVPS SSLGTQTYICNVNHKPSNTKVDKKVEPKSC DKTHTCPPCPAPELLGGPSVFLFPPKPKDT LMISRTPEVTCVVVDVSHEDPEVKFNWYVD GVEVHNAKTKPREEQYNSTYRVVSVLTVLH QDWLNGKEYKCKVSNKALPAPIEKTISKAK GQPREPQVYTLPPSRDELTKNQVSLTCLVK GFYPSDIAVEWESNGQPENNYKTTPPVLDS DGSFFLYSKLTVDKSRWQQGNVFSCSVMHE ALHNHYTQKSLSLSPGK |
| 2 | Sc77 Light chain | 4 | MVLQTQVFISLLLWISGAYGDNVMTQSPDS LAVFLGERATINCKSSQSVLYNSNYKNYLA WYQQKPGQPPKLLFYWASTRESGVPDRFSG SGSGTDFTLTISSLQAEDVAVYYCQQYYNT PLTFGGGTKVEIKRTVAAPSVFIFPPSDEQ LKSGTASVVCLLNNFYPREAKVQWKVDNAL QSGNSQESVTEQDSKDSTYSLSSTLTLSKA DYEKHKVYACEVTHQGLSSPVTKSFNRGEC |
| 3 | Sc189 Heavy chain | 6 | MEFGLRWVFLVAILEGVQCEVQLVESGGGL VQPGGSLRLSCAASGFSSSYDMHWVRQAT GKGLEWVSGIDIAGDTYYPGSVKGRFTISR ENAKNSLYLQMNSLRAGDTAVYYCARGDYD GTFDYWGQGTLVTVSSASTKGPSVFPLAPS SKSTSGGTAALGCLVKDYFPEPVTVSWNSG ALTSGVHTFPAVLQSSGLYSLSSVVTVPSS SLGTQTYICNVNHKPSNTKVDKKVEPKSCD KTHTCPPCPAPELLGGPSVFLFPPKPKDTL MISRTPEVTCVVVDVSHEDPEVKFNWYVDG VEVHNAKTKPREEQYNSTYRVVSVLTVLHQ DWLNGKEYKCKVSNKALPAPIEKTISKAKG QPREPQVYTLPPSRDELTKNQVSLTCLVKG FYPSDIAVEWESNGQPENNYKTTPPVLDSD GSFFLYSKLTVDKSRWQQGNVFSCSVMHEA LHNHYTQKSLSLSPGK |
| 4 | Sc189 Light chain | 8 | MRVPAQLLGLLMLWVPGSSGDIVMTQTPLS SPVTLGQPASISCRSSQSLVHSDGNTYLSW LQQRPGQPLRLLFYKISNRFSGVPDRFSGS GAGTDFTLIINRVEAEDVGVYYCMHATQFP ITFGQGTRLEIKRTVAAPSVFIFPPSDEQL KSGTASVVCLLNNFYPREAKVQWKVDNALQ SGNSQESVTEQDSKDSTYSLSSTLTLSKAD YEKHKVYACEVTHQGLSSPVTKSFNRGEC |
| 5 | Sc209 Heavy chain | 10 | MELGLCWLFLVAILEGVQCGVQLVESGGGL VQPGGSLRLSCAASGFTISRNDMHWVRQAT GKGLEWVSAIGTGGDTYYPGSVKGRFTISR ENAKNSLYLQMNSLRAGDTAVYYCARGHMT TFGGFIVIGNGMDVWGQGTTVTVSSASTKG PSVFPLAPSSKSTSGGTAALGCLVKDYFPE PVTVSWNSGALTSGVHTFPAVLQSSGLYSL SSVVTVPSSLGTQTYICNVNHKPSNTKVD KKVEPKSCDKTHTCPPCPAPELLGGPSVFL FPPKPKDTLMISRTPEVTCVVVDVSHEDPE VKFNWYVDGVEVHNAKTKPREEQYNSTYRV VSVLTVLHQDWLNGKEYKCKVSNKALPAPI EKTISKAKGQPREPQVYTLPPSRDELTKNQ VSLTCLVKGFYPSDIAVEWESNGQPENNYK TTPPVLDSDGSFFLYSKLTVDKSRWQQGNV FSCSVMHEALHNHYTQKSLSLSPGK |
| 6 | Sc209 Light chain | 12 | METPAQLLFLLLLWLPDTTGEIVMTQSPAT LSVSPGERATLSCRASQSVRSNLAWYQQKP GQAPRLLIYGASTRATGIPARFSGSGSGTE FTLTISSLQSEDFAVYSCQQYNNWPWTFGQ GTKVEIKRTVAAPSVFIFPPSDEQLKSGTA SVVCLLNNFYPREAKVQWKVDNALQSGNSQ ESVTEQDSKDSTYSLSSTLTLSKADYEKHK VYACEVTHQGLSSPVTKSFNRGEC |

Table 2, row 1 is an illustration of the encoded amino acid sequence of the mature heavy chain variable region of mAb sc77 (SEQ ID NO: 2); and the nucleic acid sequence encoding the mature heavy chain variable region of mAb sc77 is depicted in SEQ ID NO:1.

Complementarity determining region (CDR) 1 consists of amino acid residues 50-54 of SEQ ID NO: 2 (SEQ ID NO: 13), CDR 2 consists of amino acid residues 69-85 of SEQ ID NO: 2 (SEQ ID NO: 14), CDR 3 consists of amino acid residues 118-126 of SEQ ID NO: 2 (SEQ ID NO: 15).

Table 2, row 2 is an illustration of the encoded amino acid sequence of the mature light chain variable region of mAb sc77 (SEQ ID NO: 4); and the nucleic acid sequence encoding the mature kappa light chain variable region of mAb sc77 is depicted in SEQ ID NO: 3. Complementarity determining region (CDR) 1 consists of amino acid residues 44-59 of SEQ ID NO: 4 (SEQ ID NO: 22), CDR 2 consists of amino acid residues 76-82 of SEQ ID NO: 4 (SEQ ID NO: 23), CDR 3 consists of amino acid residues 115-123 of SEQ ID NO: 4 (SEQ ID NO: 24).

Table 2, row 3 is an illustration of the encoded amino acid sequence of the mature heavy chain variable region of mAb sc189 (SEQ ID NO: 6); and the nucleic acid sequence encoding the mature heavy chain variable region of mAb sc77 is depicted in SEQ ID NO:5. Complementarity determining region (CDR) 1 consists of amino acid residues 50-54 of SEQ ID NO: 6 (SEQ ID NO: 16), CDR 2 consists of amino acid residues 69-84 of SEQ ID NO: 6 (SEQ ID NO: 17), CDR 3 consists of amino acid residues 117-125 of SEQ ID NO: 6 (SEQ ID NO: 18).

Table 2, row 4 is an illustration of the encoded amino acid sequence of the mature light chain variable region of mAb sc189 (SEQ ID NO: 8); and the nucleic acid sequence encoding the mature kappa light chain variable region of mAb sc77 is depicted in SEQ ID NO: 7. Complementarity determining region (CDR) 1 consists of amino acid residues 44-59 of SEQ ID NO: 8 (SEQ ID NO: 25), CDR 2 consists of amino acid residues 75-82 of SEQ ID NO: 8 (SEQ ID NO: 26), CDR 3 consists of amino acid residues 114-122 of SEQ ID NO: 8 (SEQ ID NO: 27).

Table 2, row 5 is an illustration of the encoded amino acid sequence of the mature heavy chain variable region of mAb sc209 (SEQ ID NO: 10); and the nucleic acid sequence encoding the mature heavy chain variable region of mAb sc77 is depicted in SEQ ID NO:9. Complementarity determining region (CDR) 1 consists of amino acid residues 50-54 of SEQ ID NO: 10 (SEQ ID NO: 19), CDR 2 consists of amino acid residues 69-84 of SEQ ID NO: 10 (SEQ ID NO: 20), CDR 3 consists of amino acid residues 117-134 of SEQ ID NO: 10 (SEQ ID NO: 21).

Table 2, row 6 is an illustration of the encoded amino acid sequence of the mature light chain variable region of mAb sc209 (SEQ ID NO: 12); and the nucleic acid sequence encoding the mature kappa light chain variable region of mAb sc77 is depicted in SEQ ID NO: 11. Complementarity determining region (CDR) 1 consists of amino acid residues 44-54 of SEQ ID NO: 12 (SEQ ID NO: 28), CDR 2 consists of amino acid residues 70-76 of SEQ ID NO: 12 (SEQ ID NO: 29), CDR 3 consists of amino acid residues 109-117 of SEQ ID NO: 12 (SEQ ID NO: 30).

Expression vectors were created as described above which contain coding sequence for both the heavy and light chain of each of mAb sc77, mAb sc189, and mAb sc209. Purified DNA encoding the heavy and light chains of each of the human monoclonal antibodies mAb sc77, mAb sc189, and mAb sc209 were deposited on Nov. 10, 2004, on behalf of Millennium Pharmaceuticals, Inc., 40 Landsdowne St., Cambridge, Mass. 02139, U.S.A., at the American Type Culture Collection, P.O. Box 1549, Manassas, Va. 20108, U.S.A., under Accession Nos. PTA-6294 (Ov64sc77), PTA-6295 (Ov64sc189), and PTA-6296 (Ov64sc209).

The supernatants of hybridomas expressing murine IgG molecules 4G10, 8G5, 3A4, and 2F3 were tested for binding specificity to OV064 by flow cytometry, as well as ELISA analysis. mAb 4G10, mAb 8G5, mAb 3A4 and mAb 2F3 each bound transfected ES2 cells, expressing OV064, but none of these antibodies bound vector-control transfected ES2 cells that did not express OV064, indicating that the mAbs have binding specificity for OV064. Each mAb (mAb 4G10, mAb 8G5, mAb 3A4 and mAb 2F3) bound purified recombinant OV064-His, and OV064hFc fusion proteins in ELISA analysis. Table 3 summarizes the results of these analyses.

Similarly, supernatants as well as purified mAb from 293 cells transiently transfected with cDNA expressing human IgG molecules sc77, sc189, and sc209 were tested for binding specificity to OV064 by flow cytometry, as well as ELISA analysis. sc77, sc189, and sc209 each bound transfected ES2 cells, expressing OV064, but none of these antibodies bound vector-control transfected ES2 cells that did not express OV064, indicating that the mAbs have binding specificity for OV064. Each human mAb (mAb sc77, mAb sc189, and mAb sc209) bound purified recombinant OV064-His fusion protein in ELISA analysis. Table 3 summarizes the results of these analyses.

TABLE 3

Murine IgG and human IgG mAb which recognize OV064.

| | Flow cytometry screen | | ELISA screen | | |
|---|---|---|---|---|---|
| | ES2/OV064 | ES2/WT | OV064-His | OV064hFc | Neg control |
| 4G10 | + | − | + | + | − |
| 8G5 | + | − | + | + | − |
| 3A4 | + | − | + | + | − |
| 2F3 | + | − | + | + | − |
| Sc77 | ++ | − | + | ND | − |
| Sc189 | ++ | − | + | ND | − |
| Sc209 | ++ | − | + | ND | − |

The structure of Ov064 suggests that it potentially could be covalently linked to the cell surface via a glycosylphosphatidylinositol (GPI) linker, however, this has not yet been determined (Prasad et al., *Immunity* 18: 863-873 (2003); Zang et al., *Proc Natl Acad Sci USA* 100: 10388-10392 (2003) *Precursor proteins that are destined to be GPI anchored contain a GPI attachment signal at their extreme C terminus that is cleaved and replaced with a GPI moiety within the lumen of the ER.* To investigate whether Ov064 is a GPI-linked protein, cells expressing (ES-2_OV064) and cells not expressing (ES-2 wt) were treated with phosphatidylinositol-specific phospholipase (PI-PLC), a commonly used GPI anchor-cleaving enzyme, which releases GPI linked proteins into the supernatant. The presence of Ov064 was then analyzed by western blotting. OV064 was not detected in the supernatant of control treated ES-2_OV064 cells. In contrast, upon PI-PLC treatment Ov064 was readily detected in the supernatant, thus providing evidence that Ov064 is a GPI-linked cell surface protein.

To investigate whether mAbs to Ov064 would internalize in an antigen specific manner, cells expressing Ov064 (ES-2_OV064) were preincubated on ice with saturating concentrations of mAb. Excess mAb was washed away before cells were incubated for 1 hour at 37° C. Intracellular IgG was detected by immunofluorescence to visualize internalization. For each of mAb 4G10, mAb 8G5, mAb 3A4 and mAb 2F3, cells which were kept on ice, all of the Ov064 mAb was found on the cell surface of the cells and no intracellular mAb was detected. However when cells were incubated at 37° C., cytoplasmic IgG was readily detected internally for each of mAb 4G10, mAb 3A4, mAb 2F3 and mAb 8G5. This established that the antibody had been transported across the membrane most likely in complex with Ov064. No cell surface binding or internalization was seen in ES-2_Neo or ES-2 wt cells.

The ability of mAbs to Ov064 to deliver cytotoxic agents was assessed. Various concentrations of OV064 mAb were added to cells in microtiter plates, either alone as unconjugated mAb, together with DM1 conjugated anti-mouse IgG or anti-human IgG; or as directly DM1 conjugated mAb and incubated for 4 days as described in the Methods. Cell viability of OV064 expressing cells was determined and plotted against control cells that were not recognized by antibody. Anti-OV064 antibody alone does not have any effect on cell viability and neither does similar concentration of control antibody MAH-IgG-DM1.

TABLE 4

Cytotoxic effects of human IgG and mouse IgG mAbs specific for OV064.

| | ICA (EC50) | FCM (MFI max) | ELISA (EC50) | IgG Isotype |
|---|---|---|---|---|
| sc77 | 0.123 nM | 780 | ND | Human IgG1 |
| sc189 | 0.06 nM | 820 | ND | Human IgG1 |
| sc209 | 0.053 nM | 700 | ND | Human IgG1 |
| 4G10 | 3 nM | 350 | 0.1 µg/ml | Mouse IgG1 |
| 3A4 | 12 nM | 374 | 0.02 µg/ml | Mouse IgG1 |
| 2F3 | 0.66 nM | 138 | 0.03 µg/ml | Mouse IgG2b |
| 8G5 | >100 nM | 380 | 0.05 µg/ml | Mouse IgG1 |

However, when anti-Ov064 antibody was used in conjunction with the DM-1 conjugated anti-mouse IgG, cell killing was observed, resulting in EC50 of approximately 0.6-12 nM of the OV064 mAb. See Table 4. No cell killing was observed on cells that do not express OV064 that were treated with the same combination of mAb and toxin conjugated secondary antibody. Each of the murine and human mAbs were shown to bind to OV064 by ELISA and flow cytometry (FCM). See Table 3 and Table 4. When compared in cytotoxicity assays, however, there were some unexpected differences observed between the different mAb. Each of the mouse IgG 4G10, 3A4 and 2F3 and human IgG sc77, sc189, and sc209 could efficiently internalize and deliver toxic payloads into OV064 expressing cells, resulting in cell killing mAb 3A4 was shown to internalize in cells but required higher concentrations of the mAb to demonstrate identical levels of cytotoxic effects. In contrast, while mouse IgG 8G5 was able to bind with high affinity to recombinant protein and to cells expressing OV064, the mAb was completely unable to bring toxic payload into OV064 expressing cells. Thus, while each of the described mouse and human IgG molecules binds to OV064, and may be useful for detection of OV064 expression, only a subset of mAb specific for Ov064 are effective in delivery of toxic payloads into OV064 expressing cells. Similar results were found using primary OV064 mAbs that were directly conjugated with DM1. This effect does not appear to relate to affinity, as not all mAbs that bind with high affinity to OV064 could function as an effective immunoconjugate for killing tumor cells.

As described above in the methods, various approaches to determine epitope mapping of OV064 specific mAbs were used. Table 5 demonstrates results of the peptide binding experiments, which revealed sc77 binds an epitope comprising amino acids in the region of amino acids 167-176 of OV064; sc189 binds an epitope comprising amino acids in the region of amino acids 238-257 of OV064; sc209 binds an epitope comprising amino acids in the region of amino acids 177-181 of OV064, and 8G5 binds an epitope comprising amino acids in the region of amino acids 67-76 of OV064. The other methods confirmed the results depicted in Table 5.

TABLE 5

OV064 Epitope Mapping of IgG mAbs

| OV064 AA | sc77 | sc189 | sc209 | 8G5 |
|---|---|---|---|---|
| 32-51 | − | − | − | − |
| 37-56 | − | − | − | − |
| 42-61 | − | − | − | − |
| 47-66 | − | − | − | − |
| 52-71 | − | − | − | − |
| 57-76 | − | − | − | +++ |
| 62-81 | − | − | − | +++ |
| 67-86 | − | − | − | +++ |
| 72-91 | − | − | − | − |
| 77-96 | − | − | − | − |
| 82-101 | − | − | − | − |
| 87-106 | − | − | − | − |
| 92-111 | − | − | − | − |
| 97-116 | − | − | − | − |
| 102-121 | − | − | − | − |
| 107-126 | − | − | − | − |
| 112-131 | − | − | − | − |
| 117-136 | − | − | − | − |
| 122-141 | − | − | − | − |
| 127-146 | − | − | − | − |
| 132-151 | − | − | − | − |
| 137-156 | − | − | − | − |
| 142-161 | − | − | − | − |
| 147-166 | − | − | − | − |
| 152-171 | − | − | − | − |
| 157-176 | +++ | − | + | − |
| 162-181 | +++ | − | + | − |
| 167-186 | +++ | − | +++ | − |
| 172-191 | + | − | +++ | − |
| 177-196 | − | − | +++ | − |
| 182-201 | − | − | − | − |
| 187-206 | − | − | − | − |
| 192-211 | − | − | − | − |
| 197-216 | − | − | − | − |
| 202-221 | − | − | − | − |
| 207-226 | − | − | − | − |
| 212-231 | − | − | − | − |
| 217-236 | − | − | − | − |
| 222-241 | − | − | − | − |
| 227-246 | − | − | − | − |
| 232-251 | − | − | − | − |
| 237-256 | − | +++ | − | − |
| 238-257 | − | +++ | − | − |

Example 2

Anti-OV64 ADC Selectively Blocks Antigen Expressing Cells in G2/M

Materials and Methods. ES-2, ES-2 OV64 and SKBR3 human tumor cells were plated on 6 well dishes ($2\times10^5$/well; Falcon). Cells were cultured in McCoy's 5A medium (Gibco) supplemented with 10% bovine calf serum and 2 mM L-glutamine. After 18 hours, 209-DM4 or 209 was added directly to the cells at various concentrations (1.15, 2.5 and 6.5 nM) and the cells were grown an additional 6, 24 or 48 hrs. Cells treated with DMSO (0.2%) served as the untreated vehicle control and those treated with taxol or vincristine (100 nM) as the control for mitosis. The cells were harvested with Trypsin EDTA 1× (Gibco), washed 1× with phosphate buffered saline (PBS), fixed in 70% ethanol and stored at 4° for 1 hr. The cells were then resuspended in propidium iodide (1:40, Molecular Probes) and RNAse A (1:5000, Sigma) in PBS for 30 min at 4° C. Cell cycle distributions were determined by measuring DNA content using flow cytometry (FACSCalibur; Becton Dickenson) and samples were analyzed using Winlist software (Verity).

Results. To examine the affect of 209 and 209-DM4 on the cell cycle, DNA profiles were evaluated by flow cytometry. In the ES-2 cells overexpressing Ov64, treatment with 6.5 nM 209-DM4 for 24 hours induced an increase in 4N cells relative to control cells. At 48 hours a subG2 and subG1 scatter of cells was observed indicating apoptosis. In contrast ES-2 wt treated with 6.5 nM 209-DM-4 were similar to control at both 24 and 48 hours indicating that overexpression of Ov64 is necessary and responsible for sensitivity to 209-DM4. An increase in 4N cells upon treatment with 209-DM4 is consistent with inhibition mediated by DM4, a microtubule binder which is known to abrogate cell cycle progression at mitosis (4N DNA content) Both cell lines responded to treatment of 100 nM taxol with an equivalent increase in 4N cells indicating that the ES-2 cells are equally responsive to mitotic inhibitors. At 48 hrs the SKBR3 cells that express Ov64 endogenously demonstrated an increase in 4N cells.

Example 3

In Vitro Cytotoxicity of Anti-OV64 ADC

Materials and Methods. ES-2 wt and ES-2_OV64 cells were cultured to about 70-80% confluency and lifted with Versene and live cells were counted by Trypan Blue exclusion. Cells were collected in cold D-PBS or D-PBS/3% FBS/0.1% sodium azide buffer and resuspended in McCoy's/10% FBS (complete medium) to $2\times10^5$ cells/mL. Add 100 µL of cells suspension was added to each well of a 96-well fait bottomed plate (2000 cells per well). SKBR-3 cells were treated the same way except that 7500 cells were plated per well. The anti-OV64 ADC sc209-DM4 was diluted in complete medium in a 2-fold serial dilution. As controls, no ADC in complete medium was used. 100 µL of ADC dilutions was added to the cells in triplicate. The cells were incubated at 37° C., 5% CO2 for 96 hours. At the end of the incubation time the media was aspirated and a 10% WST in complete media was added. Plates were incubated at 37° C. for 1.5-2 hours and read on plate reader at OD 440/650.

Results. The cytotoxic effect of sc209-DM4 on ES-2WT and ES-2_Ov64 cells was calculated as per cent of control (no ADC added) cells. The LD50 for sc209-DM4 on ES-2_Ov64 cells is 2.5 nM whereas the LD50 for the ES-2WT cells was calculated to be >25 nM as calculated in ExcelFit.

Both the ES-2WT and ES-2_OV64 cells have similar sensitivity to free maytanisinoids (data not shown). However when DM4 is conjugated to sc209, the ES-2_OV64 cells are >10 fold more sensitive than the ES-2WT. Thus DM4 has been rendered target selective by conjugation to sc209 and selectively kill ATGOv064 expressing cells.

Although the level of ATGOv064 expression is significantly lower on the SKBR3 cells, the sensitivity to sc209-DM4 is not significantly different. The LD50 for SKBR3 was 4.4 nM (n=3) compared to 2.5 nM on ES-2_OV64. As a control for a non-binding DM4 conjugated antibody, SKBR-3 cells were incubated with 5H9-DM4, which does not bind to the SKBR3 cells.

Example 4

Radiolabeled Anti-Ov064 Antibody Selectively Localizes to Antigen Expressing Tumors In Vivo Materials and Methods DTPA conjugation. Antibodies were reconstituted in conjugation buffer (0.1 M sodium bicarbonate, pH 8.2) by Contricon (YM-30, Milipore) to obtain a 5 mg/ml solution of antibodies by ultrafiltration (Centricon® filter 30 kDa, Millipore at 5000 g). The chelator diethylenetriamine pentaacetic acid dianhydride (DTPA dianhydride, Sigma Chemical Co., St Louis, Mo., U.S.A.) was then conjugated to the antibody using a small modification of the well-known cyclic anhydride method. The conjugation condition was performed and optimized with human polyclonal immunoglobulin G (HIG, Sigma Chemical Co., St Louis, Mo., U.S.A.) at antibody: DTPA molar ratios of 1:1 to 1:50. The ratio of 1:10 was used for the later experiments. In brief, 5 µl of a 2.3 mg/ml suspension of DTPA anhydride in dry DMSO (Sigma-Aldrich) was added dropwise to test tubes containing 2 mg/0.4 ml antibody. The reaction was gently mixed and incubated at room temperature for 50 min Unbound DTPA was then removed by ultrafiltration (10 times 50 min at 4500×g). At end of the purification, the Ab solution was changed into labeling buffer (0.1 M sodium acetate buffer, NaOAc, pH 7.2). The purified immunoconjugate was measured for the protein concentration and dispensed into 160 ug/100 ul, either stored at −80° C. or immediately used for radiolabelling.

Radiolabelling. $^{111}$In, as $^{111}$InCl$_3$, was purchased from PerkinElmer, Boston in 370 MBq/ml in 0.05 M HCl, pH 1.5-1.9. The $^{111}$InCl$_3$ was added to the conjugated DTPA-Ab and the reaction mixture was incubated for 5 min. The product was diluted in normal saline to the desired specific activity. After the LE and RCP were measured, the resulting $^{111}$In-DTPA was sterilised by filtration through a 0.2 µm syringe filter (Millipore).

The complete labelling procedure was optimised by subsequently varying reaction pH, incubation times, molar DTPA to antibody ratios, amounts of $^{111}$InCl$_3$ added per mg conjugate and QC methods with a Sephadex G25 column (PD-10 column, Amersham Biosciences AB, Uppsala, Sweden) versus ITLC. Initially, purification methods with a Sephadex G25 column (PD-10 column, Amersham Biosciences AB, Uppsala, Sweden) versus ultrafiltration was planned to removed the unlabeled $^{111}$In. Then, the one-step instant labeling method was developed, which can achieve the LE up to 97%, and the RCP remains that level 5 days after the labeling. The labeling can be achieved by a simple addition of required amount of $^{111}$InCl$_3$ to the vials containing known amount of immunoconjugates.

Dual-Tumor Animal Model. The parental ES-2 human ovarian cell line and the Ov64 transfected ES-2 line (ES-2Ov64) were grown in culture at 37° C. in a humidified 5% $CO_2$ incubator in McCoy 5a medium with 10% FBS. Xenografts were established in 25 gram (g) female BALB/c nu/nu mice, 8-10 weeks of age with the implantation of 2×10$^6$ ES-2 or ES-2Ov64 cells into the left and right rear dorsum subcutis, respectively. In a pilot study, tumor growth kinetics of the two tumors grown in the same animal were evaluated by measuring the tumor sizes over time and the two tumors shared similar growth kinetics (data not shown).

Tumor growth was monitored with caliper measurements; tumor volume was calculated using the formula $V=W^2 \times L/2$ Animals were randomized into 3 groups of 30 animals (5 animals per timepoint) with tumor sizes of 100-300 mg (5-8 mm diameter) on both tumors.

Biodistribution and Tumor Uptake Studies. Tumor-bearing mice were injected i.v. via a lateral vein with 0.1 ml of $^{111}$In-Abs, specifically, SC189, SC209 and the control HIG at 300 µCi/15 µg/100 µl. Ninety animals were injected as: 5 (animals per group)×3 antibodies×6 timepoints (5 min, 4, 24, 48, 120 and 168 h). At the preset time points after injection, mice were sacrificed by $CO_2$. Blood was drawn by cardiac puncture immediately after euthanasia, and the following tissues were obtained by dissection: tumors, liver, kidneys, spleen, lungs, heart, stomach, small intestines, large intestines, muscle, pancreas, and ovaries. Tissues were weighed, and the radioactivity was measured using an automatic gamma counter with decay correction (PerkinElmer). Aliquots of the dose solution were also counted to determine the total radioactivity administered. The counts were then standardized for tissue mass and expressed as a percentage of the total activity injected into each mouse per gram tissue (% ID/g).

Whole body clearance. In the first batch of pilot study, the whole-body clearance was measured. After injection of control HIG or Sc209, the whole body radioactivity was measured by placing the animal into a dose calibrator. While clinical PK is measured by the elimination, we measure the retention of radioactivity. With periodic measurements, we can calculate the effective half-life of the radiolabeled antibodies ($T_{1/2\ eff}$). The biological halflife ($T_{1/2\ bio}$) can be computed by the following equation: $1/T_{1/2\ eff}=1/T_{1/2\ bio}+1/T_{1/2\ phy}$, where $T_{1/2\ phy}$ is the physical half-life of the radiolabel (67 hrs for 111In). Animals were evaluated for whole body radioactivity at the following timepoints: 0, 4, 24, 48, and 120 hrs.

Imaging. One of 5 euthanized animals from each group at each time point was imaged anteriorly with a bench-top scintillation camera (Gamma Imager, Biospace, France) with a medium energy collimator.

Autoradiography. After imaging, one euthanized mouse from each group was subjected to whole-body autoradiography to reveal the interior distribution of labeled Ab and to compensate for the insufficient spatial resolution of the planar scintigraphic imaging. Briefly, immediately after imaging, animals were snap frozen by dry-ice-cooled ethanol, then embedded in a frame containing 4% Carboxymethyl cellulose in water (Sigma-Aldrich). The embedded animals were frozen in −80° C. overnight shielded with lead. Then the sample (whole body) was mounted on an existing cryomicrotome and brought to thermal equilibrium (−20° C.) for at least 2 hrs. The block was then sliced into coronal sections 40 µm thick. Sections were immobilized on tape (Type 810, Leica Inc., Deerfield, ILK) and left in the instrument to freeze-dry. After 8 hrs, the tapes with tissues were set in contact with a Phosphor screen (Fuji imaging) and exposed for 72 hrs, then scanned in a PhosphorImager Fuji scanner to generate a digitized image.

Results

This study was performed to determine the in vivo biodistribution of the Ov64 Sc209 and Sc189 human monoclonal antibodies by imaging tumor bearing mice. The Ov64 antibodies and a control polyclonal human immunoglobulin G (HIG) were radiolabeled with 111In using DTPA as a bifunctional chelator. The in vivo behavior, including tumor targeting and biodistribution in normal tissues over time, was investigated with a murine dual-tumor model with both Ov64(−) and Ov64(+) tumors. In vivo gamma imaging (scintigraphy) and whole-body autoradiography (WBA) were acquired, and tissue radioactivity counting was used to supplement the spatial resolution. Both anti-Ov64 antibodies were with 111In with a one-step procedure. The labeling efficiency is higher than 95% which makes post-labeling purification unnecessary. The DTPA-conjugated antibodies are stable at least 10 weeks at −80° C. and are stable at least 120 hrs after labeling. Both sc189 and sc209 demonstrated selective targeting to antigen expressing tumors and only background levels of antibody were found in the corresponding antigen negative tumor in the same animal. This differential tumor targeting was visualized by noninvasive scintigraphy, and validated by ex vivo WBA and tissue counting biodistribution. The tumor exposure for SC189 was 991 nM·h and that number for SC209 was 709 nM·h when 15 µg labeled antibody was injected into a 25 g mouse (0.6 mg/kg).

Conclusions: The Sc189 and Sc209 antibodies have high specificity for the Ov064 expressing ovarian cancers. Imaging technology using labeled anti-Ov064 antibodies is a powerful tool for in vivo tumor detection (Radioimmunoimaging) and staging.

Example 5

Anti-OV64 ADC Shrinks Antigen Expression Tumors In Vivo

Materials and Methods. Eleven week old female nude mice (Taconic Farms, Inc) were inoculated with $2 \times 10^6$ ES2/OV64 cells in the sub cutis and tumor growth was monitored twice weekly with caliper measurements. The mean tumor volume was calculated using the formula $V=W^2 \times L/2$. When the mean tumor volume reached approximately 200 mm³, mice were then randomized into treatment groups containing 10 mice per group. Mice were dosed I.V. (200 µL dosing volume) twice weekly for a total of 5 doses. The dosing solutions were prepared immediately prior to dosing. The dosing solutions for 209-SPDB-DM4 (Lot #2124-109), L-DM4 (Lot#02-058-36-16) and Sc209 antibody were prepared in phosphate buffered saline as the dosing vehicle.

The treatment groups included: vehicle, 300 µg/kg DM4 toxin, 12.4 mg/kg Sc209 naked antibody, 2.1 mg/kg Sc209-DM4 (50 µg DM4 eq.), 6.2 mg/kg Sc209-DM4 (150 µg DM4 eq), and 12.4 mg/kg Sc209-DM4 (300 µg DM4 eq). Tumor growth inhibition (TGI) was calculated at five days after the end of treatment (Day 20) using the formula (control average volume−treated average volume)×100/(control average volume).

Results. The E2-OV64 ovarian tumor model is an engineered tumor model with high expression of OV64 antigen. In vitro Sc209-DM4 demonstrates potency against the ES2-OV64 cells, with an $LD_{50}$ of 2.5 nM (see above). Treatment of tumor bearing nude mice with the naked antibody did not demonstrate statistically significant tumor shrinkage when compared to the control group (TGI=27.5%, p>0.05). Treatment with the DM4 toxin alone at 300 µg/kg did not produce significant efficacy in this model (TGI=21.4%, p>0.05). The low dose Sc209-DM4 toxin conjugate also did not demonstrate significant efficacy (TGI=18%, p>0.05). However, the 150 and 300 µg/kg groups of the Sc209-DM4 toxin conjugates demonstrated highly significant growth inhibition in this model. The TGI for the Sc209-DM4 at 150 and 300 µg/kg are 75% (p<0.001) and 99.4% (p<0.001), respectively. In the 300 µg/kg group there were 7 complete responses observed, with a duration of response of >60 days. There was no body weight loss in any group, in fact there was small weight gain (3-5%) in many of the groups, suggesting that all dose levels were well tolerated. Behavior changes were not observed in any treatment group in this study. In conclusion, this study found that administration of Sc209-DM4 results in dose dependent efficacy against the ES2-Ov64 model on a q3dx5 schedule. The conjugate was well-tolerated at all dose levels on this schedule.

While this invention has been shown and described with references to provided embodiments thereof, it will be understood by those skilled in the art that various changes in form and details may be made therein without departing from the scope of the invention encompassed by the appended claims.

What is claimed is:

1. A method of treating cancer that expresses OV064 in a subject, comprising administering to the subject an anti-OV064 antibody molecule, or an antigen binding fragment thereof, wherein the anti-OV064 antibody molecule or antigen binding fragment is conjugated to a cytotoxic moiety, in an amount sufficient to reduce or inhibit the growth of the subject's cancer;
wherein the anti-OV064 antibody molecule or antigen binding fragment comprises:
(a) three heavy chain complementarity determining regions (HCDR1, HCDR2, and HCDR3) comprising amino acid sequences:
SEQ ID NO: 16 (HCDR1),
SEQ ID NO: 17 (HCDR2), and
SEQ ID NO: 18 (HCDR3); and
(b) three light chain complementarity determining regions (LCDR1, LCDR2, and LCDR3) comprising amino acid sequences:
SEQ ID NO: 25 (LCDR1),
SEQ ID NO: 26 (LCDR2), and
SEQ ID NO: 27 (LCDR3).

2. The method of claim 1, wherein the cancer is ovarian cancer, breast cancer, lung cancer, endometrial cancer, pancreatic cancer, or any metastases thereof.

3. The method of claim 1, wherein the cytotoxic moiety comprises a radioisotope, a therapeutic agent, or a tumor-activated prodrug.

4. The method of claim 3, wherein the therapeutic agent is a maytansine derivative selected from DM1 or DM4.

5. The method of claim 3, wherein the therapeutic agent is an auristatin, a dolastatin, a taxane, a duocarmycin, a calicheamicin, a cryptophycin, a DNA alkylating agent, or any derivative thereof.

6. The method of claim 3, wherein the therapeutic agent is a proteasome inhibitor or a topoisomerase inhibitor.

7. The method of claim 6, wherein the proteasome inhibitor is [(1R)-3-methyl-1-[[(2S)-1-oxo-3-phenyl-2-[(3-mercaptoacetyl)amino]propyl]-amino]butyl]-boronic acid.

8. The method of claim 6, wherein the topoisomerase inhibitor is N,N'-bis[2-(9-methylphenazine-1-carboxamido)ethyl]-1, 2-ethanediamine.

9. The method of claim 1, wherein the antibody or antigen binding fragment thereof is selected from the group consisting of: a human antibody or an antigen binding fragment thereof, a CDR-grafted antibody or an antigen binding fragment thereof, and a chimeric antibody or an antigen binding fragment thereof.

10. The method of claim 1, wherein the anti-OV064 antibody molecule further comprises human or human-derived heavy and light chain variable region frameworks.

11. The method of claim 10, wherein the heavy chain variable region comprises the amino acid sequence of SEQ ID NO: 6 and the light chain variable region comprises the amino acid sequence of SEQ ID NO: 8.

12. The method of claim 10, wherein the anti-OV064 antibody molecule comprises an IgG1 constant region.

* * * * *